United States Patent [19]

Simmonds et al.

[11] Patent Number: 5,763,159

[45] Date of Patent: Jun. 9, 1998

[54] HEPATITIS-C VIRUS TESTING

[75] Inventors: Peter Simmonds, Edinburgh; Shui-Wan Chan, Cambridge; Peng Lee Yap, Edinburgh, all of United Kingdom

[73] Assignee: Common Services Agency, United Kingdom

[21] Appl. No.: 244,116

[22] PCT Filed: Nov. 20, 1992

[86] PCT No.: PCT/GB92/02143

§ 371 Date: Jul. 15, 1994

§ 102(e) Date: Jul. 15, 1994

[87] PCT Pub. No.: WO93/10239

PCT Pub. Date: May 27, 1993

[30] Foreign Application Priority Data

Nov. 21, 1991 [GB] United Kingdom .................... 9124696
Jun. 24, 1992 [GB] United Kingdom .................... 9213362

[51] Int. Cl.[6] ................................................ G01N 33/576
[52] U.S. Cl. .............................. 435/5; 436/518; 530/326; 536/23.72
[58] Field of Search ............................ 435/5; 424/189.1; 536/23.72; 436/518, 820; 530/326

[56] References Cited

U.S. PATENT DOCUMENTS

| | | | |
|---|---|---|---|
| 5,372,928 | 12/1994 | Miyamura et al. | 435/5 |
| 5,428,145 | 6/1995 | Okamoto et al. | 536/23.72 |

FOREIGN PATENT DOCUMENTS

| | | |
|---|---|---|
| 0 318 216 A1 | 5/1989 | European Pat. Off. . |
| 0 388 232 A1 | 9/1990 | European Pat. Off. . |
| 0 398 748 A2 | 11/1990 | European Pat. Off. . |
| 0 435 229 A1 | 12/1990 | European Pat. Off. . |
| 0 414 475 A1 | 2/1991 | European Pat. Off. . |
| 0 442 394 A2 | 8/1991 | European Pat. Off. . |
| 0 445 423 A2 | 9/1991 | European Pat. Off. . |
| 0 464 287 A1 | 1/1992 | European Pat. Off. . |
| 0 468 527 A2 | 1/1992 | European Pat. Off. . |
| WO 92/02642 | 2/1992 | WIPO . |
| WO92/19743 | 11/1992 | WIPO . |
| WO 94/27153 | 11/1994 | WIPO . |
| WO94/25601 | 11/1994 | WIPO . |

OTHER PUBLICATIONS

P. Simmonds, et al.; Hepatitis C quantification and sequencing in blood products, haemophiliacs, and drug users, *The Lancet 336*, pp. 1469–1472 (1990).

N. Enomoto, et al.; There Are Two Major Types Of Heapatitis C Virus In Japan, *Biochemical and Biophysical Research Communications, 170*, pp. 1021–1025 (1990).

Shiu-Wan Chan, et al.; Serological responses to infection with three different types of hepatitis C virus, *The Lancet, 338*, p. 1391 (1991).

H. Okamoto, et al.; Nucleotide sequence of the genomic RNA of hepatitis C virus isolated from a human carrier: comparison with reported isolates for conserved and divergent regions, *Journal of General Virology, 72*, pp. 2697–2704 (1991).

T. Nakao, et al.; Typing of hepatitis C virus genomes by restriction fragment length polymorphism, *Journal of General Virology, 72*, pp. 2105–2112 (1991).

Elizabeth Ann Fagan; Testing for hepatitis C virus; *BMJ 303*, pp. 535–536, 7th Sep. 1991.

E.A.C. Follett et al; HCV confirmatory testing of blood donors. *The Lancet 338*, p. 1024 Oct. 19, 1991.

S.W. Chan, et al.; Analysis of a new hepatitis C virus type and its phylogenetic relationship to existing variants, *Journal of General Virology, 73*, pp. 1131–1141 (1992).

H. Okamoto, et al.; Full-Length Sequence of a Hepatitis C Virus Genome Having Poor Homology to Reported Isolates: Comparative Study of Four Distinct Genotypes, *Virology, 188*, pp. 331–341 (1992).

J. Bukh, et al.; Sequence analysis of the 5' noncoding region of hepatitis C virus, *Proc. Natl. Acad. Sci., 89*, pp. 4942–4946 (1992).

D. W. Bradley; Virology, Molecular Biology, and Serology of Hepatitis C Virus, *Transfusion Medicine Reviews, VI, No. 2*, pp. 93–102 (1992).

*Primary Examiner*—Marian C. Knode
*Assistant Examiner*—Donna C. Wortman
*Attorney, Agent, or Firm*—Bell Seltzer Intellectual Property Law Group of Alston & Bird LLP

[57] ABSTRACT

New styles of hepatitis C virus (HCV), referred to as HCV-3 and HCV-4, have been identified and sequenced. Antigenic regions of HCV-2, HCV-3 and HCV-4 polypeptides have been identified. Immunoassays for HCV and antibodies thereto are described, which allow more complete screening of blood samples for HCV, and allow HCV genotyping.

27 Claims, 39 Drawing Sheets

|  | ▶-255 | ▶-235 | | | | ▶-215 | | ▶-195 |
|---|---|---|---|---|---|---|---|---|
|  | GGCGTTAGTA | CGAGTGTCGT | GCAGCCTCCA | GGACTCCCCC | TCCCGGGAGA | GCCATAGTGG | TCTGCGGAAC |
| E-b1 | .......... | .......... | .......... | .......... | .......... | .......... | .......... |
| E-b2 | .......... | .......... | .......... | .......... | .......... | .......... | .......... |
| E-b3 | .......... | .......... | .......... | ......C... | .......... | .......... | .......... |
| E-b4 | .......... | .......... | .......... | ......C... | .......... | .......... | .......... |
| E-b5 | .......... | .......... | .......... | ......C... | .......... | .......... | .......... |
| E-b6 | .......... | .......... | .......... | ....C.C... | .......... | .......... | .......... |
| E-b7 | .......... | .......... | .......... | ......C... | .......... | .......... | .......... |
| E-b8 | .......... | .......... | .......... | ......C... | .......... | .......... | .......... |
| 2 K2a | .......... | T......A.. | .......... | ......CC.. | .......... | .......... | .......... |
| E-b9 | .......... | T......... | A......... | ......CC.. | .......... | .......... | .......... |
| E-b10 | .......... | T......... | A......... | ......CC.. | .......... | .......... | .......... |
| E-b11 | .......... | T......... | A......... | ......CC.. | .......... | .......... | .......... |
| E-b12 | .......... | T......... | A......... | ......CC.. | .......... | .......... | .......... |
| 2 K2b-1 | .......... | T......A.. | .......... | ......CC.. | .......... | .......... | .......... |
| E-b13 | .......... | T......... | .......... | ......C... | .......... | .......... | .......... |
| E-b14 | .......... | T......... | .......... | ......C... | .......... | .......... | .......... |
| E-b15 | .......... | T......... | .......... | ......C... | .......... | .......... | .......... |
| E-b16 | .......... | T......... | .......... | ......C... | .......... | .......... | .......... |
| E-b17 | .......... | T......... | .......... | ......C... | .......... | .......... | .......... |
| E-b18 | .......... | T......... | .......... | ......C... | .......... | .......... | .......... |

TO FIG. 1b.

| FIG. 1a. | FIG. 1c. |
|---|---|
| FIG. 1b. | FIG. 1d. |

| CGGTGAGTAC | ACCCGAATCG | CTGGGTGAC |
|---|---|---|
| . . . . . . . . . . | . . . . . . . . . . | . . . . . . . . . |
| . . . . . . . . . . | . . . . . . . . . . | . . . . . . . . . |
| . . . . . . . . . . | . . . . . . . . . . | . . . . . . . . . |
| . . . . . . . . . . | . . . . . . . . . . | . . . . . . . . . |
| . . . . . . . . . . | . . . . . . . . . . | . . . . . . . . . |
| . . . . . . . . . . | . . . . . . . . . . | . . . . . . . . . |
| . . . . . . . . . . | . . . . . . . . . . | . . . . . . . . . |
| . . . . . . . . . . | T. . . . . . . . . | .C. . .AA. |
| . . . . . . . . . . | T. . . . . . . . . | .C. . .AA. |
| . . . . . . . . . . | T. . . . . . . . . | .C. . .AA. |
| . . . . . . . . . . | TA. . . . . . . . | .C. . .AAA |
| . . . . . . . . . . | T. . . . . . . . . | .C. . .AAA |
| . . . . . . . . . . | TA. . . . . . . . | .CG. .AA. |
| . . . . . . . . . . | T. . . . . . . . . | .CA. .AC. |
| . . . . . . . . . . | T. . . . . . . . . | .CA. .AC. |
| . . . . . . . . . . | T. . . . . . . . . | .CA. .AC. |
| . . . . . . . . . . | T. . . . . . . . . | .CA. .AC. |
| . . . . . . . . . . | T. . . . . . . . . | .CA. .AC. |
| . . . . . . . . . . | T. . . . . . . . . | .CA. .AC. |
| . . . . . . . . . . | T. . . . . . . . . | .CA. .AC. |

-175 ▸ (ACCCGAATCG column)
-156 ▸ (CTGGGTGAC column)

FROM FIG. 1a.
TO FIG. 1d.

FIG. 1d.

FROM FIG. 1c.

|  | .CA..AC.. |
|  | .CA..AC.. |
| T | .CA..AC.. |
| T | .CA..AC.. |
| T | .CA..AC.. |
| T | .CA..AC.. |
| T | .CA..AC.. |
| T | .C...AG.. |
| T | .C...A... |
| T | .CA..A... |
| T | .CA..AC.. |
| T | .CA..AC.. |
| T | .CA..AC.. |
| T | .CA..AC.. |
| T | .CA..AC.. |

FROM FIG. 1b.

TO FIG. 1g.

|  |  | -155 |  | -135 |  |  | -115 |  | -195 |
|---|---|---|---|---|---|---|---|---|---|---|
|  |  | CGGGTCCTTT | CTTGGAGCAA | CCCGCTCAAT | ACCCAGAAAT | TTGGGCCTGC | CCCCCGGAGA | TCACTAGCCG |
| 2 | E-b1 | .......... | .......... | .......... | .......... | .......... | .......... | .......... |
|  | E-b2 | .......... | .......... | .......... | .......... | .......... | .......... | .......... |
|  | E-b3 | .......... | .......... | .......... | .......... | .......... | .......... | .......... |
|  | E-b4 | .......... | .......... | .......... | .......... | .......... | .......... | .......... |
|  | E-b5 | .......... | .......... | .......... | .......... | .......... | .......... | .......... |
|  | E-b6 | .......... | .......... | .......... | .......... | .......... | .......... | .......... |
|  | E-b7 | .......... | ........A. | .......... | .......... | .......... | .....A.... | ........C. |
|  | E-b8 | .......... | .......... | .......... | .......... | .......... | .......... | .......... |
|  | K2a | T......... | ........TA | ....A..T.. | G...G.TC.. | .......... | .....A.... | .......... |
|  | E-b9 | T......... | ........TA | ....A..T.. | G...G.CC.. | .......... | .....A.... | CTG....... |
|  | E-b10 | T......... | ........TA | ....A..T.. | G...G.CC.. | .......... | .....A.... | CTG....... |
|  | E-b11 | T......... | ........TA | ....A..T.. | GT..G.TC.. | .......... | .....A.... | CTG......T |
|  | E-b12 | T......... | ........TA | ....A..T.. | GT..G.TC.. | .......... | .....A.... | CTG......T |
| 2 | K2b-1 | T......... | ........TA | .......... | GT..G.TC.. | .......... | .....A.... | CTG....... |
|  | E-b13 | .......... | .........T | .......... | G...TG..C. | .......... | .....A.... | CTG....... |
|  | E-b14 | .......... | .........T | .......... | G...TG..C  | .......... | .....A.... | CTG....... |
|  | E-b15 | .......... | ........TT | .......... | G...TG..C. | .......... | .....A.... | CTG....... |
|  | E-b16 | .......... | ........TT | .......... | G...TG..C. | .......... | .....A.... | CTG....... |
|  | E-b17 | .......... | .........T | .......... | G...TG..C. | .......... | .....A.... | CTG....... |
|  | E-b18 | .......... | .........T | .......... | G...TG..C. | .......... | .....A.... | CTG....... |

TO FIG. 1f.

| FIG. 1e. | FIG. 1g. |
|---|---|
| FIG. 1f. | FIG. 1h. |

FROM FIG. 1e.

| | | | | | | | | |
|---|---|---|---|---|---|---|---|---|
| 1 | HCV-1 | ... | T.. | ... | G..TC..G... | ... | ... | CTG... |
| 1 | Pt-1 | ... | TA.. | ... | G..TC..G... | ... | .A.. | CTG... |
| 1 | H77 | ... | TA.. | ... | G..TC..G... | ... | .A.. | CTG... |
| 1 | H90 | ... | TA.. | ... | G..TC..G... | ... | .A.. | CTG... |
| 1 | GM1 | ... | TA.. | ... | G..TC..G... | ... | .A.. | CTG... |
| 1 | GM2 | ... | TA.. | ... | G..TC..G... | ... | .A.. | CTG... |
| 1 | J1 | ... | TA.. | ... | G..TC..G.C | ..C.. | .A.. | CTG... |
| 1 | A1 | ... | TA.. | ... | G..TC..G.C | ... | .A.. | CTG... |
| 1 | S1 | ... | TA.. | ... | G..TC..G... | ... | .A.. | CTG... |
| 1 | T1 | ... | TA.. | ... | G..TC..G... | ... | .A.. | CTG... |
| 1 | U18/124 | ... | T.. | ... | G..TC..G... | ..C.. | .A.. | CTG... |
| 1 | HCV-J | ... | T.. | ... | G..TC..G... | ... | ... | CTG... |
| 1 | HCV-BK | ... | TA.. | ... | G..TC..G... | ... | .A.. | CTG... |
| 1 | HC-J1 | ... | T.. | ... | G..TC..G... | ... | ... | CTG... |
| 1 | HC-J4 | ... | T.. | ... | G..TC..G... | ... | ... | CTG... |

| AGTAGTGTTG | GGTCGCGAAA | GGCC |
|---|---|---|
| ▶-75 | | ▶-62 |

FROM FIG. 1e.

TO FIG. 1h.

| | VTEQDIRVEE | EIYQCCNLEP | EARKVISSLT | ERLYCGGPMF | NSKGAQCCYR | RCRASGVLPT | SFGNTITCYI | KATAACEAAG | LRNPD |
|---|---|---|---|---|---|---|---|---|---|
| 2 E-b1 | .......... | .......... | .......... | .......... | .......... | .......... | .......... | .......... | ..... |
| 2 E-b2 | .......... | .......... | .......... | .......... | .......... | .......... | .......... | .......... | ..... |
| 2 E-b3 | .......... | .......... | .......... | .......... | .......... | .......... | .......... | ....K..... | ..... |
| 2 E-b7 | .......... | .......... | .......... | .......... | .......... | .......... | .......... | ....K..... | ..... |
| 2 K2a | ...R...T.. | S..RA.S.PE | ...HIA.H.. | ....V..... | .....QT... | .......T.. | .......M.. | ....L..K.. | IVA.S |
| 2 K2a | ...R...T.. | S...A.S.PE | ....TA.H.. | ....V..... | .....QT... | .......T.. | .......M.. | ....L..K.. | IVA.T |
| 2 E-b9 | .......... | S...A.S.PQ | ....T..H.. | ....V..... | .....QS... | ......FT.. | .......M.. | ....L...K. | IVD.T |
| 2 K2b-1 | ...R...T.. | S...A.S.PQ | .......... | ....V..... | .....QS... | ......FT.. | .....M..M. | ....L...K. | IVD.I |
| 2 K2b-1 | ...R...T.. | S...A.S.PE | .......... | ....V..... | .....QS... | ......FT.. | .....M..M. | ....L...K. | IVD.I |
| 1 HCV-1 | ...S...T.. | A......D.D | Q..VA.K... | ....V...LT | .....R.EN. | .......T.. | .......C.L | ....R..R.. | .QDCT |
| 1 Pt-1 | ...S...T.. | A......D.D | Q..VA.K... | ....V...LT | .....R.EN. | .......T.. | .....C..L. | ....R..R.. | ..DCT |
| 1 H77 | ...S...T.. | A......D.D | Q..VA.K... | ....V...LT | .....R.EN. | .......T.. | .......C.L | ....R..R.. | .QDCT |
| 1 H90 | ...S...T.. | A......D.D | Q..TA.K... | ....V...LT | .....R.EN. | .......T.. | .......C.L | ....R..R.. | .QDCT |
| E-b17 | ...N....N. | S.......D.A | .QA....R.. | ....V...LT | ......QN.. | .......T.. | .....C..L. | ....S..R.K | .QDCT |
| E-b18 | ...N....N. | S......D.A | .QA....K.. | .....I..LT | ......QN.. | .......T.. | .....C..L. | ....S..R.K | .QDCT |
| E-b18 | ...N....N. | S....S.D.A | .QA....R.. | .....I..LT | ......QN.. | .......T.. | .....C..L. | .......R.K | .QDCT |
| E-b18 | ...N....N. | S......A.A | .QA....R.. | .....I..LT | ......QN.. | .......T.. | .....C..L. | .......R.K | .QDCT |
| E-b18 | ...N....N. | S......D.A | .Q.....R.. | .....I..LT | ......QN.. | .......T.. | .....C..L. | ....S..R.K | .QDCT |
| E-b18 | ...N....N. | S......D.A | ..KLA.R... | .....I..LT | ......QN.. | .......T.. | .....C..L. | ....S..R.K | ..DCT |
| E-b18 | ...N....N. | S......D.A | .Q.....R.. | .....I..LT | ......QN.. | .......T.. | .....C..L. | ....S..R.K | .QDCT |

| | 1577 KQQGLNFSYL | TAYQATVCAR | 1597 AQALPPSWDE | TWKCLVRLKP | 1617 TLHGPTPLLY | 1633 RLGPVQN |
|---|---|---|---|---|---|---|
| E-b1 | .......... | .......... | .......... | .......... | .......... | ....... |
| E-b2 | .......... | .......... | .P........ | .......M.. | .......... | ....... |
| E-b6 | .......... | .......... | .P........ | .......... | .......... | ....... |
| E-b7 | .......... | ....A..... | .P........ | .......... | .......... | ....... |
| ? Clone A | ..G.D..A.. | .......... | ..K.P....V | .......M.A | ......I... | ..A.T.. |
| E-b6 | ..S.E.LP.. | V......... | .P......Q | .......M.. | .......... | ...A... |
| E-b7 | ..S.E.LP.. | V......... | .P......Q | .......M.I | .......... | ...A... |
| Group 1/1 | ..S.E.LP.. | V......... | .P......Q | .......M.I | .......... | ...A... |
| 1/2 | ..S.E.LP.. | V......... | .P......Q | .....R.M.I | .......... | ....... |
| 1/3 | ..S.E.P.. | V......... | .P......Q | .......M.I | .......... | ....... |
| 1/4 | ..S.E.P.. | V......... | .P......Q | .......M.A | .......... | ....... |
| 1/4 | ..S.E.P.. | V......... | .P....EQ | .......M.A | .......... | ...A... |
| 1 HCV-1 H77 | ..S.E.LP.. | V......... | .P......Q | .......M.I | .......... | ...A... |
| 1 H90 | ..S.E.P.. | V......... | .P......Q | .......M.I | .......... | ...A... |
| 1 | ..S.E.P.. | V......... | .P......Q | .......M.I | .......... | ...A... |
| 1 HCV-J | ..A.D.LP.. | V......... | .P......Q | .......M.I | .......... | ...A... |
| 1 HCV-BK | ..A.D.P.. | V......... | .P......Q | .......M.I | .......... | ...A... |
| 1 JH | ..A.D.P.. | V......... | ..K.P....Q | .......M.I | .......... | ...A... |

FIG. 5.

| E-b1 | AKPQRKTKRN | TIRRPQDVKF | PGGGQIVGGV | YVLPRRGPRL | GVCATRKTSE | RSQPRGRRQP |
|---|---|---|---|---|---|---|
| 1 HCV-1 | P...K.N... | .........N | .......... | ....L..... | .......... | .......... |
| 1 H77 | P......... | .........N | .......... | ....L..... | .R........ | .......... |
| 1 H90 | P......... | .........N | .......... | ....L..... | .R........ | .......... |
| 1 GM1 | .......... | .........N | .......... | ....L..... | .R........ | .......... |
| 1 GM2 | .......... | .........N | .......... | ....L..... | .R.....P.. | .......... |
| 1 HCV-J | P......... | .........N | .......... | ....L..... | .R........ | .......... |
| 1 HCV-BK | P......... | .........N | .......... | ....L..... | .R.....P.. | .......... |
| 1 HC-J1 | P......... | .........N | .......... | ....L..... | .R........ | .......... |
| 1 HC-J4 | P......... | .........N | .......... | ....L..... | .R........ | .......... |
| 1 JH | P......... | .........N | .......... | ....L..... | .R........ | ......W... |
| 1 J7 | P......... | .........N | .......... | ....L..... | .R........ | .......... |

FIG. 7a.

| E-b1 | IPKARRSEGR | SWAQPGYPWP | LYGNEGCGWA | GVLLSPRGSR | PSWGPNDPRR | RSRNLGKVID | TLTW |
|---|---|---|---|---|---|---|---|
| 1 HCV-1 | .......... | T......... | .......... | .......... | .......... | .......... | ..C. |
| 1 H77 | ....P..... | T......... | .......... | .......... | ...T...... | .......... | ..C. |
| 1 H90 | ....P..... | T......... | .......... | .......... | ...T...... | .......... | .FC. |
| 1 GM1 | ....P..... | T......... | .......... | .......... | ...T...... | .......... | ..C. |
| 1 GM2 | ....P..... | T......... | .......... | .......... | .......... | .......... | ..C. |
| 1 HCV-J | ....P..... | T......... | .......M.. | .......... | ...T...... | .......... | ..C. |
| 1 HCV-BK | ....P..... | T......... | ....L..... | .......... | ...T...... | .......... | ..C. |
| 1 HC-J1 | V..P...... | T......... | .......... | .......... | ...T...... | .......... | ..C. |
| 1 HC-J4 | ....P..... | T......... | ....L..... | .......... | ...T...... | .......... | ..C. |
| 1 JH | ....P..... | T......... | ....L..... | .......... | .......... | .......... | ..C. |
| 1 J7 | ....P..... | T......... | ....L..... | .......... | ...T...... | .......... | ..C. |

NUCLEOTIDE SEQUENCES

```
       4911                                                              4970
        ▼                                                                 ▼
T0040  GACACACCCU GUCACAAAAU ACAUCAUGGC AUGCAUGUCA GCUGAUCUGG AAGUAACCAC
T0038  ??CACACCCC GUCACAAAAU ACAUCAUGCC AUGCAUGUCA GCUGAUCUGG AAGUAACCAC
T0036  ??CACACCCC AUCACAAAAU ACAUCAUGGC AUGCAUGUCA GCUGAUCUGG AAGUAACCAC
T0026  ????CACCCC AUCGCGAAAU ACCUCAUGGC AUGUAUGUCA GCUGAUCUGG AAGUAACCAC
T1787  ????CACCCC AUCACAAAAU ACGUCAUGGC AUGCAUGUCA GCUGAUCUGG AAGUAACCAC
       ---------- ---------- ---------- ---------- ---------- ----------
Cons   GACACACCCU GUCACAAAAU ACAUCAUGGC AUGCAUGUCA GCUGAUCUGG AAGUAACCAC
       4971                                                              5030
        ▼                                                                 ▼
T0040  CAGCACCUGG GUGUUGCUUG GAGGGGUCCU CGCGGCCCUA GCGGCCUACU GCUUGUCAGU
T0038  CAGCACCUGG GUGUUGCUUG GAGGGGUCCU CGCGGCCCUA GCGGCCUACU GCUUGUCAGU
T0036  CAGCACCUGG GUGUUGCUUG GAGGGGUCCU CGCGGCCCUA GCGGCCUACU GCUUGUCAGU
T0026  CAGCACCUGG GUGUUGCUUG GAGGAGUCCU CGCUGCCCUA GCGGCCUACU GCUUGUCAGU
T1787  CAGCACCUGG GUGUUGCUUG GAGGGGUCCU CGCGGCCCUA GCGGCCUACU GCUUGUCAGU
       ---------- ---------- ---------- ---------- ---------- ----------
Cons   CAGCACCUGG GUGUUGCUUG GAGGGGUCCU CGCGGCCCUA GCGGCCUACU GCUUGUCAGU
       5031                                                              5090
        ▼                                                                 ▼
T0040  CGGCUGCGUU GUGAUUGUGG GUCAUAUUGA GCUGGGGGGC AAGCCGGCA  AUCGUCCAGA
T0038  CGGCUGCGUU GUGAUUGUGG GCCAUAUUGA GCUGGGGGGC AAGCCCGCA  CUCGUCCAGA
T0036  CGGCUGCGUU GUGAUUGUGG GCCAUAUUGA GCUGGGGGGC AAGCCGGCA  CUCGUCCAGA
T0026  CGGCUGCGUU GUGAUUGUGG GUCAUAUUGA GCUGGGGGGC AAGCCAGCA  CUCGUCCAGA
T1787  CGGCUGCGUU GUGAUUGUGG GUCAUAUUGA GCUGGGAGGC AAGCCGGCA  CUCGUCCAGA
       ---------- ---------- ---------- ---------- ---------- ----------
Cons   CGGCUGCGUU GUGAUUGUGG GUCAUAUUGA GCUGGGGGGC AAGCCGGCA  AUCGUCCAGA
       5091                                                              5150
        ▼                                                                 ▼
T0040  CAAAGAGGUG UUGUAUCAAC AAUACGAUGA GAUGGAGGAG UCCUCGCAA  GCUGCCCCAUA
T0038  CAAAGAAGUG UUGUAUCAAC AAUACGAUGA GAUGGAGGAG UCCUCGCAA  GCUGCCCCAUA
T0036  CAAAGAGGUG UUGUAUCAAC AAUACGAUGA GAUGGAGGAG UCCUCGCAA  GCUGCCCCAUA
T0026  CAAAGAGGUG UUGUAUCAAC AAUACGAUGA GAUGGAGGAG UCCUCGCAA  GCUGCCCCAUA
T1787  CAAGGAGGUG UUGUAUCAAC AAUACGAUGA GAUGGAGGAG UCCUCGCAA  GCUGCCCCAUA
       ---------- ---------- ---------- ---------- ---------- ----------
Cons   CAAAGAGGUG UUGUAUCAAC AAUACGAUGA GAUGGAGGAG UCCUCGCAA  GCUGCCCCAUA
       5051                                                              5210
        ▼                                                                 ▼
T0040  UAUCGAACAA GCUCAGGUGA UAGCCCA CA GUUCAAGGAG AAAGUCCUU GGAUUGCUGCA
T0038  UAUCGAACAA GCUCAAGUAA UAGCCCA CA GUUCAAGGAG AAAGUCCUU GGAUUGCUGCA
T0036  UAUCGAACAA GCUCAGGUAA UAGCCCA CA GUUCAAGGAG AAAGUCCUU GGAUUGCUGCA
T0026  UAUCGAACAA GCUCAGGUAA UAGCCCA CA GUUCAAGGAG AAAGUCCUU GGAUUGCUGCA
T1787  UAUCGAACAA GCUCAGGUAA UAGCCCA CA GUUCAAGGAG AAAGUCCUU GGGUUGCUGCA
       ---------- ---------- ------- -- ---------- ---------- -----------
Cons   UAUCGAACAA GCUCAGGUGA UAGCCCA CA GUUCAAGGAG AAAGUCCUU GGAUUGCUGCA
```

FIG. 9a.

```
        5211                                                           5270
         ▼                                                              ▼
T0040  GCGAGCCACC  CAACAACAAG  CUGUUAU GA  GCCAAUAGUA  GCUACCAAC  UGGCAAAAGCU
T0038  GCGGGCCACC  CAACAACAAG  CUGUUAU GA  GCCCAUAGUA  GCUACCAAC  UGGCAAAAGCU
T0036  GCGAGCCACC  CAACAACAAG  CUGUUAU GA  GCCAAUAGUA  GCUACCAAC  UGGCAAAA???
T0026  GCGAGCCACC  CAACAACAAG  CUGUCAU GA  GCCCAUAGUA  GCUACCAAC  UGGCAAAA???
T1787  GCGAGCCACC  CAACAACAGG  CUGUCAU GA  GCCCAUAGUA  GCUACCAAC  UGGCAAAAGCU
       ----------  ----------  -------- -- ----------  ---------  -----------
Cons   GCGAGCCACC  CAACAACAAG  CUGUUAU GA  GCCCAUAGUA  GCUACCAAC  UGGCAAAAGCU
        5271
         ▼
T0040  UGAGACC
T0038  UGAGGCC
T0036  ???????
T0026  ???????
T1787  UGAGGCU
       -------
Cons   UGAGACC
```

FIG. 9b.

DEDUCED AMINO ACID SEQUENCES

```
       1638                                                            1787
        ▼                                                               ▼
T0040  THPVT  KYIMA  CMSAD  LEVTT  STWVL LGGVL  AALAA  YCLSV  GCVVI  VGHIE
T0038  .HPVT  KYIMA  CMSAD  LEVTT  STWVL LGGVL  AALAA  YCLSV  GCVVI  VGHIE
T0036  .HPIT  KYIMA  CMSAD  LEVTT  STWVL LGGVL  AALAA  YCLSV  GCVVI  VGHIE
T0026  .HPIA  KYLMA  CMSAD  LEVTT  STWVL LGGVL  AALAA  YCLSV  GCVVI  VGHIE
T1787  .HPIT  KYYMA  CMSAD  LEVTT  STWVL LGGVL  AALAA  YCLSV  GCVVI  VGHIE
       -----  -----  -----  -----  ----- -----  -----  -----  -----  -----
Cons   THPVT  KYIMA  CMSAD  LEVTT  STWVL LGGVL  AALAA  YCLSV  GCVVI  VGHIE 1688                                                            1737
        ▼                                                               ▼
T0040  LGGKP  AIVPD  KEVAY  QQYDE  MEECS QAAPY  IEQAQ  VIAHQ  FKEKV  LGLLQ
T0038  LGGKP  ALVPD  KEVAY  QQYDE  MEECS QAAPY  IEQAQ  VIAHQ  FKEKV  LGLLQ
T0036  LGGKP  ALVPD  KEVAY  QQYDE  MEECS QAAPY  IEQAQ  VIAHQ  FKEKV  LGLLQ
T0026  LGGKP  ALVPD  KEVAY  QQYDE  MEECS QAAPY  IEQAQ  VIAHQ  FKEKV  LGLLQ
T1787  LGGKP  ALVPD  KEVAY  QQYDE  MEECS QAAPY  IEQAQ  VIAHQ  FKEKV  LGLLQ
       -----  -----  -----  -----  ----- -----  -----  -----  -----  -----
Cons   LGGKP  ALVPD  KEVAY  QQYDE  MEECS QAAPY  IEQAQ  VIAHQ  FKEKV  LGLLQ 1738                        1765
        ▼                           ▼
T0040  RATQQ  QAVIE  PIVAT  NWQKL  ETFWH KHM
T0038  RATQQ  QAVIE  PIVAT  NWQKL  EAFWH KHM
T0036  RATQQ  QAVIE  PIVAT  NWQ..  ..... ...
T0026  RATQQ  QAVIE  PIVAT  NWQ..  ..... ...
T1787  RATQQ  QAVIE  PIVAT  NWQKL  EAFWH KHM
       -----  -----  -----  -----  ----- ---
Cons   RATQQ  QAVIE  PIVAT  NWQKL  EAFWH KHM
```

FIG. 9c.

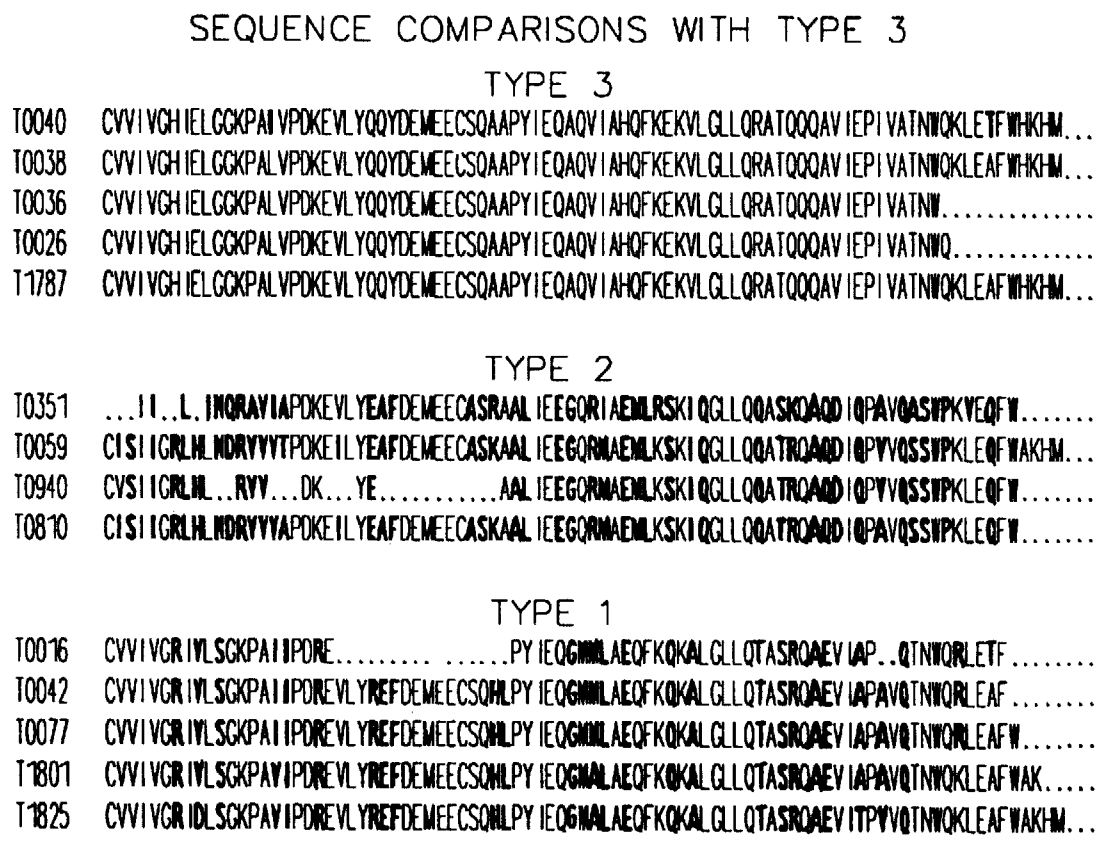

SEQUENCE COMPARISONS WITH TYPE 3

TYPE 3

T0040 CVVIVGHIELGGKPAIVPDKEVLYQQYDEMEECSQAAPYIEQAQVIAHQFKEKVLGLLQRATQQQAVIEPIVATNWQKLETFWHKHM...
T0038 CVVIVGHIELGGKPALVPDKEVLYQQYDEMEECSQAAPYIEQAQVIAHQFKEKVLGLLQRATQQQAVIEPIVATNWQKLEAFWHKHM...
T0036 CVVIVGHIELGGKPALVPDKEVLYQQYDEMEECSQAAPYIEQAQVIAHQFKEKVLGLLQRATQQQAVIEPIVATNW.............
T0026 CVVIVGHIELGGKPALVPDKEVLYQQYDEMEECSQAAPYIEQAQVIAHQFKEKVLGLLQRATQQQAVIEPIVATNWQ............
T1787 CVVIVGHIELGGKPALVPDKEVLYQQYDEMEECSQAAPYIEQAQVIAHQFKEKVLGLLQRATQQQAVIEPIVATNWQKLEAFWHKHM...

TYPE 2

T0351 ...II..L.INQRAVIAPDKEVLYEAFDEMEECASRAALIEEGQRIAEMLRSKIQGLLQQASKQAQDIQPAVQASWPKVEQFW.......
T0059 CISIIGRLHLNDRVVVTPDKEILYEAFDEMEECASKAALIEEGQRMAEMLKSKIQGLLQQATRQAQDIQPVVQSSWPKLEQFWAKHM...
T0940 CVSIIGRLHL..RVV...DK...YE...........AALIEEGQRMAEMLKSKIQGLLQQATRQAQDIQPVVQSSWPKLEQFW.......
T0810 CISIIGRLHLNDRVVVAPDKEILYEAFDEMEECASKAALIEEGQRMAEMLKSKIQGLLQQATRQAQDIQPAVQSSWPKLEQFW.......

TYPE 1

T0016 CVVIVGRIVLSGKPAIIPDRE......... ......PYIEQGMMLAEQFKQKALGLLQTASRQAEVIAP..QTNWQRLETF........
T0042 CVVIVGRIVLSGKPAIIPDREVLYREFDEMEECSQHLPYIEQGMMLAEQFKQKALGLLQTASRQAEVIAPAVQTNWQRLEAF........
T0077 CVVIVGRIVLSGKPAIIPDREVLYREFDEMEECSQHLPYIEQGMMLAEQFKQKALGLLQTASRQAEVIAPAVQTNWQRLEAFW.......
T1801 CVVIVGRIVLSGKPAVIPDREVLYREFDEMEECSQHLPYIEQGMALAEQFKQKALGLLQTASRQAEVIAPAVQTNWQKLEAFWAK.....
T1825 CVVIVGRIDLSGKPAVIPDREVLYREFDEMEECSQHLPYIEQGMALAEQFKQKALGLLQTASRQAEVITPVVQTNWQKLEAFWAKHM...

FIG. 10a.

DERIVATION OF PEPTIDE SEQUENCES

TYPE 3

| | |
|---|---|
| T0040 | CVVIVGHIELCGKPALVPDKEVLYQQYDEMEECSQAAPYIEQAQVIAHQFKEKVLGLLQRATQQQAVIEPIYATNWQKLETFWHCHM |
| T0038 | CVVIVGHIELCGKPALVPDKEVLYQQYDEMEECSQAAPYIEQAQVIAHQFKEKVLGLLQRATQQQAVIEPIYATNWQKLEAFWHCHM |
| T0036 | CVVIVGHIELCGKPALVPDKEVLYQQYDEMEECSQAAPYIEQAQVIAHQFKEKVLGLLQRATQQQAVIEPIYATNW............ |
| T0026 | CVVIVGHIELCGKPALVPDKEVLYQQYDEMEECSQAAPYIEQAQVIAHQFKEKVLGLLQRATQQQAVIEPIYATNWQ........... |
| T1787 | CVVIVGHIELCGKPALVPDKEVLYQQYDEMEECSQAAPYIEQAQVIAHQFKEKVLGLLQRATQQQAVIEPIYATNWQKLEAFWHCHM |
| PepId | CVVIVGHIELCGKPALVPDKEVLYQQYDEMEECSQAAPYIEQAQVIAHQFKEKVLGLLQRATQQQAVIEPIYATNWQKLEAFWHCHM |

TYPE 2

| | |
|---|---|
| T0351 | ....II...L...INQRAVIAPDKEVLYEAFDEMEECASRAAL.IEEGQRIAEMLRSKIQGLLQQASRQAQDIQPAVQASNPKYEQFW........ |
| T0059 | CISIIGRLHLNDRVVYPDKEILYEAFDEMEECASKAALIEEGQRMAEMLKSKIQGLLQQATRQAQDIQPVVQSSNPKLEQFWAKHHMV W |
| T0940 | CVVSIIGRLH...RVV..DK..YE...............AAL.IEEGQRMAEMLKSKIQGLLQQATRQAQDIQPVVQSSNPKLEQFW..... |
| T0870 | CISIIGRLHLNDRVVAPDKEILYEAFDEMEECASKAALIEEGQRMAEMLKSKIQGLLQQATRQAQDIQPAVQSSNPKLEQFWAKHHMV W |
| PepId | CISIIGRLHLNDRVVAPDKEILYEAFDEMEECASKAALIEEGQRMAEMLKSKIQGLLQQATRQAQDIQPAVQSSNPKLEQFWAKHHMV W |

TYPE 1

| | |
|---|---|
| T0016 | CVVIVGRIVLSGKPAIIPDRE........................PYIEQGMALAEQFKQKALGLLQTASRQAEVIAPAQTNMQRLETF........ |
| T0042 | CVVIVGRIVLSGKPAIIPDREVLYREFDEMECSQHLPYIEQGMALAEQFKQKALGLLQTASRQAEVIAPAVQTNMQRLEAF............ |
| T0077 | CVVIVGRIVLSGKPAIIPDREVLYREFDEMECSQHLPYIEQGMALAEQFKQKALGLLQTASRQAEVIAPAVQTNMQRLEAF........... |
| T1801 | CVVIVGRIVLSGKPAVIPDREVLYREFDEMECSQHLPYIEQGMALAEQFKQKALGLLQTASRQAEVIAPAVQTNMQRLEAFWAK....... |
| T1825 | CVVIVGRIDLSGKPAVIPDREVLYREFDEMECSQHLPYIEQ.MALAEQFKQKALGLLQTASRQAEVIAPAVQTNMQRLEAFWAK....M... |
| PepId | CVVIVGRIDLSGKPAVIPDREVLYREFDEMECSQHLPYIEQ.MALAEQFKQKALGLLQTASRQAEVIPYVQTNMQRLEAFWAKHHMINF |

FIG. 10b.

TYPE 3

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P1   CVVIVGHIE
P2    VVIVGHIEL
P3     VIVGHIELG
P4      IVGHIELGG
P5       VGHIELGGK
P6        GHIELGGKP
P7         HIELGGKPA
P8          IELGGKPAL
P9           ELGGKPALV
P10           LGGKPALVP

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P11            GGKPALVPD
P12             GKPALVPDK
P13              KPALVPDKE
P14               PALVPDKEV
P15                ALVPDKEVL
P16                 LVPDKEVLY
P17                  VPDKEVLYQ
P18                   PDKEVLYQQ
P19                    DKEVLYQQY
P20                     KEVLYQQYD

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P21                      EVLYQQYDE
P22                       VLYQQYDEM
P23                        LYQQYDEME
P24                         YQQYDEMEE
P25                          QQYDEMEEC
P26                           QYDEMEECS
P27                            YDEMEECSQ
P28                             DEMEECSQA
P29                              EMEECSQAA
P30                               MEECSQAAP

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P31                                EECSQAAPY
P32                                 ECSQAAPYI
P33                                  CSQAAPYIE
P34                                   SQAAPYIEQ
P35                                    QAAPYIEQA
P36                                     AAPYIEQAQ
P37                                      APYIEQAQV
P38                                       PYIEQAQVI
P39                                        YIEQAQVIA
P40                                         IEQAQVIAH

FIG. 11a.

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P41  EQAQVIAHQ
P42  QAQVIAHQF
P43  AQVIAHQFK
P44  QVIAHQFKE
P45  VIAHQFKEK
P46  IAHQFKEKV
P47  AHQFKEKVL
     HQFKEKVLG
P49  QFKEKVLGL
P50  FKEKVLGLL

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P51  KEKVLGLLQ
P52  EKVLGLLQR
P53  KVLGLLQRA
P54  VLGLLQRAT
P55  LGLLQRATQ
P56  GLLQRATQQ
P57  LLQRATQQQ
P58  LQRATQQQA
P59  QRATQQQAV
P60  RATQQQAVI

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P61  ATQQQAVIE
P62  TQQQAVIEP
P63  QQQAVIEPI
P64  QQAVIEPIV
P65  QAVIEPIVA
P66  AVIEPIVAT
P67  VIEPIVATN
P68  IEPIVATNW
P69  EPIVATNWQ
P70  PIVATNWQK

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P71  IVATNWQKL
P72  VATNWQKLE
P73  ATNWQKLEA
P74  TNWQKLEAF
P75  NWQKLEAFW
P76  WQKLEAFWA
P77  QKLEAFWAK
P78  KLEAFWAKH
P79  LEAFWAKHM
P80  EAFWAKHMW

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

P81  AFWAKHMWN
P82  FWAKHMWNF

FIG. 11b.

TYPE 2

```
HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF

P 1    CISIIGRLH
P 2     ISIIGRLHL
P 3      SIIGRLHLN
P 4       IIGRLHLND
P 5        IGRLHLNDR
P 6         GRLHLNDRV
P 7          RLHLNDRVV
P 8           LHLNDRVVV
P 9            HLNDRVVVT
P 10            LNDRVVVTP

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF

P 11             NDRVVVTPD
P 22              DRVVVTPDK
P 33               RVVVTPDKE
P 44                VVVTPDKEI
P 55                 VVTPDKEIL
P 66                  VTPDKEILY
P 77                   TPDKEILYE
P 88                    PDKEILYEA
P 99                     DKEILYEAF
P 20                      KEILYEAFD

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF

P 21                        EILYEAFDE
P 22                         ILYEAFDEM
P 23                          LYEAFDEME
P 24                           YEAFDEMEE
P 25                            EAFDEMEEC
P 26                             AFDEMEECA
P 27                              FDEMEECAS
P 28                               DEMEECASK
P 29                                EMEECASKA
P 30                                 MEECASKAA

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF

P 31                                  EECASKAAL
P 32                                   ECASKAALI
P 33                                    CASKAALIE
P 34                                     ASKAALIEE
P 35                                      SKAALIEEG
P 36                                       KAALIEEGQ
P 37                                        AALIEEGQR
P 38                                         ALIEEGQRM
P 39                                          LIEEGQRMA
P 40                                           IEEGQRMAE
```

FIG. 11c.

```
HCV-2  CISIIGRLHLNDRVVVTPDKEILYEAFDEMEECASKAALIEECQRMAEMLKSIQGLLQQATRQAQDIQPVVQSSWPKLEQFWAKHMWNF
P41                                   EECQRMAEM
P42                                    ECQRMAEML
P43                                     CQRMAEMLK
P44                                      QRMAEMLKS
P45                                       RMAEMLKSK
P46                                        MAEMLKSKI
P47                                         AEMLKSKIQ
P48                                          EMLKSKIQG
P49                                           MLKSKIQGL
P50                                            LKSKIQGLL

HCV-2  CISIIGRLHLNDRVVVTPDKEILYEAFDEMEECASKAALIEECQRMAEMLKSIQGLLQQATRQAQDIQPVVQSSWPKLEQFWAKHMWNF
P51                                             KSKIQGLLQ
P52                                              SKIQGLLQQ
P53                                               KIQGLLQQA
P54                                                IQGLLQQAT
P55                                                 QGLLQQATR
P56                                                  GLLQQATRQ
P57                                                   LLQQATRQA
P58                                                    LQQATRQAQ
P59                                                     QQATRQAQD
P60                                                      QATRQAQDI

HCV-2  CISIIGRLHLNDRVVVTPDKEILYEAFDEMEECASKAALIEECQRMAEMLKSIQGLLQQATRQAQDIQPVVQSSWPKLEQFWAKHMWNF
P61                                                        ATRQAQDIQ
P62                                                         TRQAQDIQP
P63                                                          RQAQDIQPV
P64                                                           QAQDIQPVV
P65                                                            AQDIQPVVQ
P66                                                             QDIQPVVQS
P67                                                              DIQPVVQSS
P68                                                               IQPVVQSSW
P69                                                                QPVVQSSWP
P70                                                                 PVVQSSWPK

HCV-2  CISIIGRLHLNDRVVVTPDKEILYEAFDEMEECASKAALIEECQRMAEMLKSIQGLLQQATRQAQDIQPVVQSSWPKLEQFWAKHMWNF
P71                                                                   VVQSSWPKL
P72                                                                    VQSSWPKLE
P73                                                                     QSSWPKLEQ
P74                                                                      SSWPKLEQF
P75                                                                       SWPKLEQFW
P76                                                                        WPKLEQFWA
P77                                                                         PKLEQFWAK
P78                                                                          KLEQFWAKH
P79                                                                           LEQFWAKHM
P80                                                                            EQFWAKHMW

HCV-2  CISIIGRLHLNDRVVVTPDKEILYEAFDEMEECASKAALIEECQRMAEMLKSIQGLLQQATRQAQDIQPVVQSSWPKLEQFWAKHMWNF
P81                                                                              QFWAKHMWN
P82                                                                               FWAKHMWNF
```

FIG. 11d.

TYPE 1

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 1   CVVIVGRIV
P 2    VVIVGRIVL
P 3     VIVGRIVLS
P 4      IVGRIVLSG
P 5       VGRIVLSGK
P 6        GRIVLSGKP
P 7         RIVLSGKPA
P 8          IVLSGKPAI
P 9           VLSGKPAII
P 10           LSGKPAIIP
```

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 11            SGKPAIIPD
P 12             GKPAIIPDR
P 13              KPAIIPDRE
P 14               PAIIPDREV
P 15                AIIPDREVL
P 16                 IIPDREVLY
P 17                  IPDREVLYR
P 18                   PDREVLYRE
P 19                    DREVLYREF
P 20                     REVLYREFD
```

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 21                      EVLYREFDE
P 22                       VLYREFDEM
P 23                        LYREFDEME
P 24                         YREFDEMEE
P 25                          REFDEMEEC
P 26                           EFDEMEECS
P 27                            FDEMEECSQ
P 28                             DEMEECSQH
P 29                              EMEECSQHL
P 30                               MEECSQHLP
```

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 31                                EECSQHLPY
P 32                                 ECSQHLPYI
P 33                                  CSQHLPYIE
P 34                                   SQHLPYIEQ
P 35                                    QHLPYIEQG
P 36                                     HLPYIEQGM
P 37                                      LPYIEQGMM
P 38                                       PYIEQGMML
P 39                                        YIEQGMMLA
P 40                                         IEQGMMLAE
```

FIG. 11e.

```
HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

P41                                    EQGMMLAEQ
P42                                     QGMMLAEQF
P43                                      GMMLAEQFK
P44                                       MMLAEQFKQ
P45                                        MLAEQFKQK
P46                                         LAEQFKQKA
P47                                          AEQFKQKAL
P48                                           EQFKQKALG
P49                                            QFKQKALGL
P50                                             FKQKALGLL

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

P51                                              KQKALGLLQ
P52                                               QKALGLLQT
P53                                                KALGLLQTA
P54                                                 ALGLLQTAS
P55                                                  LGLLQTASR
P56                                                   GLLQTASRQ
P57                                                    LLQTASRQA
P58                                                     LQTASRQAE
P59                                                      QTASRQAEV
P60                                                       TASRQAEVI

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

P61                                                        ASRQAEVIA
P62                                                         SRQAEVIAP
P63                                                          RQAEVIAPA
P64                                                           QAEVIAPAV
P65                                                            AEVIAPAVQ
P66                                                             EVIAPAVQT
P67                                                              VIAPAVQTN
P68                                                               IAPAVQTNW
P69                                                                APAVQTNWQ
P70                                                                 PAVQTNWQR

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

P71                                                                  AVQTNWQRL
P72                                                                   VQTNWQRLE
P73                                                                    QTNWQRLEA
P74                                                                     TNWQRLEAF
P75                                                                      NWQRLEAFW
P76                                                                       WQRLEAFWA
P77                                                                        QRLEAFWAK
P78                                                                         RLEAFWAKH
P79                                                                          LEAFWAKHM
P80                                                                           EAFWAKHMW

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

P81                                                                            AFWAKHMWN
P82                                                                             FWAKHMWNF
```

| | | | | | | | |
|---|---|---|---|---|---|---|---|
| | ▼-245 | ▼-235 | ▼-225 ▼-216 | ▼-185 | ▼-175 | ▼-165 | ▼-155 |
| | TGAGTGTCGT | GCAGCCTCCA | GGACCCCCCC | CGGTGAGTAC | ACCGGAATTG | CCAGGACCAC | CGGGTCCTTT |
| 1a HCV-1 | .......... | .......... | .......... | .......... | .......... | .......... | .......... |
| 1b HCV-J | .........T | .....A.... | .C........ | .......... | .......... | ...G..A... | ........T. |
| 2a HC-J6 | .......... | .......... | .C........ | .......... | .......... | ...G..A... | ........T. |
| 2b HC-J8 | .......... | .......... | .......... | .......... | .......... | ...G..A... | .......... |
| 3a E-b1 | C......... | .......... | T......... | .......... | ......C... | .TG....GT. | .......... |
| 4 Eg-16(1) | .......... | .......... | .......... | .......... | ......C... | ...G...T.. | .......... |
| Eg-29(1) | .........T | .....A.... | .......... | .......... | ......C... | ...G...T.. | .......... |
| Eg-33(2) | .........T | .....A.... | .......... | .......... | ......C... | ...G...T.. | .......... |
| Eg-3(3) | .........T | .....A.... | .......... | .......... | ......C... | ...G...T.. | .......... |
| Eg-9(3) | .........T | .......... | .......... | .......... | ......C... | ...G...T.. | .......... |
| Eg-12(3) | .........T | .......... | T......... | .......... | ......C... | ...G...T.. | .......... |
| Eg-13(3) | .........T | .....A.... | .......... | .......... | ......C... | ...G...T.. | .......... |
| Eg-21(3) | .........T | .....A.... | .......... | .......... | ......C... | ...G...T.. | .......... |
| Eg-14(4) | .........T | .....A.... | .......... | .......... | ......C... | ...G...T.. | .......... |
| Eg-23(5) | .........T | .......... | T......... | .......... | ......C... | ...G...T.. | .......... |
| Eg-32(5) | .........T | .....A.... | .......... | .......... | ......C... | ...G...T.. | .......... |
| Eg-27(6) | .........T | .....A.... | .......... | .......T.. | ......C... | ...G...T.. | .......... |
| NL-26(7) | .........T | .....A.... | .......... | .......... | ......C... | ...G...T.. | .......... |
| Eg-30(8) | .........T | .....A.... | .......... | .......... | ......C... | ...G...T.. | .......... |
| Eg-15(9) | .........T | .....A.... | .......... | .......... | ......C... | ...G...T.. | .......... |
| Eg-1(10) | .........T | .....A.... | .......... | .......... | ......C... | ...G...T.. | .......... |
| Eg-22(10) | .........T | .....A.... | .......... | .......... | ......C... | ...G...T.. | .......... |
| Eg-24(10) | .........T | .....A.... | .......... | .......... | ......C... | ...G...T.. | .......... |
| Eg-25(10) | .........T | .....A.... | .......... | .......... | ......C... | ...G...T.. | .......... |

TO FIG. 13c.

| FIG. 13a. | FIG. 13b. |
|---|---|
| FIG. 13c. | FIG. 13d. |

| | | 23▶ AAAACAAACG | TAACACCAAC | CGTCGCCCAC | AGGACGTCAA | GTTCCCGGGT | GGGGGTCAGA | TCGTTGGTGG | 102▶ AGTTTACTTG |
|---|---|---|---|---|---|---|---|---|---|
| 1a | HCV-1 | .......... | .......... | .......... | .......... | .......... | .......... | .......... | .......... |
| 1b | HCV-J | .......C.. | .......... | .......C.. | .......... | .......C.. | .......T.. | .......... | .......C.. |
| 2a | HC-J6 | ...C....A. | .........A | ...TG..... | .....A.... | ......T... | .......C.. | .......C.. | .......A.. |
| 2b | HC-J8 | ...C....A. | .........A | ........C. | .........T | ......T... | .......... | .......C.. | .......... |
| 3a | Eb-1 | ...C...... | .........A | .......... | .......... | .......... | ......A... | .......... | ...A....G. |
|    | Eg-29(1) | .......... | .......... | ...C....CA | .........T | .......... | ......T.C. | .......C.. | .......... |
|    | Eg-33(2) | ...C...... | .......... | ...C....CA | .........T | .......... | ......T.C. | .......C.. | .......... |
|    | Eg-21(3) | .......... | .......... | ...C....CA | .........C | .......... | ......T... | .......C.. | .......... |

| | | 103▶ AAAACAAACG | TAACACCAAC | ATTGGGTGTG | CGCGCGACGA | GAAAGACTTC | CGACCGGTCG | CAACCTCGAG | 182▶ GTAGACGTCA |
|---|---|---|---|---|---|---|---|---|---|
| 1a | HCV-1 | .......... | .......... | .......... | .......... | .......... | .......... | .......... | .......... |
| 1b | HCV-J | .......... | .......... | .......G.. | .......T.. | .......G.. | .......T.. | .......T.. | ..A..G..A. |
| 2a | HC-J6 | .......C.. | .......C.. | .......G.. | .......A.. | .......G.. | ...G....T. | ...G..A..T | ..A..G..C. |
| 2b | HC-J8 | .......... | .......C.. | .......G.. | .......A.. | .......G.. | ...G....AC | ...G..G..T | ..AC....C. |
| 3a | Eb-1 | .......... | .......AC. | .......... | .......... | .......T.. | ...T..A... | .......G.. | ..AC....A. |
|    | Eg-29(1) | .......... | .......C.. | .......T.. | .......TC. | .......G.. | ...G...... | .......T.. | ..G.....C. |
|    | Eg-33(2) | .......... | .......C.. | .......G.. | .......TC. | .......G.. | ...G...... | .......T.. | ..G.....C. |
|    | Eg-21(3) | .......... | .......CC. | .......G.. | .......TG. | .......G.. | ...G...... | .......... | ..G.....G. |

TO FIG. 15b.

FROM FIG. 15a.

| | | 183▶ | | 203▶ | | 223▶ | | 243▶ | 262▶ |
|---|---|---|---|---|---|---|---|---|---|
| | | GCCTATCCCC | AAAGCTCGTC | GGCCCCGAGGG | CAGGACCTGG | GCTCAGCCCG | GGTACCCTTG | GCCCCTCTAT | GGCAATGAGG |
| 1a | HCV-1 | .......... | .......... | .......... | .......... | .......... | .......... | .......... | .......... |
| 1b | HCV-J | A......... | ....C..... | .......... | .......... | .......... | .......... | .......... | .......C.. |
| 2a | HC-J6 | ...C....T. | ...A...G.. | .CT...ACT. | ..AAT..... | GAA.A...A. | A...C..... | .A.C...... | .G.C...... |
| 2b | HC-J8 | ...C....G. | ...A...G.. | .CT...ACC. | ..A.T..... | GAA.A...A. | .A.T...... | .A.C...... | .A.C...... |
| 3a | Eb-29 | .......... | .......G.. | .AG..A.... | ...T...... | .......... | ...G...... | .......... | .......... |
| | Eg-29(1) | A......... | ...G..G... | .AT....... | ...A..T... | .A......A. | .A..T..... | ...T..T..C | .T..C..... |
| | Eg-33(2) | A......... | ...G..G... | .AT....... | ...A..T... | .A......A. | .A..T..... | ...T..T..C | .T..C..... |
| | Eg-21(3) | .......... | ...G..G... | .AT....... | ...A..T... | .A......A. | .ATT...A.. | .......... | .A.A------ |

| | | 5▶ | | 25▶ | | 45▶ | | 65▶ | 85▶ |
|---|---|---|---|---|---|---|---|---|---|
| | | PKPQKKNKRN | TNRRPQDVKF | PGGGQIVGGV | YLLPRRGPRL | GVRATRKTSE | RSQPRGRRQP | IPKARRPEGR | TWAQPGYPWP | LYGNE |
| 1a | HCV-1 | .......... | .......... | .......... | .......... | .......... | .......... | .......... | .......... | ..... |
| 1b | HCV-J | ....R.T... | .......... | .......... | .......... | .......... | .......... | ...D..ST.K | S.GK...... | ..... |
| 2a | HC-J6 | ....R.T... | .......... | .......... | .......... | .......... | .......... | ...D..ST.K | S.GK...... | ..... |
| 2b | HC-J8 | .......... | .I........ | .......... | .......V.. | .......... | .......... | .......... | S......... | ..... |
| 3a | Eb-1 | A...R.T... | .......M.. | .......... | .......... | ....C..... | .......... | .......S.. | S......... | ..... |
| | Eg-29,33 | ....R..... | .......T.. | .......... | .......... | .......... | .......... | .......S.. | S......... | ..... |
| | Eg-21 | .......... | .......... | .......... | .......... | ....G..... | .......... | .......S.. | S.....F... | ..... |

FIG. 15b.

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Hepatitis-C virus ( x i ) SEQUENCE DESCRIPTION: SEQ ID NO:1:

| Lys | Pro | Ala | Leu | Val | Pro | Asp | Lys | Glu | Val | Leu | Tyr | Gln | Gln | Tyr | Asp |
|---|---|---|---|---|---|---|---|---|---|---|---|---|---|---|---|
| 1 | | | | 5 | | | | | 10 | | | | | 15 | |

Glu Met ( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:2:

| Glu | Cys | Ser | Gln | Ala | Ala | Pro | Tyr | Ile | Glu | Gln | Ala | Gln | Val | Ile | Ala |
|---|---|---|---|---|---|---|---|---|---|---|---|---|---|---|---|
| 1 | | | | 5 | | | | | 10 | | | | | 15 | |

His Gln Phe ( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:3:

| Arg | Val | Val | Val | Thr | Pro | Asp | Lys | Glu | Ile | Leu | Tyr | Glu | Ala | Phe | Asp |
|---|---|---|---|---|---|---|---|---|---|---|---|---|---|---|---|
| 1 | | | | 5 | | | | | 10 | | | | | 15 | |

Glu Met ( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:4:

Arg Ala Val Ile Ala Pro Asp Lys Glu Val Leu Tyr Glu Ala Phe Asp
1               5                   10                  15

Glu Met ( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:5:

Glu Cys Ala Ser Lys Ala Ala Leu Ile Glu Glu Gly Gln Arg Met Ala
1               5                   10                  15

Glu Met Leu ( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:6:

Glu Cys Ala Ser Arg Ala Ala Leu Ile Glu Glu Gly Gln Arg Ile Ala
1               5                   10                  15

Glu Met Leu ( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:7:

Lys Pro Ala Ile Ile Pro Asp Arg Glu Val Leu Tyr Arg Glu Phe Asp
1               5                   10                  15

Glu Met ( 2 ) INFORMATION FOR SEQ ID NO:8:

( i ) SEQUENCE CHARACTERISTICS:
        ( A ) LENGTH: 18 amino acids
        ( B ) TYPE: amino-acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:8:

Lys Pro Ala Val Ile Pro Asp Arg Glu Val Leu Tyr Arg Glu Phe Asp
1               5                   10                  15

Glu Met ( 2 ) INFORMATION FOR SEQ ID NO:9:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:9:

Arg Pro Ala Val Xaa Pro Asp Arg Glu Val Leu Tyr Gln Glu Phe Asp
1               5                   10                  15

Glu Met ( 2 ) INFORMATION FOR SEQ ID NO:10:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:10:

Glu Cys Ser Gln His Leu Pro Tyr Ile Glu Gly Met Leu Ala Glu Gln
1               5                   10                  10

Phe ( 2 ) INFORMATION FOR SEQ ID NO: 11:

( i ) SEQUENCE CHARACTERISTICS:
    ( A ) LENGTH: 17 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Hepatitis-C virus ( x i ) SEQUENCE DESCRIPTION: SEQ ID NO:11:

```
Glu Cys Ser Gln His Leu Pro Tyr Ile Glu Gly Ala Leu Ala Glu Gln
1               5                  10                 10

Phe
```

( 2 ) INFORMATION FOR SEQ ID NO:12:

( i ) SEQUENCE CHARACTERISTICS:
        ( A ) LENGTH: 194 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:12:

```
NNNNNNNNN  CGAGTGTCGT  GCAGCCTCCA  GGMCYCCCCC  TCCCGGGAGA  GCCATAGTGG    60

TCTGCGGAAC  CGGTGAGTAC  ACCGGAATCG  CTGGGGTGAC  CGGGTCCTTT  CTTGGARCAA   120

CCCGCTCAAT  ACCCAGAAAT  TTGGGCGTGC  CCCCGCRAGA  YCACTAGCCG  AGTAGTGTTG   180

GGTCGCGAAA  GGCC                                                        194
```

( 2 ) INFORMATION FOR SEQ ID NO:13:

( i ) SEQUENCE CHARACTERISTICS:
        ( A ) LENGTH: 85 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: yes ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:13:

```
Xaa Xaa Xaa Xaa Xaa Xaa Xaa Xaa Xaa Xaa Glu Ile Tyr Gln Cys Cys
1               5                  10                 15

Asn Leu Glu Pro Glu Ala Arg Lys Val Ile Ser Ser Leu Thr Glu Arg
                20                 25                 30

Leu Tyr Cys Gly Gly Pro Met Phe Asn Ser Lys Gly Ala Gln Cys Gly
                35              40                 45
```

```
Tyr  Arg  Arg  Cys  Arg  Ala  Ser  Gly  Val  Leu  Pro  Thr  Ser  Phe  Gly  Asn
     50                  55                       60

Thr  Ile  Thr  Cys  Tyr  Ile  Lys  Ala  Thr  Ala  Ala  Cys  Xaa  Ala  Ala  Gly
65                       70                       75                       80

Leu  Arg  Asn  Pro  Asp
                    85
```

( 2 ) INFORMATION FOR SEQ ID NO:14:

( i ) SEQUENCE CHARACTERISTICS:
        ( A ) LENGTH: 57 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: yes ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:14:

```
Lys  Gln  Gln  Gly  Leu  Asn  Phe  Ser  Tyr  Leu  Xaa  Ala  Tyr  Gln  Ala  Thr
1                   5                        10                       15

Val  Cys  Ala  Arg  Ala  Gln  Ala  Xaa  Pro  Pro  Ser  Trp  Asp  Glu  Xaa  Trp
               20                  25                       30

Lys  Cys  Leu  Val  Arg  Leu  Lys  Pro  Thr  Leu  His  Gly  Pro  Thr  Pro  Leu
               35                  40                       45

Leu  Tyr  Arg  Leu  Gly  Pro  Val  Gln  Asn
          50                  55
```

( 2 ) INFORMATION FOR SEQ ID NO:15:

( i ) SEQUENCE CHARACTERISTICS:
        ( A ) LENGTH: 124 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: yes ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:15:

```
Ala  Lys  Pro  Gln  Arg  Lys  Thr  Lys  Arg  Asn  Thr  Ile  Arg  Arg  Pro  Gln
1                   5                        10                       15

Asp  Val  Lys  Phe  Pro  Gly  Gly  Gly  Gln  Ile  Val  Gly  Gly  Val  Tyr  Val
               20                  25                       30

Leu  Pro  Arg  Arg  Gly  Pro  Arg  Leu  Gly  Val  Cys  Ala  Thr  Arg  Lys  Thr
               35                  40                       45

Ser  Glu  Arg  Ser  Gln  Pro  Arg  Gly  Arg  Arg  Gln  Pro  Ile  Pro  Lys  Ala
          50                  55                       60

Arg  Arg  Ser  Glu  Gly  Arg  Ser  Trp  Ala  Gln  Pro  Gly  Tyr  Pro  Trp  Pro
65                       70                       75                       80

Leu  Tyr  Gly  Asn  Glu  Gly  Cys  Gly  Trp  Ala  Gly  Trp  Leu  Leu  Ser  Pro
                    85                       90                       95

Arg  Gly  Ser  Arg  Pro  Ser  Trp  Gly  Pro  Asn  Asp  Pro  Arg  Arg  Arg  Ser
```

```
                    100                          105                          110
       Arg  Asn  Leu  Gly  Lys  Val  Ile  Asp  Thr  Leu  Thr  Trp
                         115                          120
```

( 2 ) INFORMATION FOR SEQ ID NO:16:

( i ) SEQUENCE CHARACTERISTICS:
        ( A ) LENGTH: 367 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:16:

```
NNNNCACCCY  RUCRCRAAAU  ACVUCAUGGC  AUGYAUGUCA  GCUGAUCUGG  AAGUAACCAC    60
CAGCACCUGG  GUGUUGCUUG  GAGGRGUCCU  CGCKGCCCUA  GCGGCCUACU  GCUUGCAGU    120
CGGCUGCGUU  GUGAUUGUGG  GYCAUAUUGA  GCUGGGRGGC  AAGCCVGCAM  UCGUUCCAGA   180
CAARGARGUG  UUGUAUCAAC  AAUACGAUGA  GAUGGAGGAG  UGCUCGCAAG  CYGCCCCAUA   240
UAUCGAACAA  GCUCARGURA  UAGCCCACCA  GUUCAAGGAG  AAAGUCCUUG  GRUUGCUGCA   300
GCGRGCCACC  CAACAACARG  CUGUYAUUGA  GCCMAUAGUA  GCUACCAACU  GGCAAAANNN   360
NNNNNNN                                                                 367
```

( 2 ) INFORMATION FOR SEQ ID NO:17:

( i ) SEQUENCE CHARACTERISTICS:
        ( A ) LENGTH: 128 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: yes ( v ) FRAGMENT TYPE: internal ( v i ) ORIGINAL SOURCE:
        ( A ) ORGANISM: Hepatitis-C virus ( x i ) SEQUENCE DESCRIPTION: SEQ ID NO:17:

```
Xaa  His  Pro  Xaa  Xaa  Lys  Tyr  Xaa  Met  Ala  Cys  Met  Ser  Ala  Asp  Leu
1                   5                        10                       15
Glu  Val  Thr  Thr  Ser  Thr  Trp  Val  Leu  Leu  Gly  Gly  Val  Leu  Ala  Ala
               20                       25                       30
Leu  Ala  Ala  Tyr  Cys  Leu  Ser  Val  Gly  Cys  Val  Val  Ile  Val  Gly  His
               35                       40                       45
Ile  Glu  Leu  Gly  Gly  Lys  Pro  Ala  Xaa  Val  Pro  Asp  Lys  Glu  Val  Leu
     50                       55                       60
Tyr  Gln  Gln  Tyr  Asp  Glu  Met  Glu  Glu  Cys  Ser  Gln  Ala  Ala  Pro  Tyr
65                            70                       75                  80
Ile  Glu  Gln  Ala  Gln  Val  Ile  Ala  His  Gln  Phe  Lys  Glu  Lys  Val  Leu
                    85                       90                       95
Gly  Leu  Leu  Gln  Arg  Ala  Thr  Gln  Gln  Gln  Ala  Val  Ile  Glu  Pro  Ile
                    100                      105                      110
```

| Val | Ala | Thr | Asn | Trp | Gln | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|-----|
| | 115 | | | | | 120 | | | | | | 125 | | | |

( 2 ) INFORMATION FOR SEQ ID NO:18:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:18:

| TGAGTGTYGT | RCAGCCTCCA | GGAYYCCCCC | NNNNNNNNNN | NNNNNNNNNN | NNNNNNNNNN | 60 |
| CGGTGAGTWC | ACCGGAATCG | CCGGGAYGAC | CGGGTCCTTT | CTTGGANNHW | ACCCGCTCMA | 120 |
| TGCCCGGAAA | TNNNNNNNNN | NNNNNGCRAG | ACYGCTAGCC | GAGTAGTGTT | GGGTCGC | 177 |

( 2 ) INFORMATION FOR SEQ ID NO:19:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:19:

| AAACCAAAAG | AAACACCATC | CGTCGCCCAC | AGGACGTCAA | GTTCCGGGT | GGCGGACAGA | 60 |
| TCGTTGGTGG | AGTATACGTG | TTGCCGCGCA | GGGGCCCACG | ATTGGGTGTG | TGCGCGACGC | 120 |
| GTAAAACTTC | TGAACGGTCA | CAGCCTCGCG | GACGACGACA | GCCTATCCCC | AAAGCGCGTC | 180 |
| GGAGCGAAGG | CAGGTCCTGG | GCTCAGCCCG | GGTACCCGTG | GCCCCTCTAT | GGTAACGAGG | 240 |

( 2 ) INFORMATION FOR SEQ ID NO:20:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:20:

| NNNNNNNNNN | TAACACCAAC | CGCCGCCCCA | YGGACGTTAA | GTTCCGGGT | GGTGGYCAGA | 60 |
| TCGTTGGCGG | AGTTTACTTG | TTGCCGCGCA | GGGGCCCYMG | KTTGGGTGTG | CGCGCGACTS | 120 |

GRAAGACTTC GGAGCGGTCG CAACCTCGTG GGAGACGYCA RCCTATCCCM AAGGCGCGTC    180

GATCCGAGGG AAGGTCCTGG GCACARCCAG GATWTCCATG NNNNNNNNNN NNNNNNNNNN    240

(2) INFORMATION FOR SEQ ID NO:21:

(i) SEQUENCE CHARACTERISTICS:
        (A) LENGTH: 82 amino acids
        (B) TYPE: amino acid
        (C) STRANDEDNESS:
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: Hepatitis-C virus (xi) SEQUENCE DESCRIPTION: SEQ ID NO:21:

```
Xaa Xaa Xaa Xaa Lys Arg Asn Thr Asn Arg Arg Pro Xaa Asp Val Lys
 1               5                  10                  15
Phe Pro Gly Gly Gly Gln Ile Val Gly Gly Val Tyr Leu Leu Pro Arg
            20                  25                  30
Arg Gly Pro Arg Leu Gly Val Arg Ala Thr Xaa Lys Thr Ser Glu Arg
        35                  40                  45
Ser Gln Pro Arg Gly Arg Arg Gln Pro Ile Pro Lys Ala Arg Arg Ser
    50                  55                  60
Glu Gly Arg Ser Trp Ala Gln Pro Gly Xaa Pro Trp Pro Leu Tyr Xaa
65                  70                  75                  80
Xaa Xaa
```

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA
            oligonucleotide"

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO:22:

ATACTCGAGG TGCACGGTCT ACGAGACCT    29

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA
            oligonucleotide"

(iii) HYPOTHETICAL: NO ( i v ) ANTI-SENSE: NO ( v i ) ORIGINAL SOURCE:
    ( A ) ORGANISM: Hepatitis-C virus ( x i ) SEQUENCE DESCRIPTION: SEQ ID NO:23:

CACTCTCGAG CACCCTATCA GGCAGT 26

( 2 ) INFORMATION FOR SEQ ID NO:24:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
    ( A ) ORGANISM: Hepatitis-C virus ( x i ) SEQUENCE DESCRIPTION: SEQ ID NO:24:

CTGTGAGGAA CTACTGTCTT 20

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
    ( A ) ORGANISM: Hepatitis-C virus ( x i ) SEQUENCE DESCRIPTION: SEQ ID NO:25:

TTCACGCAGA AAGCGTCTAG 20

( 2 ) INFORMATION FOR SEQ ID NO:26:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
    ( A ) ORGANISM: Hepatitis-C virus ( x i ) SEQUENCE DESCRIPTION: SEQ ID NO:26:

ATGTACCCCA TGAGGTCGGC 20

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA oligonucleotide"

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO:27:

AGGTCTCGTA GACCGTGCAT CATGAGCAC 29

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA oligonucleotide"

(iii) HYPOTHETICAL: NO (vi) ORIGINAL SOURCE:
        (A) ORGANISM: Hepatitis-C virus (xi) SEQUENCE DESCRIPTION: SEQ ID NO:28:

CCGGCATGCA TGTCATGATG TAT 23

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA oligonucleotide"

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO:29:

GTATTGGTG ACTGGGTGCG TC 22

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "synthetic DNA oligonucleotide"

(iii) HYPOTHETICAL: NO (iv) ANTI-SENSE: NO (vi) ORIGINAL SOURCE:
    (A) ORGANISM: Hepatitis-C virus (xi) SEQUENCE DESCRIPTION: SEQ ID NO:30:

TCTTGAATTT TGGGAGGGCG TCTT    24

(2) INFORMATION FOR SEQ ID NO:31:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA oligonucleotide"

(iii) HYPOTHETICAL: NO (iv) ANTI-SENSE: NO (vi) ORIGINAL SOURCE:
    (A) ORGANISM: Hepatitis-C virus (xi) SEQUENCE DESCRIPTION: SEQ ID NO:31:

CATATAGATG CCCACTTCCT ATC    23

(2) INFORMATION FOR SEQ ID NO:32:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA oligonucleotide"

(iii) HYPOTHETICAL: NO (iv) ANTI-SENSE: NO (vi) ORIGINAL SOURCE:
    (A) ORGANISM: Hepatitis-C virus (xi) SEQUENCE DESCRIPTION: SEQ ID NO:32:

AACTCGAGTA TCCCACTGAT GAAGTTCCAC AT    32

(2) INFORMATION FOR SEQ ID NO:33:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA oligonucleotide"

(iii) HYPOTHETICAL: NO (iv) ANTI-SENSE: NO (v i) ORIGINAL SOURCE:
  (A) ORGANISM: Hepatitis-C virus (x i) SEQUENCE DESCRIPTION: SEQ ID NO:33:

CACATGTGCT TCGCCCAGAA               20

(2) INFORMATION FOR SEQ ID NO:34:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "synthetic DNA
        oligonucleotide"

(i i i) HYPOTHETICAL: NO (i v) ANTI-SENSE: NO (v i) ORIGINAL SOURCE:
    (A) ORGANISM: Hepatitis-C virus (x i) SEQUENCE DESCRIPTION: SEQ ID NO:34:

GGACCTACGC CCCTTCTATA               20

(2) INFORMATION FOR SEQ ID NO:35:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "synthetic DNA
        oligonucleotide"

(i i i) HYPOTHETICAL: NO (i v) ANTI-SENSE: NO (v i) ORIGINAL SOURCE:
    (A) ORGANISM: Hepatitis-C virus (x i) SEQUENCE DESCRIPTION: SEQ ID NO:35:

TCGGTTGGGG CCTGTCCAAA ATG           23

(2) INFORMATION FOR SEQ ID NO:36:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "synthetic DNA
        oligonucleotide"

(i i i) HYPOTHETICAL: NO (i v) ANTI-SENSE: NO (v i) ORIGINAL SOURCE:
    (A) ORGANISM: Hepatitis-C virus (x i) SEQUENCE DESCRIPTION: SEQ ID NO:36:

GGTCCCACCC CTCTCCTGTA               20

( 2 ) INFORMATION FOR SEQ ID NO:37:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:37:

CCGCTTGGGT TCCGTTACCA ACG        23

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:38:

GGGCCAACAC CCCTGCTATA        20

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:39:

CAGACTGGGC GCCGTTCAGA ATG        23

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (v i) ORIGINAL SOURCE:
        (A) ORGANISM: Hepatitis-C virus (x i) SEQUENCE DESCRIPTION: SEQ ID NO:40:

```
GGCGGAATTC CTGGTCATAG CCTCCGTGAA                                    30
```

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (v i) ORIGINAL SOURCE:
        (A) ORGANISM: Hepatitis-C virus (x i) SEQUENCE DESCRIPTION: SEQ ID NO:41:

```
CCACGACTAG ATCATCTCCG                                               20
```

(2) INFORMATION FOR SEQ ID NO:42:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (v i) ORIGINAL SOURCE:
        (A) ORGANISM: Hepatitis-C virus (x i) SEQUENCE DESCRIPTION: SEQ ID NO:42:

```
TGGGGATCCC GTATGATACC CGCTGCTTTG A                                  31
```

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (vi) ORIGINAL SOURCE:
    (A) ORGANISM: Hepatitis-C virus (xi) SEQUENCE DESCRIPTION: SEQ ID NO:43:

CTCAACCGTC ACTGAACAGG ACAT                                              24

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA oligonucleotide"

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO:44:

GCCGCCCCAT ATATCGAACA                                                   20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA oligonucleotide"

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO:45:

GCTCAGGTAA TAGCCCACCA                                                   20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA oligonucleotide"

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO:46:

AAAGCCGCCC TCATTGAGGA                                                   20

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:47:

GGGCAGCGGA TGGCGGAGAT                                                                 20

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:48:

CACTTACCGT ACATCGAGCA                                                                 20

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA oligonucleotide"

( i i i ) HYPOTHETICAL: NO ( i v ) ANTI-SENSE: NO ( v i ) ORIGINAL SOURCE:
        ( A ) ORGANISM: Hepatitis-C virus ( x i ) SEQUENCE DESCRIPTION: SEQ ID NO:49:

GGGATGATGC TCGCCGAGCA                                                                 20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (v i) ORIGINAL SOURCE:
        (A) ORGANISM: Hepatitis-C virus (x i) SEQUENCE DESCRIPTION: SEQ ID NO:50:

CAYGTRAGGG TATCGATGAC        20

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (v i) ORIGINAL SOURCE:
        (A) ORGANISM: Hepatitis-C virus (x i) SEQUENCE DESCRIPTION: SEQ ID NO:51:

ACTGCCTGAT AGGGTGCTTG CGAG        24

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (v i) ORIGINAL SOURCE:
        (A) ORGANISM: Hepatitis-C virus (x i) SEQUENCE DESCRIPTION: SEQ ID NO:52:

AGGTCTCGTA GACCGTGCAT CATG        24

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "synthetic DNA oligonucleotide"

(i i i) HYPOTHETICAL: NO (i v) ANTI-SENSE: NO (vi) ORIGINAL SOURCE:
  (A) ORGANISM: Hepatitis-C virus (xi) SEQUENCE DESCRIPTION: SEQ ID NO:53:

TTGCGBGACC TWCGCCGGGG GTC    23

HEPATITIS-C VIRUS TESTING

TECHNICAL FIELD

This application is a 371 of PCT/GB92/02143 filed Nov. 20, 1992, published as WO93/10239 May 27, 1993.

The present invention relates to the discovery of new types of hepatitis C virus, that we have termed type 3 (HCV-3) and type 4 (HCV-4). In particular, it relates to the etiologic agent of hepatitis C virus type 3 and 4, and to polynucleotides and immunoreactive polypeptides which are useful in immunoassays for the detection of HCV-3 and HCV-4 in biological samples; and also to the use of antigenic HCV-3 and HCV-4 specific polypeptides in vaccines.

BACKGROUND OF THE INVENTION

Acute viral hepatitis is a disease which may result in chronic liver damage. It is clinically diagnosed by a well-defined set of patient symptoms, including jaundice, hepatic tenderness, and an increase in the serum levels of alanine aminotransferase and aspartate aminotransferase. Serologic immunoassays are generally performed to diagnose the specific type of viral causative agent. Historically, patients presenting with symptoms of hepatitis and not otherwise infected by hepatitis A, hepatitis B, Epstein-Barr or cytomegalovirus were clinically diagnosed as having non-A, non-B hepatitis (NANBH) by default.

For many years, the agent of non-A, non-B hepatitis remained elusive. It has now been established that many cases of NANBH are caused by a distinct virus termed hepatitis C virus (HCV). European Patent Application EP-A-0318216 discloses CDNA sequences derived from HCV, polynucleotide probes and polypeptides for use in immunoassays. Further information is provided in European Application EP-A-0388232.

The HCV genome encodes a large polyprotein precursor, which contains structural and non-structural regions. The single protein is apparently cleaved into a variety of proteins after production. Most of the structural and non-structural proteins have now been identified from in vitro RNA translation and expression as recombinant proteins. The C and E regions encode for nucleocapsid structural proteins and for envelope structural proteins, respectively. At least five additional regions follow, which encode for non-structural (NS) protein of undefined function. The organisation is believed to be as follows (A. Alberti, Journal of Hepatology, 1991; 12; 279 to 282)

```
5'                                                    3'
NCR: C : E1 : E2 : NS1 : NS2 : NS3 : NS4 : NS5
```

Certain immunoreactive proteins have been described as recombinant proteins, for example C22 (in the core region), C33 (in NS3 region), 5-1-1 and C100 (both in the NS4 region), and NS5 (NS5 region). Diagnosis of hepatitis C is still largely based on methods which detect antibodies against the product of the C-100 clone. This clone was ligated with overlapping clones to produce a larger viral antigen (C100) corresponding to part of the NS3-NS4 genomic region. C100 was then fused with the human superoxide dismutase (SOD) gene, expressed in use as a large recombinant fusion protein (C100-3) and used on solid phase to develop radio-labelled (RIA) and enzyme-linked immunosorbent assays (ELISA).

Polynucleotides useful for screening for HCV are disclosed in European Patent Specification EP-A-0398748. European Patent Specification EP-A-0414475 purports to disclose the propagation of HCV in culture cells and the production of antigens for use in diagnostics. European Patent Specification EP-A-0445423 discloses an improved immunoassay for detecting HCV antibodies.

Blood banks in the United Kingdom have recently begun routine testing of blood donors for antibodies to components of HCV. One assay involves the detection of HCV antibodies to C100-3 polypeptides. The C100-3 antibody recognises a composite polyprotein antigen within non-structural regions of the virus and is a consistent marker of HCV infection. However, in acute infections this antibody is unreliable because of the delay (typically 22 weeks) in seroconversion after exposure. Furthermore, the C100-3 antibody test lacks specificity for the hepatitis C virus.

Second generation antibody tests employ recombinant antigens or synthetic linear peptides representing structural antigens from the highly conserved core region of the virus as well as non-structural antigens. However, it is found that some second-generation ELISA tests can yield false-positive reactions. The recombinant immunoblot assay (RIBA-2) incorporating four antigens from the HCV genome, provides a method for identifying genuine-anti-HCV reactivity. However, the result can be "indeterminate." The present workers have reported (The Lancet, 338; Oct. 19, 1991) varying reactivity of HCV-positive blood donors to 5-1-1, C100, C33C and C22 antigens, and compared these with the results of the direct detection of HCV RNA present in the blood samples using polymerase chain reaction (PCR) to amplify HCV polynucleotides. However, the work demonstrates that the unambiguous diagnosis of HCV infections is not yet possible.

Recently there has been discovered a second type of HCV (References 1, 2) called K2 that differs considerably in sequence from the published prototype (Reference 3) or the first type K1 sequences (References 4 and 5).

SUMMARY OF THE INVENTION

The present invention is based on the discovery of previously unknown type 3 and 4 variants of HCV, by a comparison to sequences amplified by PCR in certain regions of the HCV genome and confirmed by phylogenetic analysis. The invention has thus identified polynucleotide sequences and peptides which are HCV-3 and HCV-4 specific. These may be used to diagnose HCV-3 and HCV-4 infection and should thus be included in any definitive test for HCV infection.

One aspect of the invention provides polynucleotide sequences unique to hepatitis C virus types 3 and 4 (HCV-3 and HCV-4). The sequences may be RNA or DNA sequences. In principal any HCV-3 or HCV-4 specific polynucleotide sequence from non-coding, core, E1, E2 or NS1-5 genome regions can be used as a hybridisation probe. The sequences may be recombinant (i.e. expressed in transformed cells) or synthetic and may be comprised within longer sequences if necessary. Equally, deletions, insertions or substitutions may also be tolerated if the polynucleotide may still function as a specific probe. Polynucleotide sequences such as core, NS3, NS4 and NS5 which code for antigenic peptides are particularly useful.

Another aspect provides an antigenic HCV-3 or HCV-4 specific peptide, particularly from the core, NS3, NS4 or NS5 regions (e.g. the HCV-3 or HCV-4 counterparts of C100 peptide, 5-1-1 peptide, C33 peptide or C22 peptide or epitopes thereof) or peptides including these antigens.

The peptide may be a fusion peptide which comprises at least two of the antigenic HCV-3 or HCV-4 specific peptides. A fusion peptide may also comprise at least one of the antigenic peptides fused to β-galactosidase, GST, trpE, or polyhedrin coding sequence.

A further aspect of the invention provides labelled antigenic HCV-3 or HCV-4 specific peptide (or mixtures thereof, particularly from the core and NS4 regions) for use in an immunoassay.

A further aspect of the invention provides antibodies to HCV-3 or HCV-4 specific antigens, particularly monoclonal antibodies for use in therapy and diagnosis. Thus labelled antibodies may be used for in vivo diagnosis. Antibodies carrying cytotoxic agents may be used to attack HCV-3 or HCV-4 infected cells.

A further aspect of the invention provides a vaccine comprising immunogenic HCV-3 or HCV-4 specific peptide.

The HCV-3 or HCV-4 specific polynucleotide sequences may be used for identification of the HCV virus itself (usually amplified by PCR) by hybridisation techniques.

Oligonucleotides corresponding to variable regions in the NS-4 region could be used for type-specific PCR. Outer sense and inner sense primers may be used in combination with the two conserved anti-sense primers for a specific detection method for HCV types 1, 2, 3 and 4.

Immunoreactive HCV-3 or HCV-4 specific peptides (particularly from the core and NS4 regions) may be used to detect HCV-3 and HCV-4 antibodies in biological samples, and may also provide the basis for immunogens for inclusion in vaccines (especially the E1 polypeptide). The term "peptide" is used herein to include epitopic peptides having the minimum number of amino acid residues for antigenicity, oligopeptides, polypeptides and proteins. The peptide may be a recombinant peptide expressed from a transformed cell, or could be a synthetic peptide produced by chemical synthesis.

In particular, the invention allows blood donor screening by conventional assays (using HCV type 1 encoded antigens) to be supplemented with a second test that contains two oligopeptides corresponding to first and second antigenic regions found in the NS-4 sequence of HCV type 3 (positions 1691 to 1708; sequence KPALVPDKEVLYQQY-DEM (SEQ ID NO:1) and positions 1710 to 1728; sequence ECSQAAPYIEQAQVIAHQF (SEQ ID NO:2)) and two derived from the equivalent regions of HCV type 2, R(A/V)V(V/I)(A/T)PDKE(I/V)LYEAFDEM (SEQ ID NO:3 or 4) and ECAS(K/R)AALIEEGQR(M/I)AEML (SEQ ID NO:5 or 6).

The corresponding HCV-4 antigens from substantially positions 1691 to 1708 and 1710 to 1728 may be used for HCV-4 detection.

Thus, the present invention has also identified corresponding polynucleotide and peptide sequences which may be used to identify hepatitis C type 2 viral infection.

Production and detection of the antigen-antibody immune complex may be carried out by any methods currently known in the art. For example, a labelling system such as enzyme, radioisotope, fluorescent, luminescent or chemiluminescent labels may be employed, usually attached to the antigen. Labelled anti-antibody systems may also be used. The recombinant antigen may be either used in liquid phase or absorbed onto a solid substrate.

Oligopeptides corresponding to the antigenic regions of all three major types may also be used separately to serologically distinguish individuals infected with different HCV types. Such an assay could be in the format of an indirect enzyme immunoassay (EIA) that used sets of wells or beads coated with peptides of the two major antigenic regions for HCV types 4, 3 (SEQ ID NO:1 or 2) and 2 (SEQ ID NO:3, 4, 5 or 6), and with type 1 (KPA(V/I)IPDREVLYREFDEM (SEQ ID NO:7 or 8) and RPAV(I/V)PDREVLYQEFDEM (SEQ ID NO:9) and ECSQHLPYIEG(M/A)AEQF) (SEQ ID NO: 10 or 11). Minor degrees of cross-reactivity, should they exist, can be absorbed out by dilution of the test serum in a diluent that contained blocking amounts of soluble heterologous-type oligopeptides, to ensure that only antibody with type-specific antibody reactivity bound to the solid phase.

Immunogens for use in vaccine formulations may be formulated according to techniques currently known in the art, including the use of suitable adjuvant and immune-stimulation systems.

Furthermore, the present invention also encompasses assay devices or kits including peptides which contain at least one epitope of HCV-3 or HCV-4 antigen (or antibodies thereto), as well as necessary preparative reagents, washing reagents, detection reagents and signal producing reagents. The antigen may be from the core or NS4 regions. The assay device may be in the form of a plate having a series of locations respectively containing HCV-1, HCV-2, HCV-3, and optionally HCV-4, specific antigens.

The invention also provides a method of in vitro testing for HCV which comprises reverse transcribing any HCV polynucleotide present and amplifying by polymerase chain reaction (PCR), and detecting the amplified HCV polynucleotide employing an HCV-2, HCV-3 or HCV-4 specific polynucleotide probe.

The invention further provides a method of in vitro HCV typing which comprises
carrying out endonuclease digestion of an HCV-containing sample employing ScrFI or HaeIII/RsaI endonuclease; and
comparing the restriction patterns with characteristic type-specific patterns.

The endonuclease digestion may also employ HinfI in a separate or the same digestion.

The invention furthermore provides a method of in vitro HCV typing which comprises
carrying out endonuclease digestion of an HCV-containing sample employing ScrFI endonuclease, the restriction pattern being characteristic of HCV-1, HCV-2 and HCV-3;
carrying out endonuclease digestion employing HinfI endonuclease, the restriction pattern being characteristic of HCV-4.

DESCRIPTION OF THE DRAWINGS

Examples of the invention will now be described by way of example only.

FIGS. 1(a) to 1(h) give cDNA sequences obtained from PCR amplification of a region −255 to −62 of the 5' non-coding region of HCV samples from 18 blood donors and a comparison with previously published nucleotide sequences (see Table 2); sequence numbering corresponding to the prototype HCV-1 sequence (ref.4) and previous designations of type 1 or 2 being indicated: samples E-b1 through E-b8 represent HCV-3 sequences (SEQ ID NO: 12);

FIG. 3 is a comparison of deduced amino acid sequences in the NS-5 region of blood donors (E-b1, E-b2, E-b3, E-b7 (type 3) (SEQ ID NO:13) and E-b12 (type 2) with those previously published (Table 2). Amino acid residue numbering follows that of the HCV-1 polyprotein (4) and uses single letter amino acid codes:

FIG. 5 is a comparison of deduced amino acid sequences in the NS-3 region of blood donors (E-b1, E-b2, E-b6, E-b7 (type 3) (SEQ ID NO: 14) with those previously published (Table 2). Group 1/1: amino acid sequence of f1, f3, f4, f5, h2, h3, h4 (one), i2, i3, i4, p1, p2; Group 1/2: amino acid sequence of i5; Group 1/3: amino acid sequence of h2, h3, h4 (one), h5, f2, p3, i1; Group 1/4: amino acid sequence of h1 (one); Group 1/5: amino acid sequence of h1 (one). Numbering, symbols and abbreviations are as described for FIG. 3;

FIG. 7(a) and 7(b) are a comparison of deduced amino acid sequences in the core region of blood donor E-b1 (type 3) (SEQ ID NO: 15) with those previously published (Table 2). Numbering, symbols and abbreviations are as described for FIG. 3;

FIGS. 9(a) and 9(b) (SEQ ID NO: 16) show nucleotide, and FIG. 9(c) (SEQ ID NO: 17) shows deduced amino acid sequences of HCV type 3 variants amplified from 5 Scottish blood donors (nos. 40, 38, 36, 26 and 1787) in the putative NS-4 region of HCV (nucleotides and amino acid residues numbered as in Choo et al., (1991). Nucleotide codes: G: guanidine; C: cytidine; A: adenine; U: uridine; amino acid codes: A: alanine; R: arginine; N: asparagine; D: aspartic acid; C: cysteine; Q: glutamine; E: glutamic acid; G: glycine; H: histidine; I: isoleucine; L: leucine; K: lysine; M: methionine; F: phenylalanine: P: proline; S: serine; T: threonine; W: trytophan; Y: tyrosine; V: valine.".": sequence not determined; difference from consensus shown in bold.

FIG. 10(a) shows a comparison of amino acid sequences between residues 1679 and 1768 (Choo et al., 1991) of the three major variants of HCV. T16, T42, T77, T1801, T1825: Scottish blood donors infected with HCV type 1; T351: Scottish blood donor infected with HCV type 2: T59, T940, T810: Scottish blood donors infected with HCV type 2: T40, T38, T36, T26, T1787: Scottish blood donors infected with HCV type 3 (residues 42 to 128 of SEQ ID NO: 17); and FIG. 10(b) shows the derivation of consensus sequences for HCV types 3 (residues 42 to 128 of SEQ ID NO: 17), 2 and 1 oligopeptide series. Differences from consensus shown in bold. Amino acid codes: A: alanine; R: arginine; N: asparagine; D: aspartic acid; C: cysteine; Q: glutamine; E: glutamic acid; G: alycine; H: histidine; I: isoleucine; L: leucine; K: lysine; M: methionine; F: phenylalanine; P: proline; S: serine; T: threonine; W: tryptophan; Y: tyrosine; V: valine; ".": not determined.

FIGS. 11(a) to (11f) show amino acid sequences of nonameric oligopeptides used for epitope mapping, derived from consensus HCV type 3 (residues 42 to 128 of SEQ ID NO: 17), type 2 and type 1 sequences respectively. Amino acid codes: A: alanine; R: arginine; N: asparagine; D: aspartic acid; C: cysteine; Q: glutamine; E: glutamic acid; G: glycine; H: histidine; I: isoleucine; L: leucine; K: lysine; M: methionine; F: phenylalanine; P: proline; S: serine; T: threonine; W: tryptophan; Y: tyrosine; V: valine;

FIGS. 13(a) to 13(c) are a comparison of divergent HCV sequences with representative type 1, 2 and 3 (SEQ ID NO: 18) sequences in variable regions of the 5'NCR. Sequences from –255 to –246, –215 to –186, –115 to –102 and –69 to –62 identical to prototype sequence. ".": sequence identity with HCV-1; ".": gap introduced in sequences to preserve alignment; "–": sequence not determined. Origins of sequences : Eg- 1–33: Egypt; NL-26: Holland; HK- 1–4: Hong Kong; IQ-48: Iraq; XX-96: xxxxx. Figures in parentheses number each non-identical sequence.

(FIG. 1). Hollow squares are published sequences from Zaire; Hollow small circles are sequences from South Africa; Hollow small solid circles are sequences obtained elsewhere in the world.

FIGS. 15(a) and 15(b) are a comparison of HCV types 1, 2, 3 (SEQ ID NO: 19) and 4 (SEQ ID NO: 20) nucleotide (A) and HCV types 1, 2, 3 (residues 1 to 89 of SEQ ID NO: 15) and 4 (SEQ ID NO: 21) amino acid (B) sequences in the core region. Symbols as for FIG. 13. Single letter amino acid codes are used;

I) ANALYSIS OF HEPATITIS C VIRUS AND PHYLOGENETIC RELATIONSHIP OF TYPES 1, 2 and 3

Introduction

Sequence analysis of the 5' non coding region of hepatitis C virus (HCV) amplified from the plasma of individuals infected in Britain revealed the existence of three distinct groups of HCV, differing by 9–14% in nucleotide sequence. Two of the groups identified were similar to those of HCV variants previously termed type 1 and type 2, while the third group appeared to represent a novel virus type. Sequence comparisons were then made between the three virus types in other regions of the viral genome. In the NS-5 region, a high degree of nucleotide and amino acid sequence diversity was observed, with samples classified here as type "3" (SEQ ID NO: 13) again forming a distinct group that was phylogenetically distinct from type 1 and type 2 variants. Type 3 sequences were similarly differentiated in the NS-3 (SEQ ID NO: 14) and core (SEQ ID NO: 15 and 19) regions from HCV type 1 sequences. The designation of virus types, including an observed sub-division of type 1 sequences into geographically distinct variants is discussed in relation to the new sequence data obtained in this study.

Discussion

Replication of nucleotide sequences by polymerase chain reaction (PCR) is a recently established technique. Synthetic complementary primer sequences are hybridised to single-stranded DNA on either side of a genome region to be copied. The second strand is built up under the action of a heat-stable polymerase in the region between the primers. Heating then dissociates the two-strands and the replication process starts again. The PCR technique allows tiny amounts of polynucleotide to be amplified provided that there is sufficient sequence information to synthesise the primer sequences.

The major problem associated with the use of the PCR to assess sequence variation using the PCR is the possibility that mismatches between the primers and the variant sequence will prevent amplification. We have used several strategies to overcome this problem. For initial virus detection, we used primers in the 5'NCR, which are reported to be highly conserved amongst type 1 variants (4, 11, 13, 16, 23, 24, 26, 33), and between K1 and K2 (23). Sequence analysis of the blood donors allowed the identification of type 1 and type 2 variants by comparison with published sequence data. This analysis also revealed the existence of a third "type" of HCV (SEQ ID NO: 12) that appeared to be as distinct from type 1 as type 2 was (FIGS. 1, 2; Table 3). Based on our initial tentative classification, we sought corroboration of our findings in other (coding) and more variable regions of the viral genome.

Figure 4:
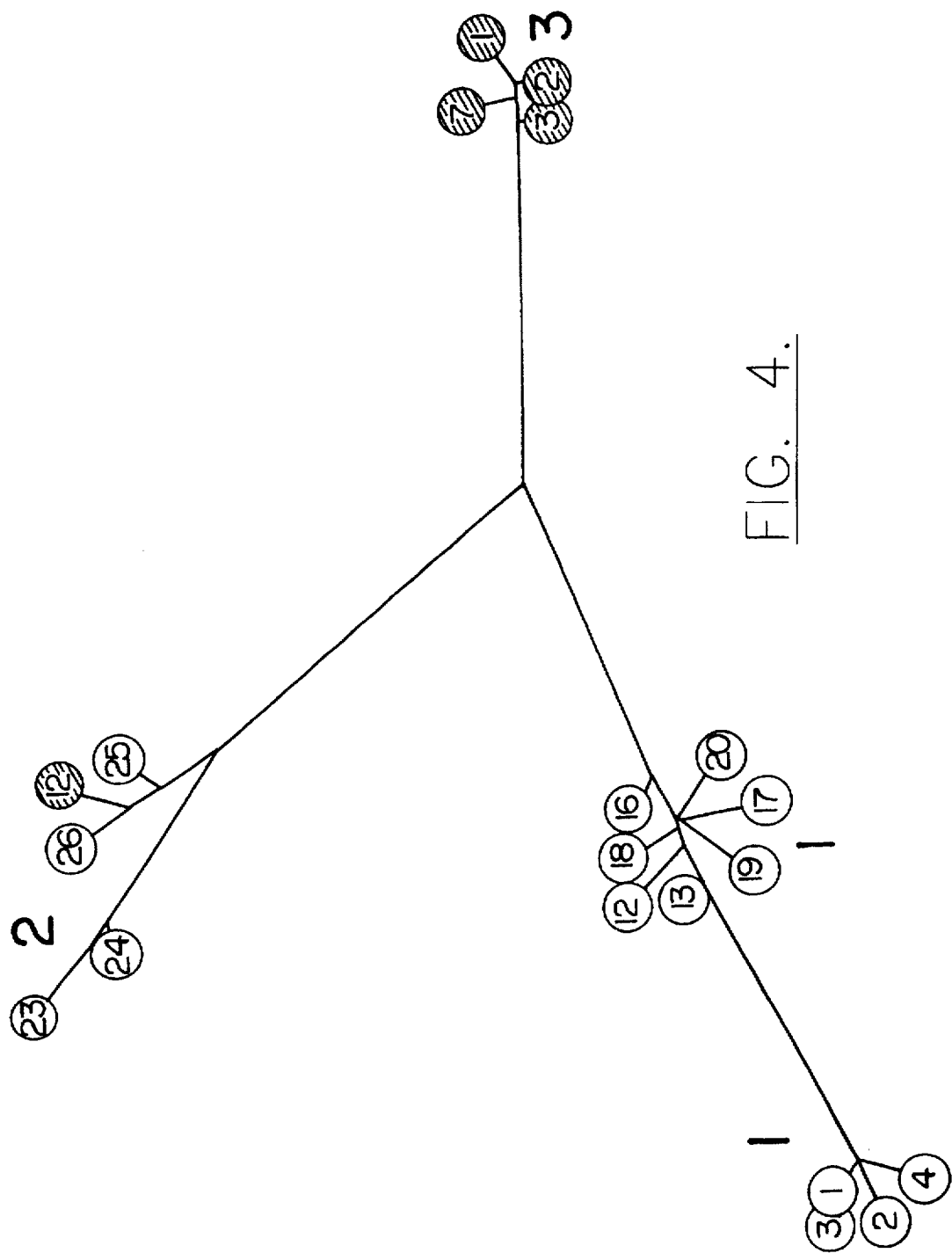
FIG. 4 is a phylogenetic analysis of the NS-5 region using the maximum likelihood algorithm, shown as an unrooted tree. Symbols are as described for FIG. 2.

Analysis of the NS-5 region, which was based on several sequences of each of the three types (FIGS. 3, 4; Table 3), conformed the existence of 3 major groups, with type 3 sequences (SEQ ID NO: 13) forming a relatively homogeneous group that was quite distinct from types 1 and 2. The proposed separation of type 1 sequences into PT and K1 "sub-types" and type 2 sequences into K2a and K2b is supported by this analysis, in which the single type 2 blood donor sequence obtained in this study appears most similar to K2b. Differential n of HCV type 1 sequences into two groups is also clearly shown in the core (FIG. 7) and NS-3 regions (FIG. 5), in both cases with the type 3 sequences (SEQ ID NO: 15 and 14, respectively) appearing considerably more distant.

The clustering of phylogenetically distinct groups, their mixed distributions in a single geographic area (1, 7, 23, 27, 35) and our own finding of dual or triple infections in individual hemophiliacs all strongly suggest that the three types described here are distinct viruses rather than simply representing geographical or epidemiologically clustered variants of a single, highly variable but monophyletic group.

Our own phylogenetic analysis of the 5'NCR reveals the existence of three distinct groups. This contrasts with analyses of coding region, where there appears to be a very prominent differentiation of type 1 sequences into two "subtypes". However, unlike type 2 and 3 variants, the two subtypes are geographically distinct, one sub-type comprising sequences obtained exclusively from Japanese patients, and the other comprising predominantly USA/European sequences (Table 2). Indeed the only exception to this geographical classification is the HC-J1 sequence (26); one apparent exception (Pt-1) was obtained from a Japanese hemophiliac treated with imported factor VIII of USA origin (7,23), which is likely to have contained HCV variants corresponding to the other sub-type. There is insufficient sequence data to indicate whether the two proposed type 2 subtypes, K2a and K2b (7,23) represent geographically distinct variants.

The genomic organisation of HCV corresponds to that of flaviviruses and pestiviruses, with a single open reading frame encoding a polyprotein that is subsequently cleaved into structural and non-structural proteins. Weak sequence homologies have been detected with several other virus groups that have positive-sense RNA genomes (19,21). Although the overall degree of sequence dissimilarity between types 1, 2 and 3 cannot be measured by comparison of the small regions of sequence analysed in this study, a rough estimate of the extent of divergence in protein coding regions is given by an examination of the divergence of the partial core sequence. This shows that the difference between HCV type 1 and type 3 (SEQ ID NO: 15) core region (approximately 10% amino acid sequence divergence) is comparable to that which exists between different serotypes of the flavivirus, tick-borne encephalitis virus (14%; ref.20), but lower than that which is found between serotypes of a mosquito borne flavivirus, dengue fever virus (33%) , and the West Nile (WN) subgroup (28–43% divergence). The 5'NCR sequences of the different members of WN subgroup are also considerably more diverse than those of the three types of HCV (=50% similarity; ref.5), although within each of the members e.g. Murray Valley encephalitis virus, the 5'NCR is extremely well conserved (>95% similarity; ref.5). On the basis of these analogies, we speculate that the major types of HCV represent distinct "serotypes," each capable of human infection irrespective of the immune response mounted against other HCV types.

METHODS

Samples. Plasma from 18 different blood donors (E-b1 through E-b18), that were repeatedly reactive on screening by Abbott 2nd generation enzymeimmunoassay (EIA), and confirmed or indeterminate by a recombinant immunoblot assay (RIBA; Ortho; ref 1) were the principal samples used in this study. Sequences in the NS-3 region from 5 anti-HCV positive IVDUs (abbreviated as i1–i5 in ref. 31), 5 hemophiliacs who had received non-heat treated clotting concentrate, and who were also anti-HCV positive (h1–h5), 3 pools of 1000 donations collected in 1983 (p1–p3), and 5 separate batches of commercially available non-heat treated factor VIII (f1–f5) correspond to those described previously (31).

Primers. The primers used for cDNA synthesis and polymerase chain reaction (PCR) are listed in Table 1 (SEQ ID NO: 22 through 43). They were synthesised by Oswel DNA Service, Department of Chemistry, University of Edinburgh.

RNA Extraction and PCR. HCV virions in 0.2–1.0 ml volumes of plasma were pelleted from plasma by ultracentrifugation at 100,000 g for 2 hours at 4° C. RNA was extracted from the pellet as previously described (2,31). First strand cDNA was synthesized from 3 ul of RNA sample at 42° C. for 30 min. with 7 units of avian myeloblastosis virus reverse transcriptase (Promega) in 20 ul buffer containing 50 mM Tris-HCl (pH 8.0), 5 mM $MgCl_2$, 5 mM dithiothreitol, 50 mM KCl, 0.05 ug/ul BSA, 15% DMSO, 600 uM each of DATP, dCTP, dGTP and TTP, 1.5 uM primer and 10 U RNAsin (Promega).

PCR was performed from 1 ul of the CDNA over 25 cycles with each consisting of 25 sec. at 94° C., 35 sec. at 50° C. and 2.5 min. at 68° C. The extension time for the last cycle was increased to 9.5 min. The reactions were carried out with 0.4 unit Taq polymerase (Northumbria Biologicals Ltd.) in 20 ul buffer containing 10 mM Tris-HCl, pH 8.8, 50 mM KCl, 1.5 mM MgCl$_2$, 0.1% Triton X-100, 33 uM each of dATP, dCTP, dGTP and dTTP and 0.5 uM of each of the outer nested primers. One ul of the reaction mixture was then transferred to a second tube containing the same medium but with the inner pair of nested primers, and a further 25 heat cycles were carried out with the same programme. The PCR products were electrophoresed in 3% low melting point agarose gel (IBI) and the fragments were detected by ethidium bromide staining and UV illumination. For sequence analysis, single molecules of cDNA were obtained at a suitable limiting dilution at which a Poisson distribution of positive and negative results was obtained (30).

Direct Sequencing of PCR Products. The PCR products were purified by glass-milk extraction ("GeneCleanl"; Bio101, Inc.), one quarter of the purified products was used in sequencing reactions with T7 DNA polymerase (Sequenase; United States Biologicals) performed according to the manufacturer's instructions except that the reactions were carried out in 10% DMOS and the template DNA was heat denatured before primer annealing.

Phylogenetic Methods. The sequences were compiled by version 2.0 of the programs of Staden (32) and analysed by programs available in the University of Wisconsin Genetics Computer Group sequence analysis package, version 7.0 (6). Phylogenetic trees were inferred using two different programs available in the PHYLIP package of Felsenstein (version 3.4 June 1991; ref.9). The program DNAML finds the tree of the highest likelihood (the maximum likelihood tree) given a particular stochastic model of molecular evolution and has been shown to perform well in simulation studies (28). In the analyses performed here the global (G) option was used as this searches a greater proportion of all possible trees. The second program used was NEIGHBOR which clusters (following the algorithm of Saitou & Nei; ref.29) a matrix of nucleotide distances previously estimated using the program DNADIST (which itself was set, using the D option, to use the same stochastic model as underlies DNAML in order to estimate distances corrected for the probabilities of multiple substitution). In all cases the maximum likelihood and neighbour joining procedures produced congruent trees and thus only the former have been presented here.

To establish the interrelationships of the major types of HCV, we have separately analysed several regions of the viral genome that differ in sequence variability and evolutionary constraint. Thus the conclusions drawn from the sequence comparisons are not subject to spurious evolutionary phenomena that may affect a particular region. However, one problem with the analysis presented here was the absence of a viral sequence that was sufficiently distantly related to HCV to serve as an out-group. Thus, although we describe the interrelationships of different sequence variants of HCV, it should be stressed that we have no means of deciding which sequence is ancestral to the others. The trees are thus drawn in the less familiar un-rooted form to indicate this.

RESULTS

Figure 1B:
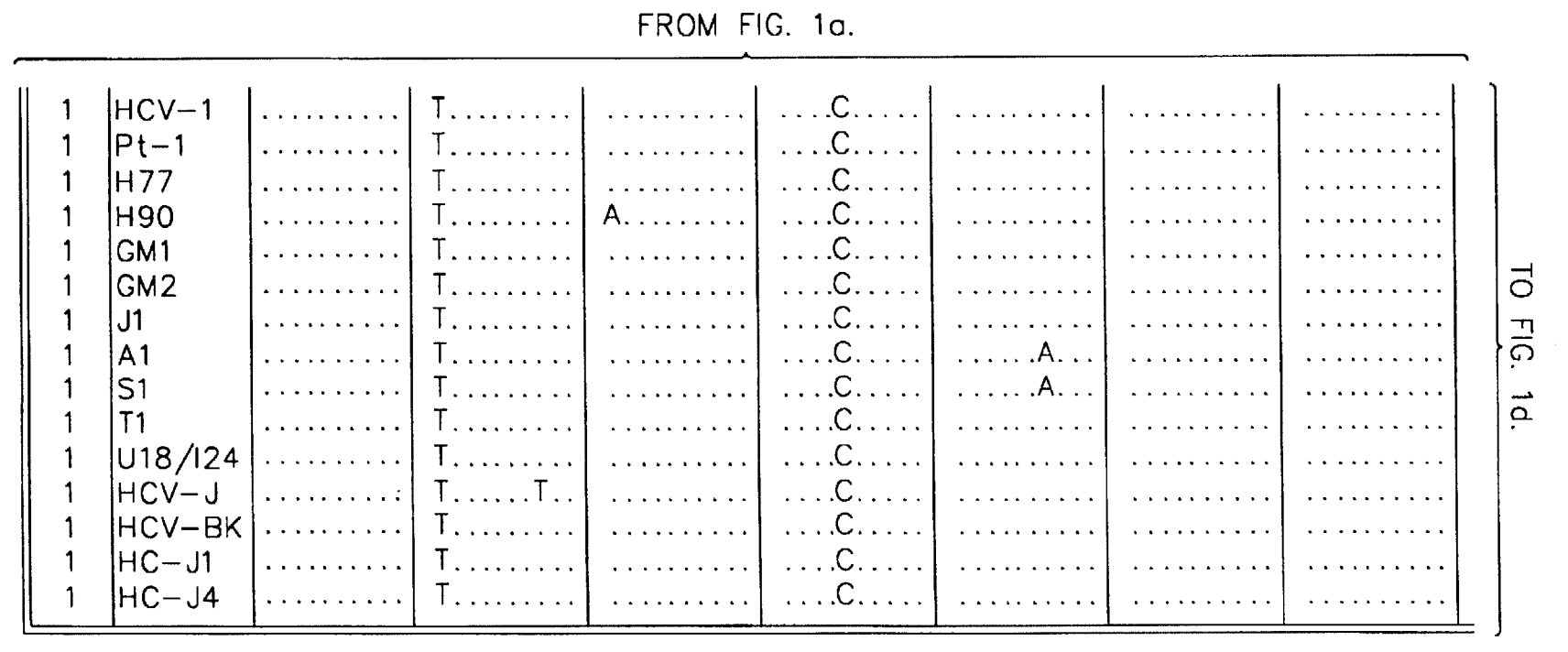
Figure 1G:
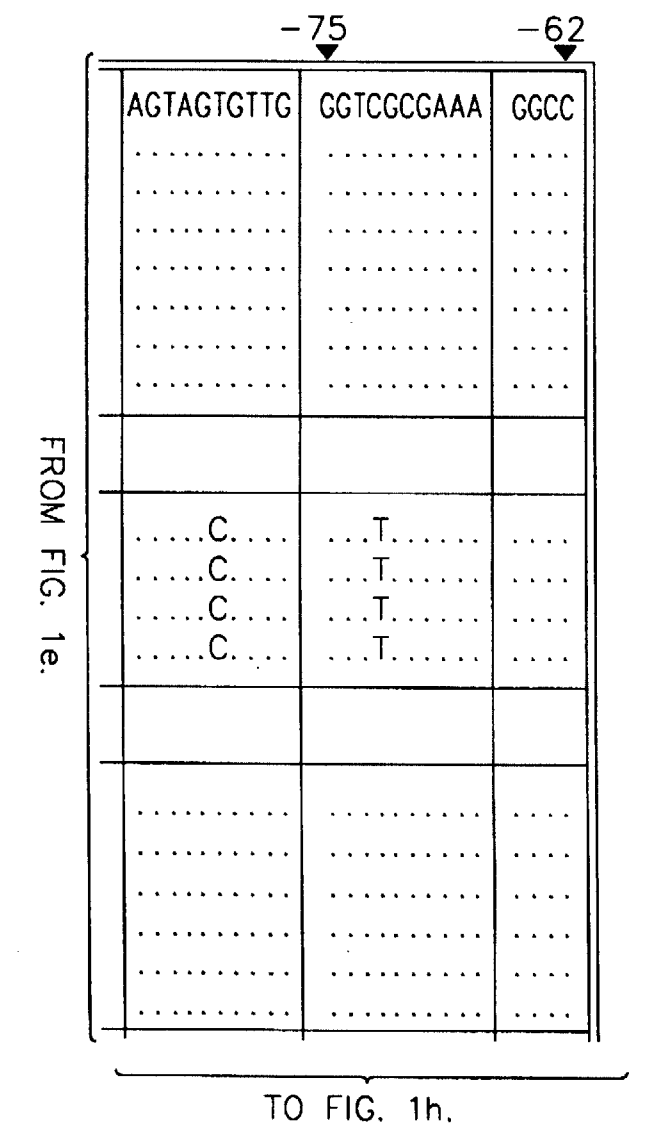
Figure 1H:
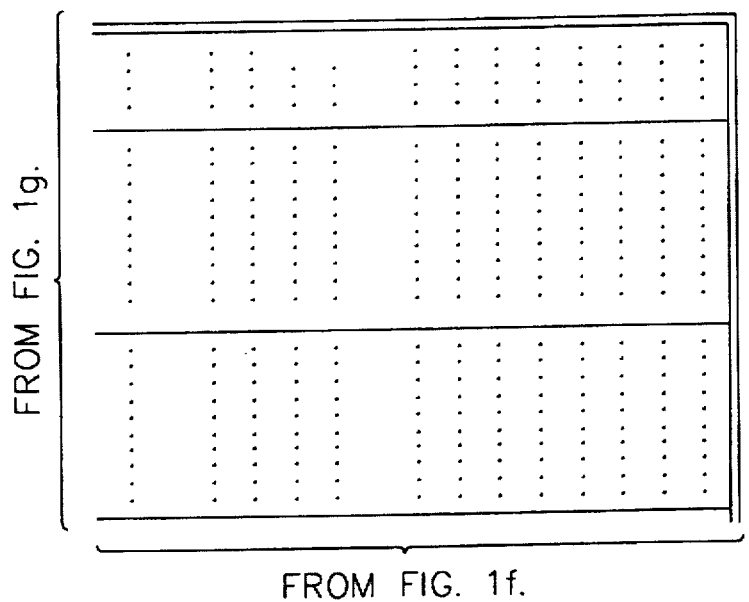
Figure 2:
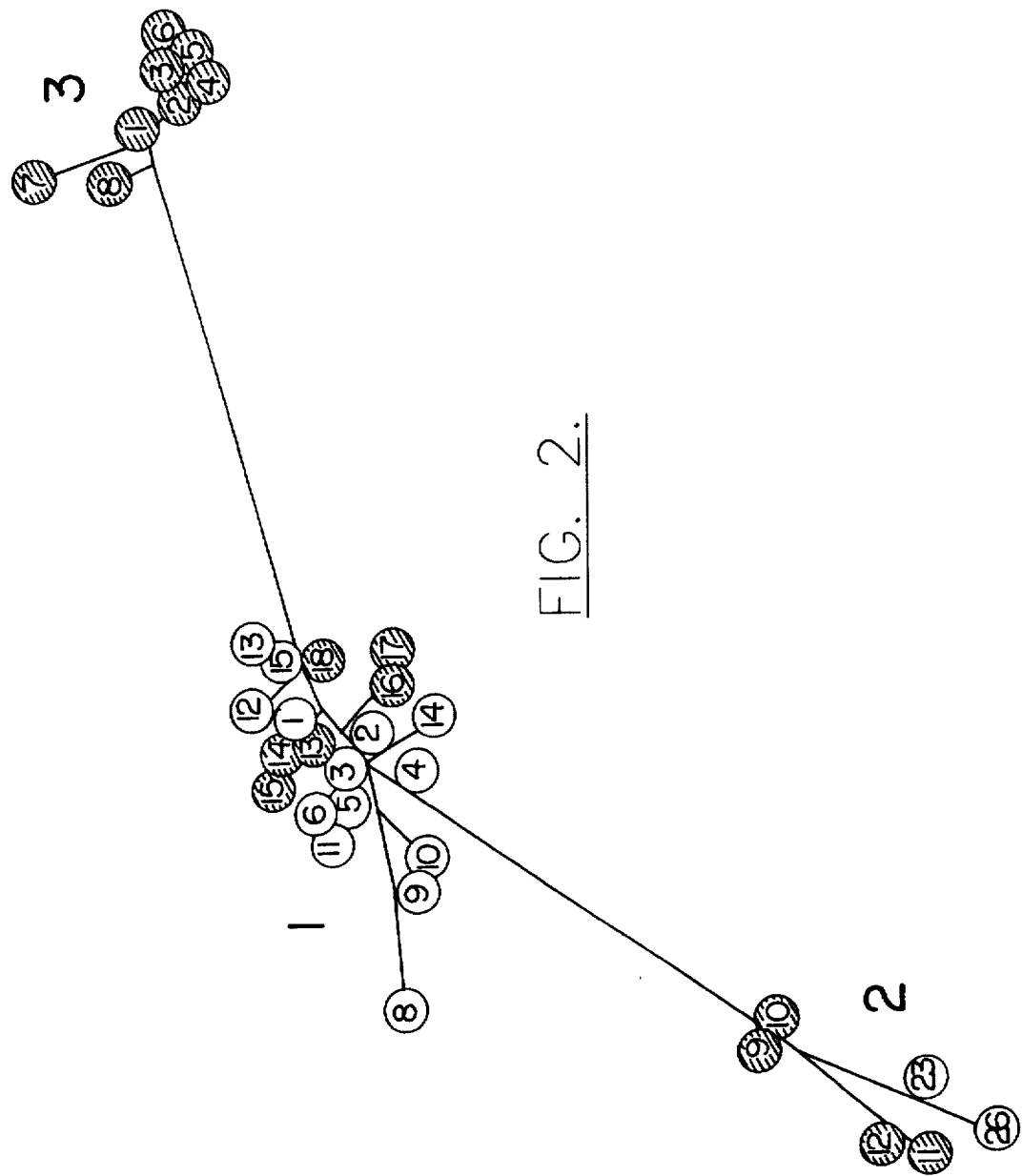
FIG. 2 is a phylogenetic analysis showing clustering of the sequences into three types viz; HCV-1, HCV-2 and HCV-3 for the 5' NCR results of FIG. 1 using the maximum likelihood algorithm, shown as an unrooted tree. Numbers 1–18 in full circles correspond to blood donor sequences E-b1 through E-b18. Numbers 1 to 26 in open circles correspond to the previously published sequences identified in Table 2.

1) Analysis of the 5' non-coding region. Samples were obtained from 18 blood donors that were repeatedly reactive in the Abbott 2nd Generation enzyme immunoassay and which were confirmed or indeterminate in the Chiron 4-RIBA (E-b1 through E-b18, ref.10). HCV sequences present in stored plasma samples from each donor were amplified with primers corresponding to sites in the 5'NCR (SEQ ID NO: 22 through 25) (12,25) that are well conserved between all known HCV type 1 and type 2 variants (4,11, 13,16,23,24,26,33). Sequencing of the PCR product, after limiting dilution to isolate single molecules of CDNA before amplification, allowed approximately 190 bps in the centre of the region to be compared with equivalent published sequences (FIG. 1).

Within the sequences, constant as well as variable regions can be found. Six sequences from donors E-b13 through E-b18 closely resembled those previously described as type 1 (4,11,13,16,23,24,26,33) and others resembled type 2(23) sequences (E-b9 through E -b12). However, eight sequences (E-b1 through E-b8) were distinct from both types, and have been provisionally termed type 3(SEQ ID NO: 12). Division of the sequences into three types is supported by formal phylogenetic analysis using the maximum likelihood (FIG. 2) and neighbour joining algorithms (data not shown) of the blood donor sequences along with previously published sequences (identified in table 2). Sequence variability within the three groups is in each case considerably less than that which separates the types. No sequence intermediate between the three types were found. This tree shows that the provisionally identified type 3 group (SEQ ID NO: 12) is equally distinct from type 1 as is type 2. Using the DNAML model, the corrected distances between sequences within each type were in each case less than 3%. Between groups, they ranged from 9% (between type 1 and type 3 (SEQ ID NO: 12), and between type 1 and 2), to 14% between type 2 and type 3 (SEQ ID NO: 13) (table 3).

2) Analysis of the NS-5 Region. The nucleotide sequence of the NS-5 region has been found to vary significantly between the previously described K1 and K2 variants of HCV (7). To investigate whether type 3 (SEQ ID NO: 13) sequences were equally distant from the other two types in this region as well as in the 5'NCR, we compared sequences from four type 3 blood donors (E-b1, E-b2, E-b3 and E-b7) and one type 2 donor (E-b12) with previously published sequences (FIG. 3; FIG. 4; table 3).

A remarkable variation was observed between sequences of the three types in this region. Again, type 3 sequences (SEQ ID NO: 13) form a separate group from type 1 and type 2 in this region. However, unlike the 5'NCR, there appear to be subdivisions within the type 1 and type 2 groups. Type 1 sequences are split between those found in Japanese infected individuals (e.g. HCV-J; HCV-BK; sequence numbers 12, 13, 16–20 in table 2) and those of U.S.A. origin (HCV-1, Pt-1, H77, H90; sequence numbers 1–4; FIG. 4). There is also some evidence for a split between type 2 sequences, those corresponding to their previous designation as K2a (7) appearing distinct prom type K2b sequences and the Scottish blood donor, E-b12.

Table 3 shows that the average nucleotide distances between the two groups of HCV type 1 sequences is 25% (indicated here as type 1a [USA] and type 1b [Japanese]), with variation of only 4–7% within each group. The nucleotide sequence divergence within the two type 1 groups is similar to that which exists between K2a and K2b (table 3). However, both of these distances are considerably less than those which exist between type 1 and type 2 sequences (52–62%), and type 3 (SEQ ID NO: 13) (48–49%), and the distance between type 2 and type 3 (SEQ ID NO: 13) sequences (53–60%).

Figure 6:
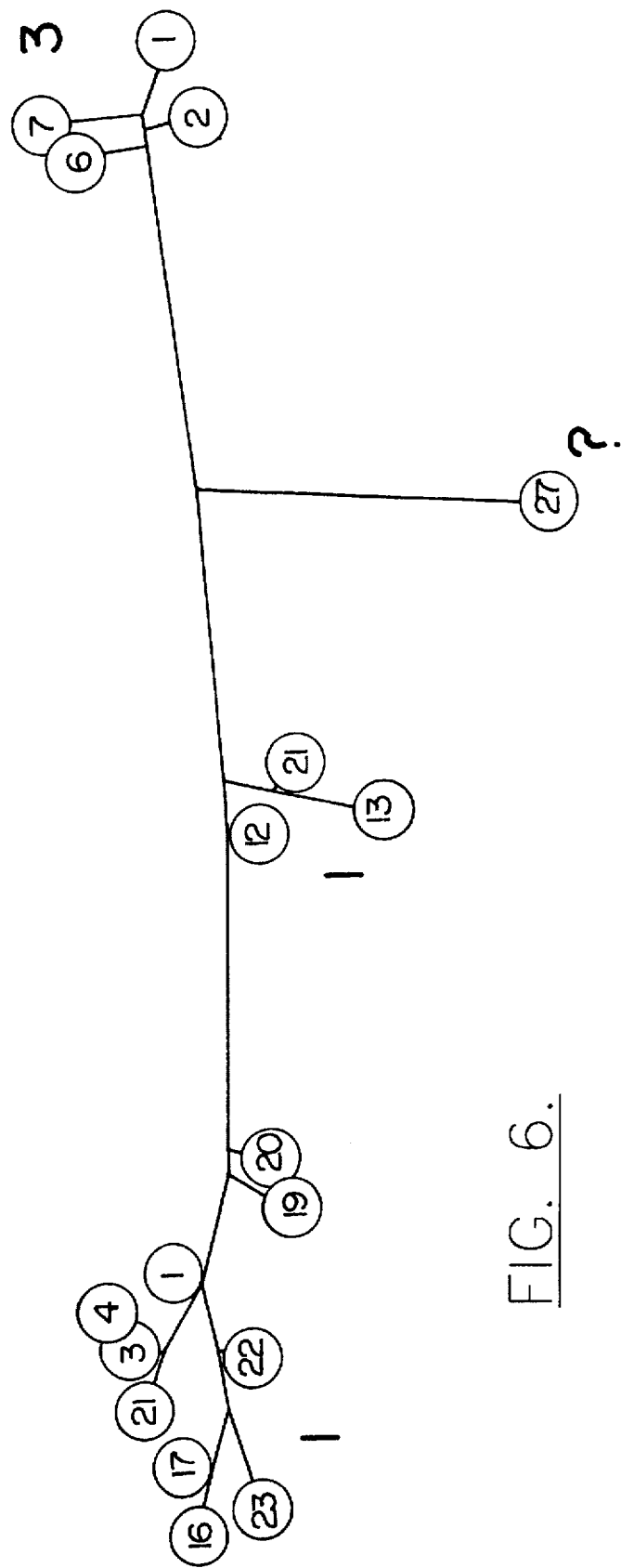
FIG. 6 is a phylogenetic analysis of the NS-3 region using the maximum likelihood algorithm, shown as an unrooted tree. Representative nucleotide sequences of the 5 groups of type 1 sequences shown in FIG. 5 coded as follows: 19 (full circle) i3; 20 (full circle) i4; 21 (full circle) h5; 22 (full circle) h3; 23 (full circle) h1. Symbols are as described for FIG. 2.

3) Analysis of the NS-3 region. Amplification reactions were carried out using previously published primer sequences in the NS-3 region (37), and a pair of empirically derived inner primers (SEQ ID NO: 28 and 29) (31). Although these primers amplified HCV sequences from a high proportion of anti-C-100 positive sera from haemophiliacs (31), they were less effective with sera from IVDUs (31), and with blood donor samples (3 positive out of 15 tested; data not shown). Two conserved sites in the amplified fragment were identified by sequence analysis of the NS-3 region from the haemophiliac and IVDU patients, and two new primers corresponding to these were specified (207 (SEQ ID NO: 31), 208 (SEQ ID NO: 30); Table 1). The combination of 288 (SEQ ID NO: 28)–208 (SEQ ID NO: 30) (first round) and 290 (SEQ ID NO: 29)–207 (SEQ ID NO: 31) (second round) primers successfully amplified samples from four donors infected with HCV type 3 (E-b1, E-b2, E-b6 and E-b7) but none of those infected with HCV type 2 (data not shown). This enabled a comparison of the new type (SEQ ID NO: 14) with our own (31) and previously published type 1 sequences (FIGS. 5, 6; table 3). For clarity, only seven of the type 1 sequences obtained in this study (E-b16, E-b17, i3, i3, h5, h3 and h1) are shown in the tree. These sequences are representative of the range of variation found in this region in individuals infected in Britain; comparison of the tree previously published (31) with FIG. 6 shows that the former forms a very small component of the overall tree obtained once Japanese type 1 and type 3 sequences are added.

The maximum likelihood tree shows that type 1 and type 3 (SEQ ID NO: 14) have diverged considerably from each other. As was found in the NS-5 region, subtypes of type 1 sequences are found in NS-3. Again, sequences of Japanese origin (HCV-J, HCV-BK and JH) are distinct from the prototype (PT) sequence, and those found in Scottish blood donors (E-b16, E-b17, p1-3), IVDUs (i1-5) and haemophiliacs (h1-5), all of which correspond to the prototype sequence (FIG. 5). However, the average subtype difference (23%) is lower than those that exist between HCV-1 and HCV-J with the four type 3 sequences (SEQ ID NO: 14) (37–43%). As reported previously (31), the majority of nucleotide substitutions that exist between type 1 sequences are silent (i.e. do not affect the encoded amino acid sequence), while numerous amino aced substitutions exist between type 1 and type 3 (SEQ ID NO: 14) sequences (FIG. 5). The analysis of the NS-3 region includes the sequence of clone A (35) which was obtained from Japanese patients with NANB hepatitis, and which was reported to be distinct from existing HCV type 1 sequences. In FIG. 6, this sequence appears to be distinct from both HCV type 1 and type 3 (SEQ ID NO: 14), with corrected sequence distances of 33–43% and 36% respectively. Although it is not possible to assign this sequence to any known group at this stage, these distances are not inconsistent with the hypothesis that it represents a type 2 sequence, or an equally distinct novel HCV type.

4) Partial Sequence of the Putative Core Region of HCV.

Figure 8:
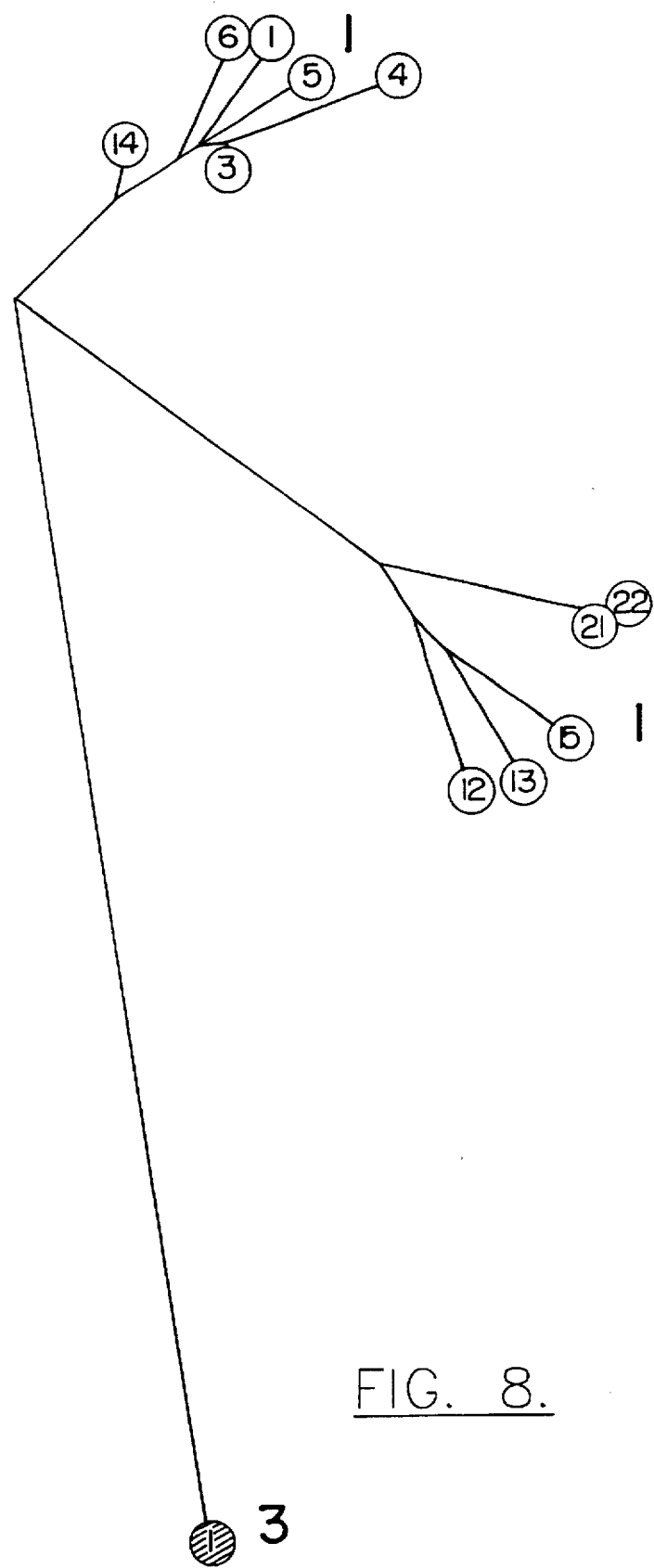
FIG. 8 is a phylogenetic analysis of the core region using the maximum likelihood algorithm, shown as an unrooted tree. Symbols are as described for FIG. 2.

The region encoding the putative core protein is comparatively well conserved in its nucleotide sequence between known type 1 variants, showing nucleotide and amino acid sequence similarities of 90–98% and 98–99% respectively (11, 24). Part of the core region from the blood donor Eb1, who has type 3 sequences in other regions analysed was amplified with primers 410 (SEQ ID NO: 26) and 406 (SEQ ID NO: 27) and compared with previously published type 1 sequences (FIGS. 7, 8; table 3). This analysis confirms that the type 3 sequence (SEQ ID NO: 15) was distinct from those of type 1, and again there was a prominent subdivision of type 1 sequences into Japanese (HCV-J, HCV-BK, HC-J4, JH and J7) and USA/European (HCV-1, H77, H90, GM1, GM2) sequences. As was found in NS-3, very little amino acid sequence variation is found in the core regions of type 1 sequences; almost all of the nucleotide differences between the two groups are at "silent" sites. By contrast, the type 3 sequence (SEQ ID NO: 15) shows 7–8 amino acid substitutions on comparison with type 1 sequences.

TABLE 1

SEQUENCES AND SOURCES OF PRIMERS USED FOR AMPLIFICATION OF HCV GENOME.

| Name | Region | Position of 5' base[a] | Sense[b] | Sequences 5'-3' | Ref. |
|---|---|---|---|---|---|
| 209 | 5'NCR | 8 | − | ATACTCGAGGTGCACGGTCTACGAGACCT SEQ ID NO:22 | (12) |
| 211 | 5'NCR | −29 | − | CACTCTCGAGCACCCTATCAGGCAGT SEQ ID NO:23 | (12) |
| 939 | 5'NCR | −297 | + | CTGTGAGGAACTACTGTCTT SEQ ID NO:24 | (25) |
| 940 | 5'NCR | −279 | + | TTCACGCAGAAAGCGTCTAG SEQ ID NO:25 | (25) |
| 410 | CORE | 410 | − | ATGTACCCCATGAGGTCGGC SEQ ID NO:26 | |
| 406 | CORE | −21 | + | AGGTCTCGTAGACCGTGCATCATGAGCAC SEQ ID NO:27 | |
| 288 | NS-3 | 4951 | − | CCGGCATGCATGTCATGATGTAT SEQ ID NO:28 | (31) |
| 290 | NS-3 | 4932 | − | GTATTTGGTGACTGGGTGCGTC SEQ ID NO:29 | (31) |
| 208 | NS-3 | 4662 | + | TCTTGAATTTTGGGAGGGCGTCTT SEQ ID NO:30 | |
| 207 | NS-3 | 4699 | + | CATATAGATGCCCACTTCCTATC SEQ ID NO:31 | |
| 007 | NS-4 | 5293 | − | AACTCGAGTATCCCACTGATGAAGTTCCACAT SEQ ID NO:32 | |
| 220 | NS-4 | 5278 | − | CACATGTGCTTCGCCCAGAA SEQ ID NO:33 | |
| HCV type 3:| | | | | | |
| 221 | NS-4 | 4858 | + | GGACCTACGCCCCTTCTATA SEQ ID NO:34 | |
| 008 | NS-4 | 4878 | + | TCGGTTGGGGCCTGTCCAAAATG SEQ ID NO:35 | |
| HCV type 2: | | | | | |
| 281 | NS-4 | 4858 | + | GGTCCCACCCCTCTCCTGTA SEQ ID NO:36 | |
| 509 | NS-4 | 4878 | + | CCGCTTGGGTTCCGTTACCAACG SEQ ID NO:37 | |
| HCV type 1: | | | | | |
| 253 | NS-4 | 4858 | + | GGGCCAACACCCCTGCTATA SEQ ID NO:38 | |
| 196 | NS-4 | 4878 | + | CAGACTGGGCGCCGTTCAGAATG SEQ ID NO:39 | |
| 242 | NS-5 | 8304 | − | GGCGGAATTCCTGGTCATAGCCTCCGTGAA SEQ ID NO:40 | (7) |

TABLE 1-continued

SEQUENCES AND SOURCES OF PRIMERS USED FOR AMPLIFICATION OF HCV GENOME.

| Name | Region | Position of 5' base[a] | Sense[b] | Sequences 5'-3' | Ref. |
|------|--------|------------------------|----------|-----------------|------|
| 555 | NS-5 | 8227 | − | CCACGACTAGATCATCTCCG SEQ ID NO:41 | |
| 243 | NS-5 | 7904 | + | TGGGGATCCCGTATGATACCCGCTGCTTTGA SEQ ID NO:42 | (7) |
| 554 | NS-5 | 7935 | + | CTCAACCGTCACTGAACAGGACAT SEQ ID NO:43 | |

[a]Position of 5' base relative to HCV genomic sequence in ref. no. (4)
[b]Orientation of primer sequence (+: sense; −: anti-sense)
‡Abbreviations: A: adenine, c: cytidine; G: guanidine, T: thymidine.
¶Separate sense primers required to enable amplification of each HCV type.

TABLE 2

SOURCE AND CITATION OF PREVIOUSLY PUBLISHED HCV SEQUENCES USED IN THIS STUDY

| No. | Type | Abbreviation | Geographical Source | Reference | Ref. No. |
|-----|------|--------------|---------------------|-----------|----------|
| 1 | 1 | HCV-1 | U.S.A. | Choo et al., 1991 | (4) |
| 2 | 1 | Pt-1 | Japan | Nakao et al., 1991 | (23) |
|   |   |       |       | Enomoto et al., 1990 | (7) |
| 3,4 | 1 | H77. H90 | U.S.A. | Ogata et al., 1991 | (24) |
| 5,6 | 1 | GM-1, GM-2 | Germany | Fuchs et al., 1991 | (11) |
| 7 | 1 | J1 | Japan | Han et al., 1991 | (13) |
| 8 | 1 | A1 | Australia | Han et al., 1991 | (13) |
| 9 | 1 | S1 | S. Africa | Han et al., 1991 | (13) |
| 10 | 1 | T1 | Taiwan | Han et al., 1991 | (13) |
| 11 | 1 | U18/I24 | U.S.A./Italy | Han et al., 1991 | (13) |
| 12 | 1 | HCV-J | Japan | Kato et al., 1990 | (16) |
| 13 | 1 | HCV-BK | Japan | Takamizawa et al., 1991 | (33) |
| 14, 15 | 1 | HC-J1,-J4 | Japan | Okamoto et al., 1990 | (26) |
| 16–20 | 1 | K1, Kl- 1–4 | Japan | Enomoto et al., 1990 | (7) |
| 21 | 1 | JH | Japan | Kubo et al., 1990 | (17) |
| 22 | 1 | J7 | Japan | Takeuchi et al., 1990 | (34) |
| 23–26 | 2 | K2a, K2a-1. K2b, K2b-1 | Japan | Nakao et al., 1991 | (23) |
|   |   |   |   | Enomoto et al., 1990 | (7) |
| 27 | ? | Clone A | Japan | Tsukiyama-Kohara, 1991 | (35) |

TABLE 3

NUCLEOTIDE DISTANCES BETWEEN THE THREE HCV TYPES IN FOUR REGIONS OF THE GENOME.

| REGION | TYPES (n[a]) | 1a | 1b | 2a | 2b | 3 |
|--------|------|------|------|------|------|------|
| 5'NCR | 1 (20) | 0.0163 | n/a[b] | | | |
|       | 2 (6)  | 0.0869 | n/a | 0.0214 | | |
|       | 3 (8)  | 0.0948 | n/a | 0.1331 | n/a | 0.0123 |
| CORE  | 1a (6) | 0.0358 | | | | |
|       | 1b (5) | 0.0855 | 0.0227 | | | |
|       | 3 (1)  | 0.1801 | 0.1511 | n/d[c] | n/d | 0.0000 |
| NS-3  | 1a (34) | 0.0699 | | | | |
|       | 1b (3) | 0.2270 | 0.0535 | | | |
|       | 3 (4)  | 0.3689 | 0.4279 | n/d | n/d | 0.0460 |
| NS-5  | 1a (4) | 0.0743 | | | | |
|       | 1b (7) | 0.2477 | 0.0372 | | | |
|       | 2a (2) | 0.6092 | 0.6206 | 0.0612 | | |
|       | 2b (3) | 0.5214 | 0.5732 | 0.2252 | 0.0655 | |
|       | 3 (4)  | 0.4754 | 0.4890 | 0.5983 | 0.5299 | 0.0322 |

[a]number of sequences analysed
[b]n/a: not applicable
[c]n/d: not done

II). SEROLOGICAL REACTIVITY OF BLOOD DONORS INFECTED WITH THREE DIFFERENT TYPES OF HEPATITIS C VIRUS.

HCV sequences were amplified in the 5'non-coding region (5'NCR), core, NS-3 and NS-5 regions from blood donors, haemophiliacs and intravenous drug abusers. Blood donations that were repeatedly reactive on screening with Abbott 2nd generation enzyme immunoassay (EIA) and positive or indeterminate by Ortho recombinant immunoblot assay (RIBA) were amplified by primers in the 5'NCR (reference 10). The first fourteen PCR-positive blood donations (where PCR was used to amplify and thus detect HCV RNA present in the blood) were then typed by sequence analysis of the amplified region, and compared with their serological reactivity to a range of structural and non-structural peptides in two 1st generation EIAs (Ortho HCV ELISA; Abbott HCV EIA) and two RIBA assays (Ortho RIBA and Innogenertics LIA; Table 4). The five donations containing HCV type 1 sequences were positive in both EIAS, reacted with all antigens in the Ortho RIBA assay, and were broadly reactive in the LIA. However, all but two of the sera from donors with type 2 and 3 infections were completely negative an anti-C100 EIA screening and failed to react with 5-1-1, C100 (RIBA) and NS4 (LIA).

Furthermore, some carriers of HCV type 3 variants reacted poorly with the C33 (NS-3) peptide in the Ortho RIBA, and yielded two "indeterminate" results (donor nos. 11 and 13).

Thus, current tests using Ortho RIBA and (to a lesser extent) Innogenetics LIA tests are unable to reliably detect HCV-2 and HCV-3 genotypes. For reliable testing for all HCV types, antigens from 5-1-1, C100 and NS4 for each of the three types of HCV should preferably be included in the panel of antigens.

TABLE 4

SEROLOGICAL REACTIVITY OF SERA FROM BLOOD DONORS INFECTED WITH THREE TYPES OF HEPATITIS C VIRUS

| Donor Number | HCV genotype | anti-C100 O* | At | Ortho RIBA 5-1-1 | C100 | C33 | C22 | Innogenetics LIA NS4 | NS5 | C1‡ | C2 | C3 | C4 |
|---|---|---|---|---|---|---|---|---|---|---|---|---|---|
| E-b13 | 1 | + | + | 3§ | 4 | 4 | 4 | 2§ | 3 | 1 | 2 | 1 | 1 |
| E-b15 |   | + | + | 4 | 4 | 4 | 4 | 2 | 3 | 3 | 2 | 2 | 1 |
| E-b16 |   | + | + | 4 | 4 | 4 | 4 | 2 | 3 | 2 | 3 | 3 | — |
| E-b17 |   | + | + | 4 | 4 | 4 | 4 | 3 | 3 | 3 | 2 | 1 | 1 |
| E-b18 |   | + | + | 4 | 4 | 4 | 4 | 3 | — | 2 | 1 | 1 | — |
| E-b9 | 2 | + | + | — | 1 | 3 | 4 | — | — | 3 | 1 | 1 | 3 |
| E-b10 |   | − | − | — | — | 4 | 4 | — | 3 | 2 | 2 | 2 | — |
| E-b11 |   | − | − | — | — | 4 | 4 | — | 3 | 4 | 2 | 2 | 3 |
| E-b12 |   | − | − | — | — | 4 | 4 | — | 1 | 3 | 1 | 2 | 2 |
| E-b1 | 3 | − | − | — | — | — | 4 | — | 1 | 3 | 1 | — | 3 |
| E-b2 |   | − | − | — | — | 4 | 4 | — | 2 | 1 | 1 | 1 | 2 |
| E-b3 |   | + | + | — | — | 2 | 4 | 2 | 2 | 1 | 2 | 2 | 1 |
| E-b5 |   | − | − | — | — | 2 | 4 | — | — | 3 | 1 | 2 | 3 |
| E-b7 |   | − | − | — | — | — | 4 | — | 2 | 3 | 1 | 1 | 4 |

*Ortho HCV ELISA (Recombinant C100-3)
†Abbott HCV ELA (Hepatitis C Recombinant DNA Antigen)
‡Core oligopeptides, 1–4
§Bands scored - (negative) to 4 (strong positive) according to manufacturers instructions.

PART III. MAPPING OF ANTIGENIC DETERMINANTS IN NS-4

Introduction

With an overall aim of improving serological screening assays, we have obtained sequence data from the antigenic region of region corresponding to c100-3 for types 2 and 3. This information was used to epitope map the region, to define additional immunoreactive peptides that could be used to improve serological anti-HCV assays.

Methods:

PCR and sequencing. Plasma samples from Scottish blood donors yielding repeatedly reactive donations on 2nd generation anti-HCV screening (Abbott or Ortho), and which were confirmed or indeterminate on confirmatory testing by RIBA (Chiron) were referred to the Department of Medical Microbiology from the Scottish National Blood Transfusion Service Microbiology Reference Laboratory. HCV RNA within the plasma samples was extracted and amplified with primers in the 5'NCR as described previously (Chan et al., 1992). HCV was typed by sequence analysis of the amplified DNA as described previously (Simmonds et al., 1990) and by RFLP analysis.

Five samples from different donors infected with HCV type 3 (nos. 40, 38, 36, 26 and 1787), four infected with type 2 (nos. 31, 59, 940 and 810) and five with type 1 infection (nos. 16, 42, 77, 1801 and 1825) were amplified with primers corresponding to sense and anti-sense sequences (SEQ ID NO: 32 through 39) spanning the antigenic region of NS-4 (table 1). Nucleotide sequences obtained from the amplified DNA were compared and used to define consensus sequences for each HCV type. In-frame translation of the nucleotide sequences yielded an uninterrupted consensus amino acid sequence that was used to define a series of overlapping oligopeptides for epitope mapping.

Epitope mapping and determination of antibody specificities

Overlapping synthetic peptides were synthesised on polypropylene pins using kits commercially available from Cambridge Research Biochemicals Ltd. The principle of the addition reactions is described in refs (Geysen et al., 1984; Geysen et al., 1985). Antibody reactions were carried out on pins disrupted by sonication (30 minutes) in 1% sodium dodecyl sulphate, 0.1% 2-mercaptoethanol, 0.1M sodium dihydrogen orthophosphate. Pins were pre-coated in 1% ovalbumin, 1% bovine serum albumin, 0.1% Tween-20 in phosphate buffered saline (PBS) for one hour at room temperature. Serum or plasma was diluted 1.40 in PBS+ 0.1% Tween-20 (PBST) and incubated with the blocked pins at 4° C. for 18 hours. After washing in 4 changes of PBST (10 minutes at room temperature, with agitation), bound antibody was detected by incubation in a 1/2000 dilution of affinity isolated anti-human IgG, peroxidase conjugate (Sigma) for one hour at room temperature. Following washing (4 changes in PBST), pins were incubated in a 0.05% solution of azino-di-3-ethyl-benzthiazodinsulphonate in 0.1M sodium phosphate/sodium citrate buffer (pH 4.0) containing 0.03% hydrogen peroxide for 20 minutes. Optical densities were read at 410 nm.

RESULTS

HCV RNA in plasma samples from five donors infected with HCV type 3 by sequence analysis of the 5'NCR, and by RFLP were amplified in the NS-4 region using primers (SEQ ID NO: 32 through 39) listed in Table 1. Because of the high degree of sequence variability in this region, it was necessary to use separate sense primers (SEQ ID NO: 34 through 39) for the amplification of different HCV types. However, the anti-sense primers (SEQ ID NO: 32 and 33) were in a highly conserved region and could be used for amplification of all three types. Sequence analysis was carried out as previously described. This gave a continuous sequence from position 4911 to 5271 (numbered as in Choo et al., 1991) (HCV-3–SEQ ID NO: 16) (FIG. 9a). Little sequence variability (highlighted) was observed between the four different donors in this region.

The nucleotide sequences were used to deduce the sequence of the encoded peptide (FIG. 9b). The putative protein contains mainly hydrophillic residues but no potential sites for N-linked glycosylation. Amino acid sequence variability with HCV type 3 was confined to only five residues (SEQ ID NO: 17) (FIG. 9b). However, this region differed considerably from the amino acid sequences of other blood donors infected with HCV types 1 and 2 (T16, 42, 77, 1801, 1825, 351, 940 and 810; FIG. 10a). Sequence comparison between the major HCV types from residues 1679 to 1769 reveals three regions of considerable amino acid sequence variability. Most of the observed differences between types involve non-synonymous amino acid substitutions, particularly alternation of acidic and basic residues in the hydrophillic regions. These changes would be expected to profoundly alter the overall conformation of the protein, and its antigenicity.

The consensus amino acid sequences in this region of types 1, 2 and 3 (SEQ ID NO: 17) (FIG. 10b) were used to define three series of 82 nonameric oligopeptides (spanning residues 42 to 128 of (SEQ ID NO: 17) overlapping by eight of the nine residues with those before and after in the series (FIG. 11a–c). These were synthesised on a 12×8 arrays of polypropylene pins as described in Methods. Antibody reactivity to the immobilised antigens on the pins was determined by indirect ELISA, using an overnight incubation with a 1/40 dilution of test serum overnight at 4° C., followed by washing, and detection with an anti-human IgG-peroxidase conjugate and appropriate substrate (see Methods).

Figure 12A:
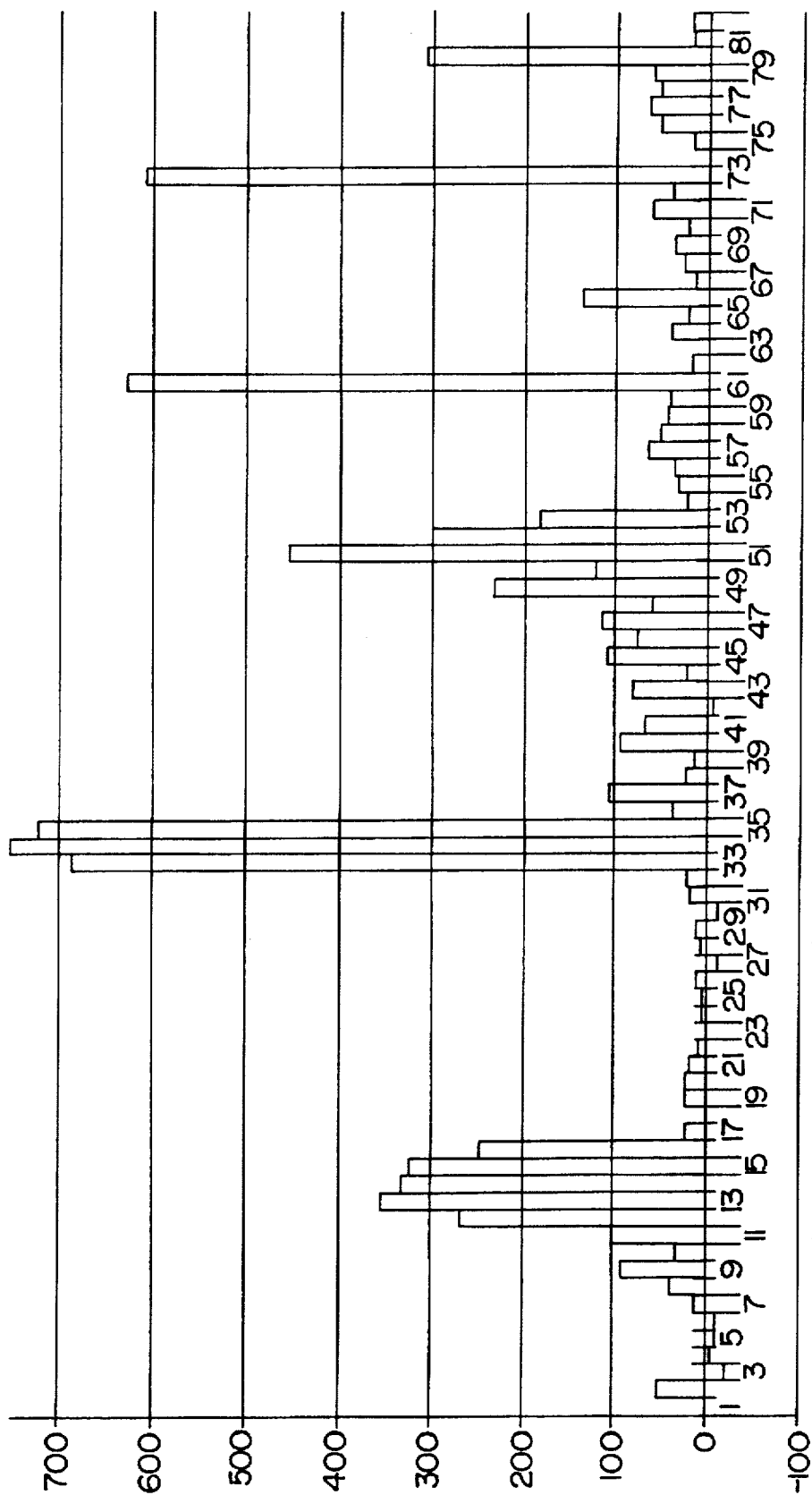
FIGS. 12a, 12b and 12c show antibody reactivity of three sera from blood donors infected with HCV type 3 with HCV type 3-encoded oligopeptides in the antigenic region of NS-4 (sequences 1–82 shown in FIG. 11a) (derived from residues 42 to 128 of SEQ ID NO: 17). Antibody reactivity to oligopeptides (x-axis), recorded as optical densities in the range from –01 to 0.75 (and >0.75) recorded on the y-axis.
Figure 12B:
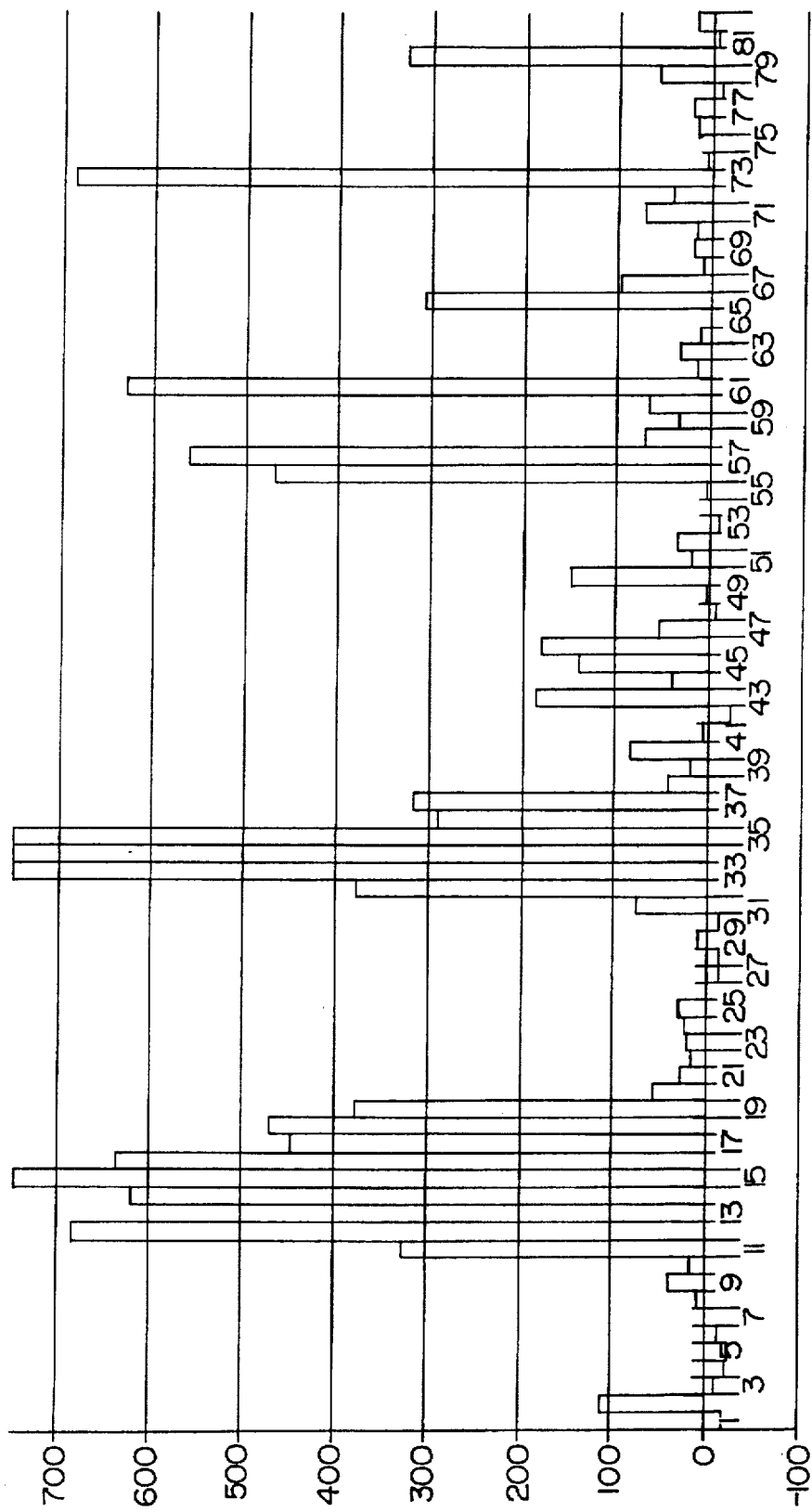
Figure 12C:
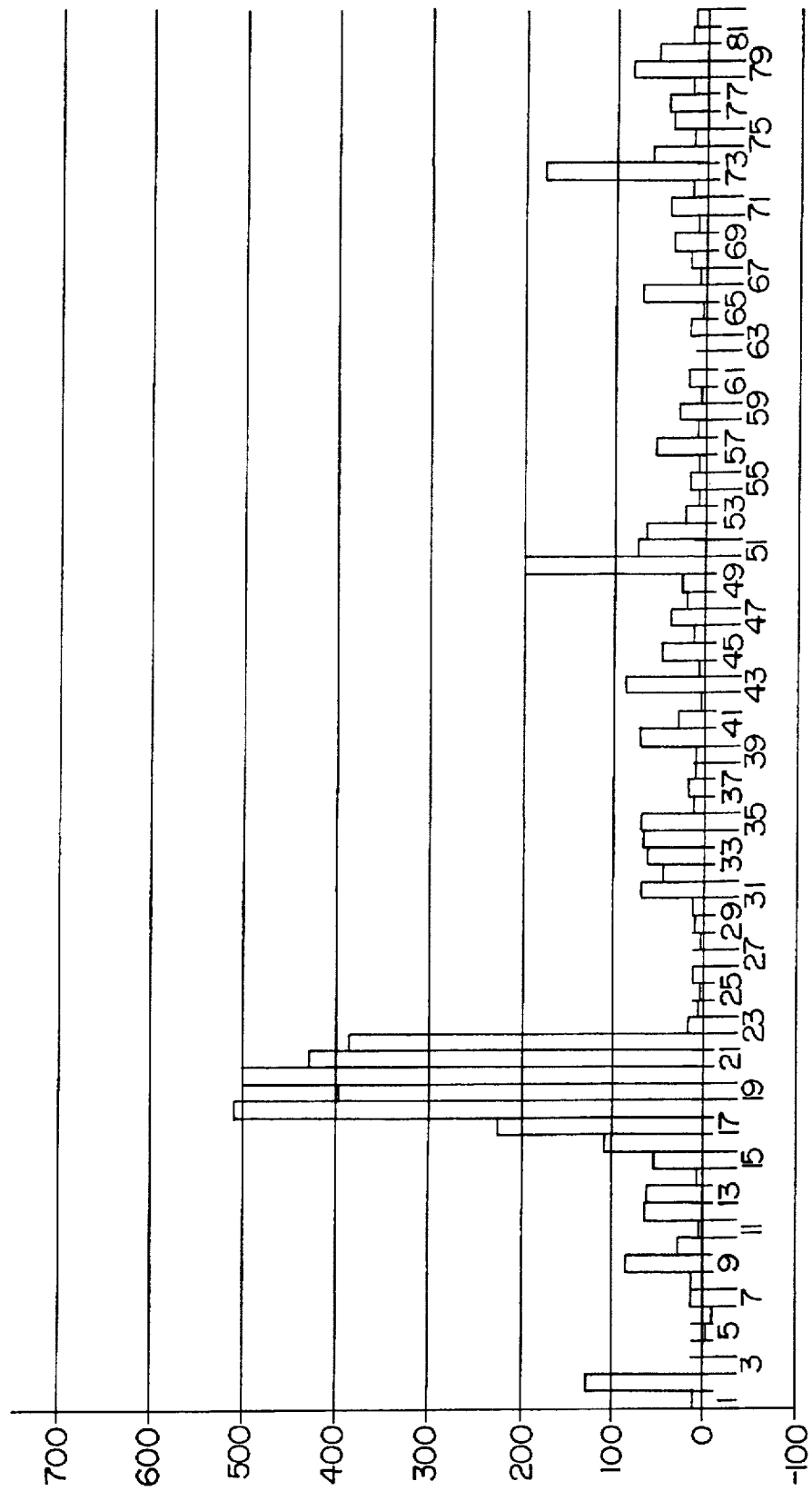

Reactivity of an anti-HCV negative, PCR-negative donor, with no known risk factors for HCV infection with the three series of peptides was determined. No significant reactivity is shown with any of the HCV-encoded oligopeptides. Reactivity of sera from three donors infected with HCV type 3 (derived from residues 42 to 128 of (SEQ ID NO: 17) to each of the oligopeptides is shown in FIGS. 12a–12c. All three sera reacted with peptides ranging from No. 13 (sequence KPALVPDKE amino acids 54 to 62 in (SEQ ID NO: 17; FIG. 7) to No. 22 (sequence VLYQQYDEM; residues 63 to 71 in (SEQ ID NO: 17) in the first antigenic region, although the precise peptides recognised varied slightly between individuals. All three sera reacted to varying extents with a second antigenic region, lying in the range from oligopeptides 32 to 42 (of sequence ECSQAAPYI, residues 73 to 81 of (SEQ ID NO: 17, to QAQVIAHQF, residues 83 to 91 of (SEQ ID NO: 17. Weaker and more variable reactivity was observed to peptides 48 (residues 88 to 96 of (SEQ ID NO: 17) to 53 (residues 94 to 102 of (SEQ ID NO: 17). Finally, significant reactivity was also observed to single oligonucleotides 2 (residues 43 to 51 of (SEQ ID NO: 17) (2 of 3 samples), 61 (residues 102–110 of (SEQ ID NO: 17) (2 of 3), 66 (residues 107 to 115 of (SEQ ID NO: 17) (3 of 3), 73 (residues 114 to 122 of (SEQ ID NO: 17) (3 of 3) and 80 (residues 121 to 129 of (SEQ ID NO: 17) (2 of 3).

The sequences of the major antigenic regions of HCV type 3 differ considerably from those encoded by any of the type 1 or type 2 variants. The region bounded by peptides 13 to 22 (SEQ ID NO: 1) shows average homologies of 50% with HCV type 2 (SEQ ID NO: 3 and 4) variants and 67% with type 1 (SEQ ID NO: 7 and 8). Between peptides 32 to 42 (SEQ ID NO: 2), there are homologies of 39% with type 2 (SEQ ID NO: 5 and 6) and 58% with type 1 (SEQ ID NO: 10 and 11) variants. Thus, although similar regions of each NS-4 sequence are antigenic, the actual epitopes differ considerably between HCV types.

Discussion

The NS-4 region of HCV type 3 (SEQ ID NO: 16 and 17) shows considerable sequence divergence from other variants of HCV, that exceeds that found in the core, NS-3 or NS-5 regions previously analysed (Chan et al, 1992). The function of the protein encoded by this region of the HCV genome is unknown, and the consequences of this variability on virus replication and pathogenesis are unknown. The function of the NS-4 region in flaviviruses and pestiviruses is also poorly defined.

The degree of amino acid sequence variability, and the nature of the amino acid substitutions indicate that the major sites of antibody reactivity are also those of antigenic variability. This undoubtedly underlies the restricted cross-reactivity of HCV type 1 NS-4 encoded antigens with sera from individuals infected with different HCV types. Serological diagnosis of infection is currently based entirely on recombinant or synthetic oligopeptide sequences derived ultimately from HCV type 1 sequences (Choo et al., 1991). The serological response to infection is often very restricted in its initial stages, with antibody to only one of the recombinant antigens used for screening. Not only does this present difficulties with supplementary antibody tests, where reactivity to two HCV-encoded antigens is required for confirmation, but can lead to an increased probability of failing to detect early infection with HCV types 2 and 3.

Table 7 relates HCV typing determined by PCR, using type-specific sense primers (SEQ ID NO: 44 through 49) and the nontype-specific anti-sense primers (SEQ ID NO: 22 and 23) (Table 6), to results obtained using type-specific antigens (TSA) and shows good correlation for HCV 1–3 types.

TABLE 5

SEQUENCES OF NS-4 ENCODED ANTIGENS FOR (A) IMPROVED SEROLOGICAL DIAGNOSIS, AND (B) FOR SEROLOGICAL DISCRIMINATION OF INFECTION WITH DIFFERENT HCV TYPES

A)

| Type | Region 1 (1691–1708)* | Region 2 (1710–1728) |
|---|---|---|
| 3 | KPALVPDKEVLYQQYDEM†SEQ ID NO:1 | ECSQAAPYIEQAQVIAHQF SEQ ID NO:2 |
| 2‡ | RVVVTPDKEILYEAFDEM SEQ ID NO:3 | ECASKAALIEEGQRMAEML SEQ ID NO:5 |
|  | RAVIAPDKEVLYEAFDEM SEQ ID NO:4 | ECASRAALIEEGQRIAEML SEQ ID NO:6 |

B)

| Type | Region 1 (1691–1708) | Region 2 (1710–1728) |
|---|---|---|
| 3 | KPALVPDKEVLYQQYDEM SEQ ID NO:1 | ECSQAAPYIEQAQVIAHQF SEQ ID NO:2 |
| 2 | RVVVTPDKEILYEAFDEM SEQ ID NO:3 | ECASKAALIEEGQRMAEML SEQ ID NO:5 |
|  | RAVIAPDKEVLYEAFDEM SEQ ID NO:4 | ECASRAALIEEGQRIAEML SEQ ID NO:6 |
| 1 | KPAIIPDREVLYREFDEM SEQ ID NO:7 | ECSQHLPYIEGMLAEQF SEQ ID NO:10 |
|  | KPAVIPDREVLYREFDEM SEQ ID NO:8 | ECSQHLPYIEGALAEQF SEQ ID NO:11 |

TABLE 5-continued

SEQUENCES OF NS-4 ENCODED ANTIGENS FOR (A) IMPROVED SEROLOGICAL DIAGNOSIS, AND (B) FOR SEROLOGICAL DISCRIMINATION OF INFECTION WITH DIFFERENT HCV TYPES

*Amino acid positions numbered as in Choo et al., (1991).
†Amino acid codes: A: alanine: R: arginine: N: asparagine: D: aspartic acid: C: cysteine: Q: glutamine: E: glutamic acid: G: glycine: H: histidine: I: isoleucine: L: leucine: K: lysine: M: methionine: F: phenylalanine: P: proline: S: serine: T: threonine: W: tryptophan: Y: tyrosine: V: valine.
‡Alternative peptides, where there is variability within an HCV type..

TABLE 6

SEQUENCES OF OLIGONUCLEOTIDES SUITABLE FOR DIRECT DETECTION OF HCV TYPE 3 IN CLINICAL SPECIMENS BY POLYMERASE CHAIN REACTION

| Name | Region | Position of 5' base* | Pol.† | Sequences 5'–3'‡ |
|---|---|---|---|---|
| 007 | NS-4 | 5293 | – | AACTCGAGTATCCCACTGATGAAGTTCCACAT SEQ ID NO:32 |
| 220 | NS-4 | 5278 | – | CACATGTGCTTCGCCCAGAA SEQ ID NO:33 |
| Type 3:¶ | | | | |
| TS-3a | NS-4 | 5140 | + | GCCGCCCCATATATCGAACA SEQ ID NO:44 |
| TS-3b | NS-4 | 5161 | + | GCTCAGGTAATAGCCCACCA SEQ ID NO:45 |
| Type 2: | | | | |
| TS-2a | NS-4 | 5140 | + | AAAGCCGCCCTCATTGAGGA SEQ ID NO:46 |
| TS-2b | NS-4 | 5161 | + | GGGCAGCGGATGGCGGAGAT SEQ ID NO:47 |
| Type 1: | | | | |
| TS-1a | NS-4 | 5140 | + | CACTTACCGTACATCGAGCA SEQ ID NO:48 |
| TS-1b | NS-4 | 5161 | + | GGGATGATGCTCGCCGAGCA SEQ ID NO:49 |

*Position of 5' base relative to HCV genomic sequence in Choo et al., (1991).
†Orientation of primer sequence (+: sense: –: anti-sense)
‡Abbreviations: A: adenine, C: cytidine: G: guanidine, T: thymidine.
¶Type-specific sense primers for amplification of HCV types 3, 2 and 1 variants.

TABLE 7

COMPARISON OF SEROLOGICAL TYPING BY HCV-TSA WITH PCR

| PCR[a] | Number tested | TYPE-SPECIFIC ANTIBODY | | | | | | | |
|---|---|---|---|---|---|---|---|---|---|
| | | 1 | 2 | 3 | 1+2 | 1+3 | 2+3 | NTS[b] | NR[c] |
| 1 | 57 | 63 | — | — | — | 1 | — | 3 | 3 |
| 2 | 12 | — | 11 | — | — | — | 1 | 1 | 0 |
| 3 | 47 | 1 | — | 45 | — | 2 | — | 4 | 4 |
| Haem[d] | 27 | 11 | — | 4 | 1 | 4 | — | 3 | 4 |

[a]Genotype of HCV sequences amplified by PCR and typed by RFLP (McOmish et al 1992)
[b]NTS: No type-specific antibody detected
[c]NR: non-reactive with NS-4 peptides
[d]Samples from HCV-infected haemophiliacs. un-typed by PCR.

PART IV IDENTIFICATION OF HCV TYPE-4

Introduction

Investigations were carried out on sequence variations in the 5' non-coding region (5'NCR) of HCV samples from a variety of worldwide geographical locations (FIG. 13), and also in the core region (FIGS. 15A and 15B). Phylogenetic analysis (FIGS. 14 and 16) revealed a new distinct HCV type which we refer to herein as HCV-4.

Methods

Samples. RNA was extracted from plasma samples that were repeatedly reactive on second generation screening assays for HCV, and which were either confirmed (significant reactivity with two or more antigens in the Chiron recombinant immunoblot assay; Chiron Corporation, Emeryville, Calif., USA) or indeterminate (reactive with only one antigen) from blood donors and patients with NANBH. Most of the samples containing sequences that differed substantially fcm known HCV types came from Egypt (EG 1-33). Others came from Holland (NL-26), Hong Kong (HK 1-4), Iraq (IQ-48) and XX (xx-(6).

Sequence determination. HCV sequences were reverse transcribed and amplified with primers matching conserved regions in the 5'NCR as previously described [1]. For analysis of the core region. RNA was reverse transcribed using a primer of sequence CA(T/C)GT(A/G) AGGGTATCGATGAC (SEQ ID NO: 50) (5' base: xxx, numbered as in [20]). CDNA was amplified using this primer and a primer in the 5'NCR of sequence ACTGCCT-GATAGGGTGCTTGCGAG (SEQ ID NO: 51) (5' base: –54). The second PCR used primers of sequences AGGTCTCGTAGACCGTGCATCATG (SEQ ID NO: 52) (5' base: –21) and TTGCG(G/T/C)GACCT(A/T) CGCCGGGGTC (SEQ ID NO: 53) (5' base: xxx). Amplified DNA in both regions was directly sequenced as described previously (reference 1a).

Sequence analysis. Sequences were aligned using the CLUSTAL program in the University of Wisconsin GCG package (reference 6). Phylogenetic trees were constructed by the DNAML program in the PHYLIP package of Felsenstein (version 3.4, June 1991; (reference 9), using the global option. RNA secondary structures in the 5'NCR of 4 representative HCV variants (refs) were predicted using the program FOLD. Three predictions were made from each sequence between nucleotides −341 to −1, −341 to +300, and −341 to +900 to allow for possible long range interactions. Comparison of the predicted conformations for each sequence over the different lengths showed that only relatively small scale features, such as the stem/loop analysed in the Results were at all conserved (data not shown).

All sequences reported in this part have been submitted to GenBank.

Results

Figure 13B:
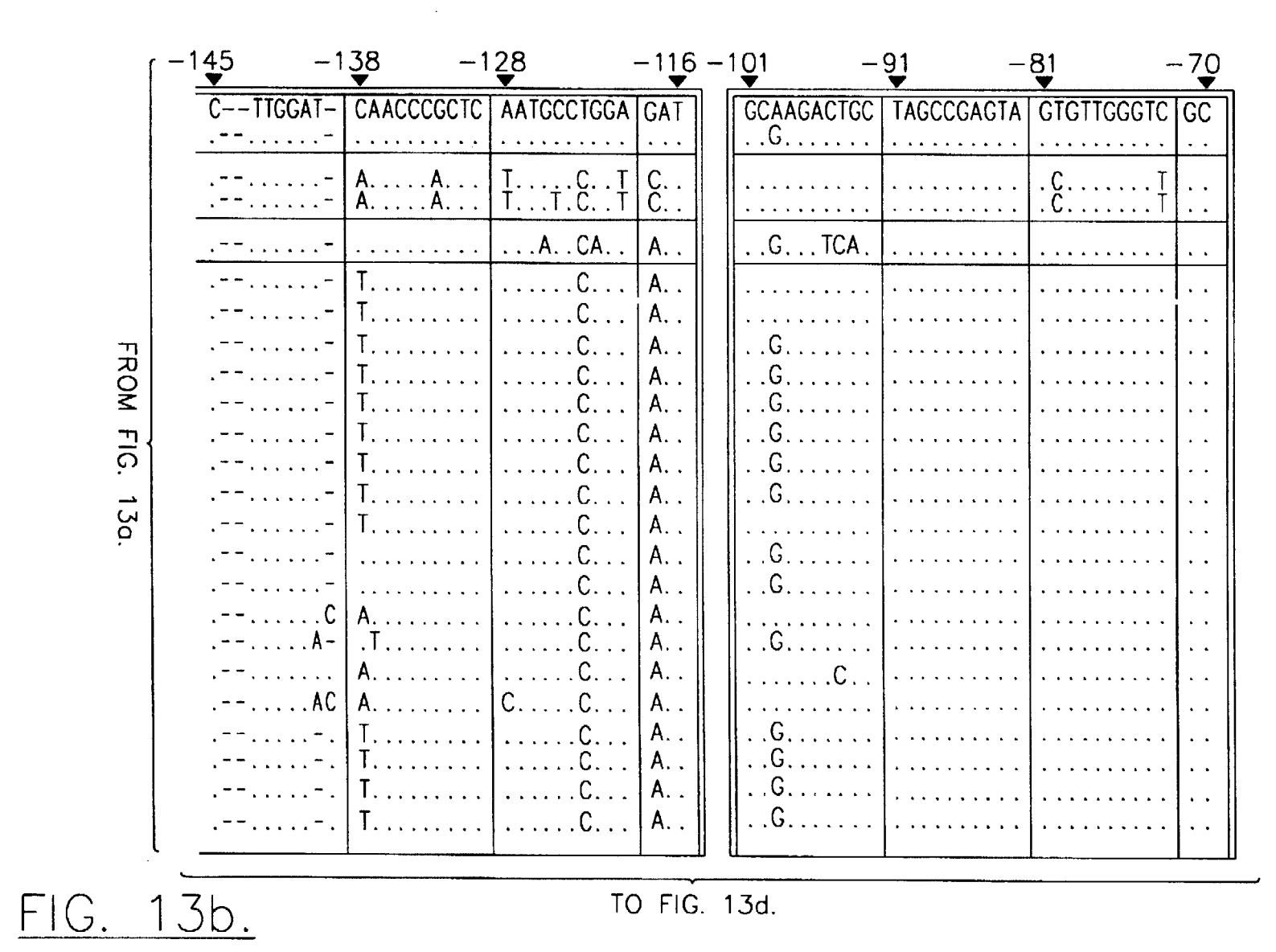
Figure 13C:
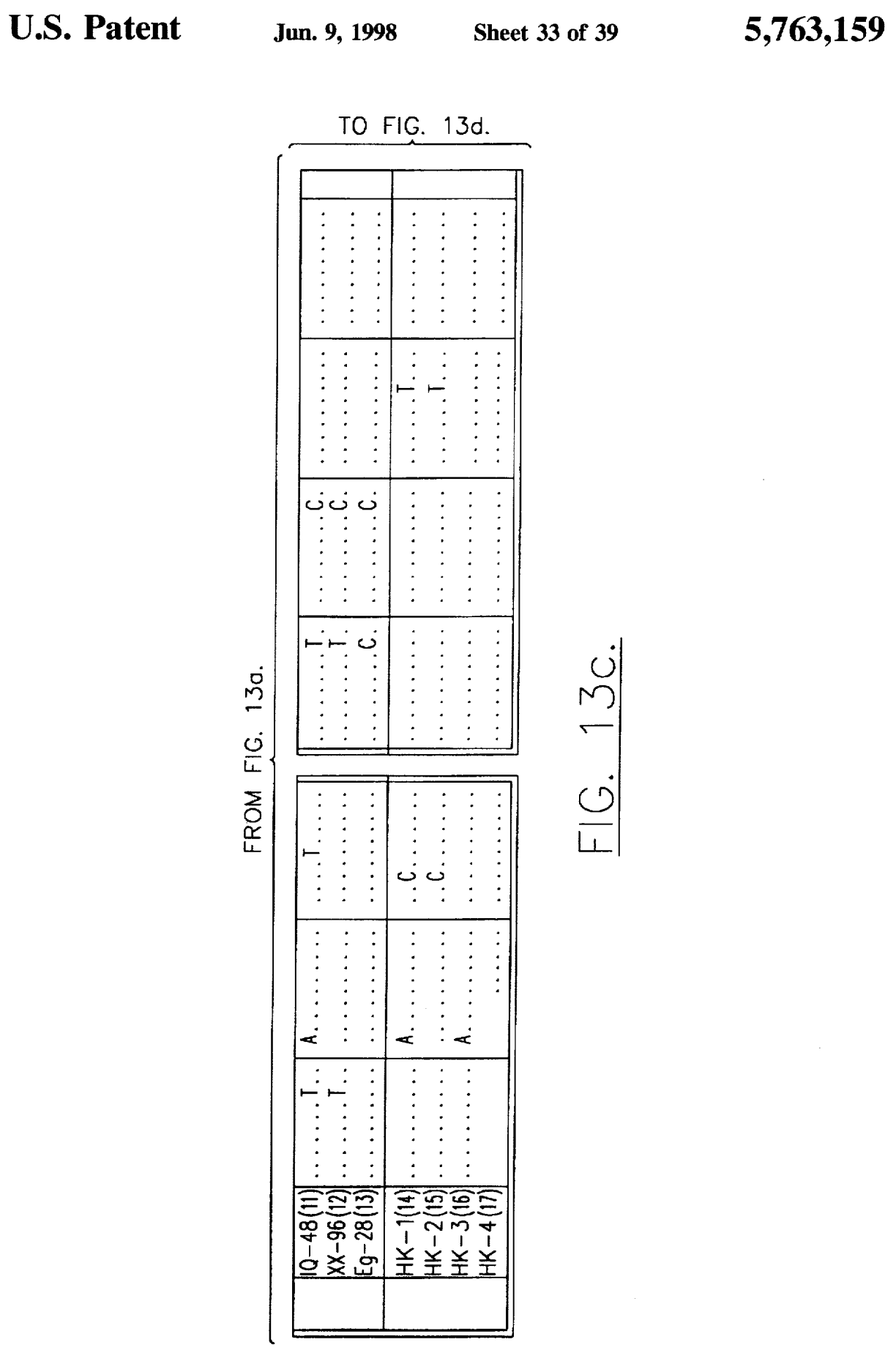
Figure 13D:
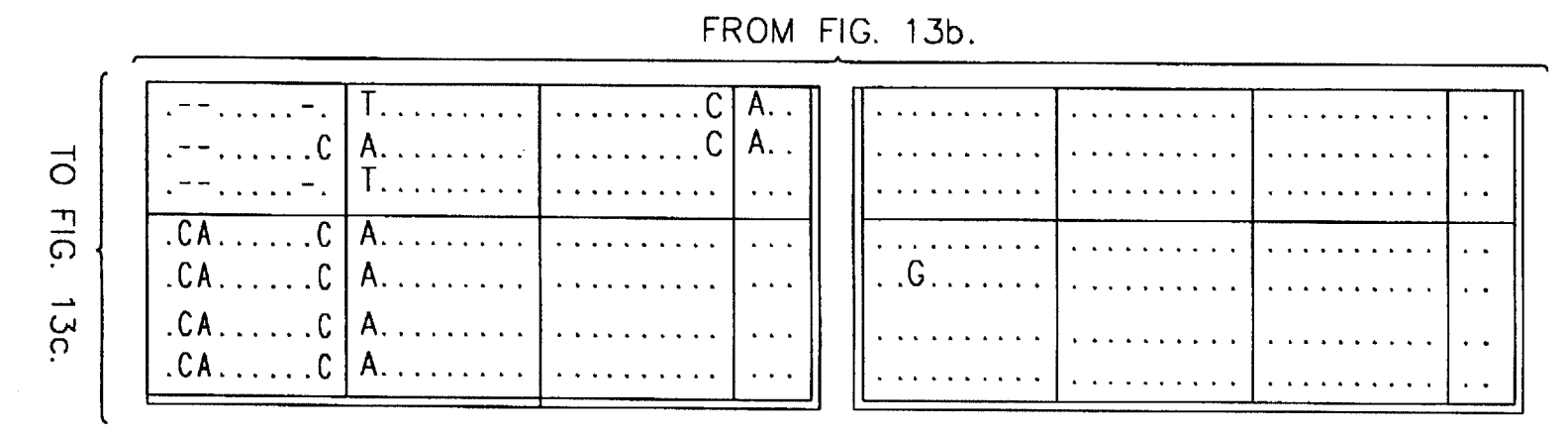
Figure 14:
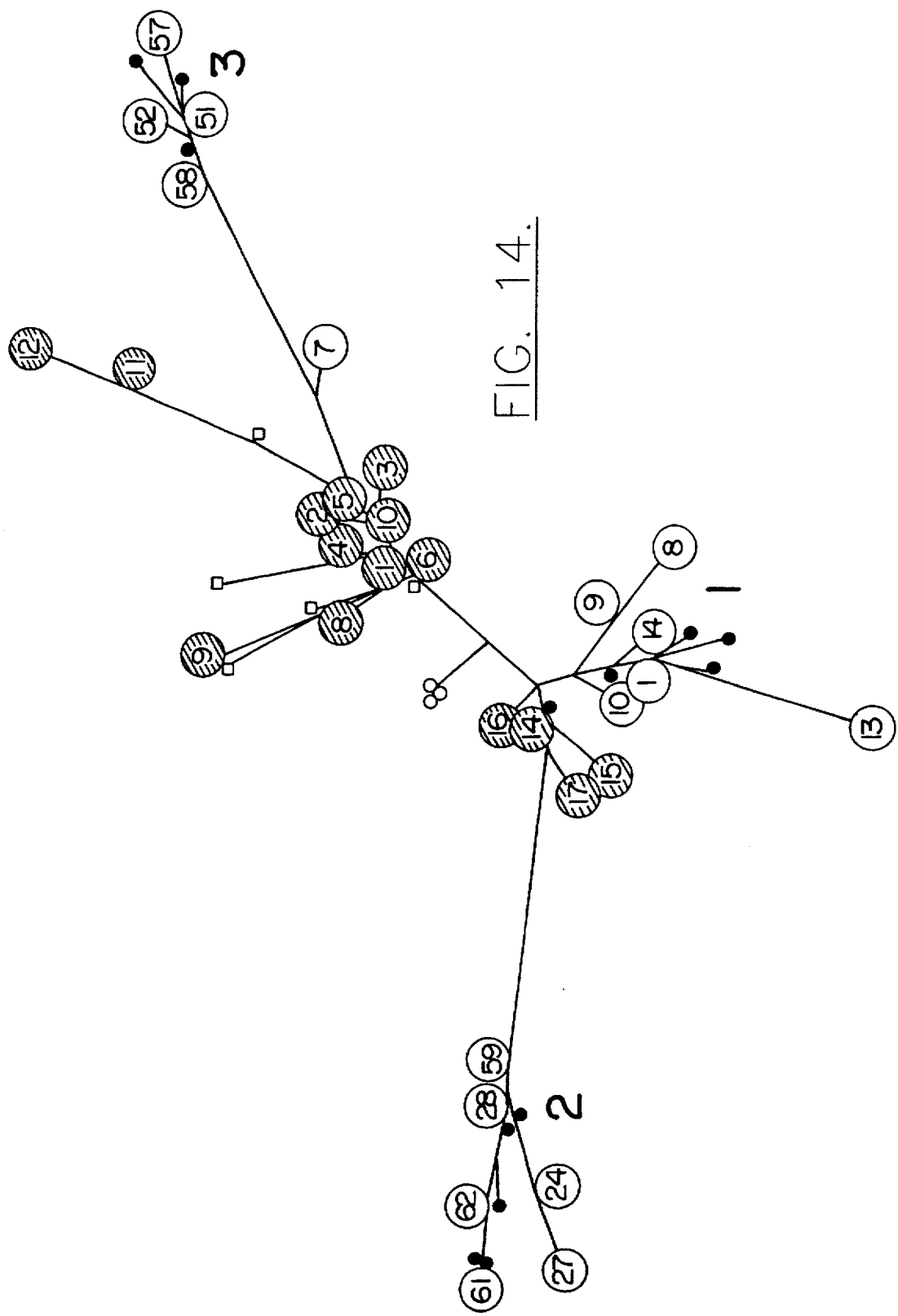
FIG. 14 is a phylogenetic analysis of the 5'NCR region using the maximum likelihood algorithm, shown as an unrooted tree. Sequences 1–17 in solid circles are numbered as in FIG. 13; previously published sequences numbered as in table 1 of (992). Scottish blood donor sequences Eb-1–Eb-12 numbered 51–62 in hollow circles. For clarity, only non-identical sequences are shown in tree; e.g. Sequence 1 corresponds to those found in samples Eg-16 and Eg-29 etc.

Divergent 5'NCR sequences (SEQ ID NO: 58). Several sequences in the 5'NC region detected in samples of blood donors from Saudi Arabia, Holland and Hong Kong, and from NANBH patients in Iraq and xxx differed substantially from those found in Scottish blood donors-and those reported elsewhere (FIG. 13). Instead of showing the well characterised nucleotide substitutions that distinguish HCV types 1, 2 and 3 from each other, a new set of sequence differences were observed in the new variants that appeared to place them outside the existing system of virus classification. This can be more simply represented by reconstructing a phylogeny of the sequences and presenting the results as an evolutionary tree (FIG. 14). This analysis confirms that sequences 1–10 cluster separately from the variants previously typed as 1, 2 and 3 (SEQ ID NO: 12). For convenience we will refer to sequences within this new group as HCV type 4 (SEQ ID NO: 18). Mean distances within type 4 and between type 4 and the other HCV types in the 5'NCR were comparable to those previously described for type 1–3. Although sequences within type 4 (SEQ ID NO: 18) are relatively closely grouped, sequences 11, 12 and 13 differ considerably from any of the known types.

Using this phylogenetic tree, it can be seen that the majority of previously Published 5'NCR sequences can be readily identified as types 1, 2 or 3 (SEQ ID NO: 12). Furthermore, almost all of the sequences from Zaire (shown as hollow squares) cluster closely within type 4, suggesting a wider distribution in Africa. However, a further complication is that three identical sequences obtained from South African patients appeared distinct from both the type 1 and the type 4 group, and may represent yet another HCV type.

Figure 16:
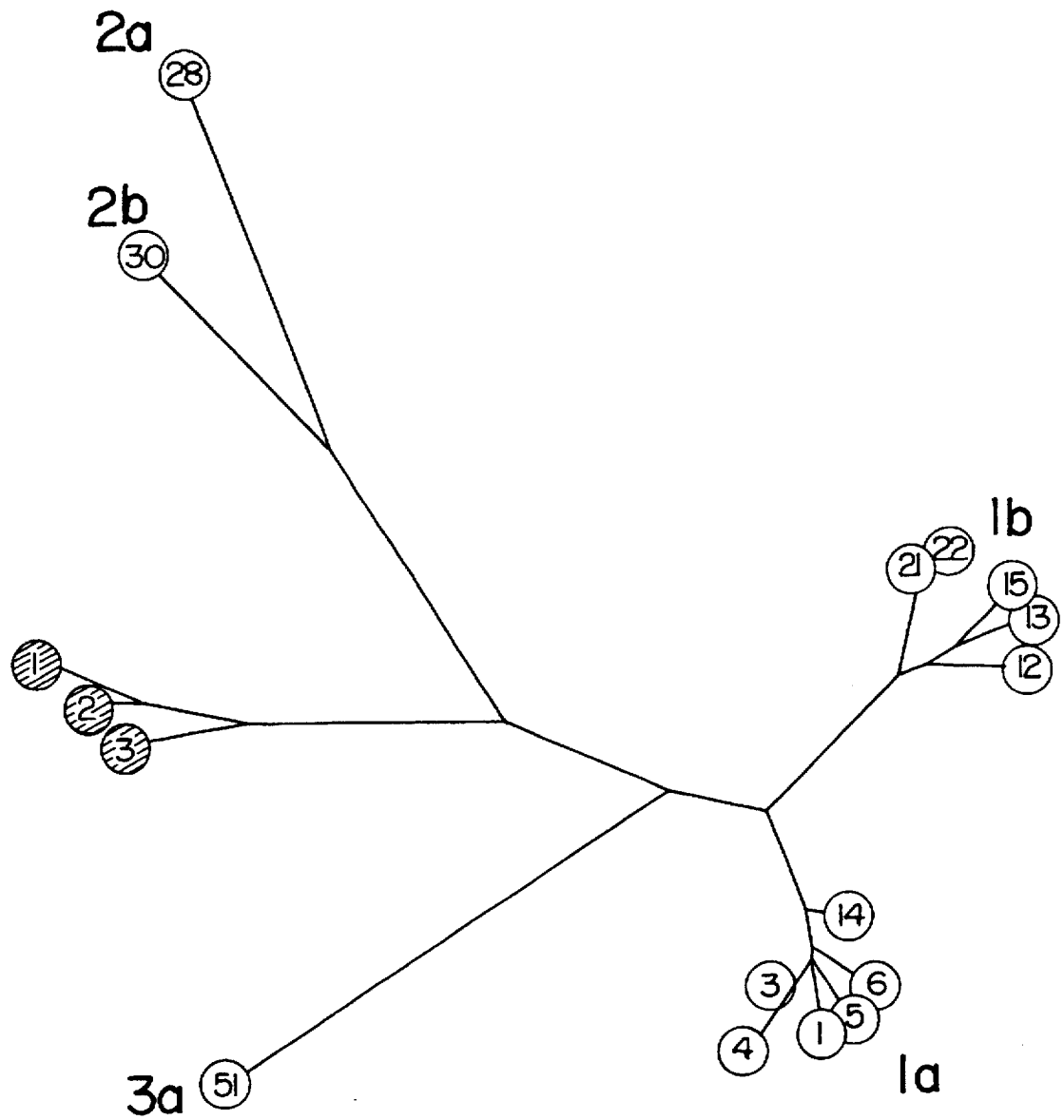
FIG. 16 is a phylogenetic analysis of part of the core region using the maximum likelihood algorithm, shown as an unrooted tree. Sequences are numbered as in FIG. 14; sequence 30 is that of HC-J8 (Okamato et al. Virology 188: 331–341)

RNA from three representative type 4 variants (Eg 29, 33, 21; corresponding to 5'NCR sequences nos. 1–3) was amplified using primers in the core region of HCV polyprotein. All three sequences differed considerably at both the nucleotide (SEQ ID NO: 20) and amino acid (SEQ ID NO: 21) level from HCV types 1, 2 and 3 (SEQ ID NO: 19 and residues 1 to 89 of SEQ ID NO: 15, respectively) (FIG. 15A/B). Phylogenetic analysis of these sequences and those previously analysed indicated that they formed a separate, relatively homogeneous group distinct from the other types (FIG. 16). Reconstructed nucleotide distances between type 4 (SEQ ID NO: 20) and types 1, 2 and 3 (SEQ ID NO: 19) were comparable to those that exist between the three known HCV types of HCV. Although most of the nucleotide sequence differences were silent, there were between 4 and 9 amino acid differences between the new variants (SEQ ID NO: 21) and other types.

PART V HCV TYPING

Introduction

In view of the sequence variations between HCV types 1, 2, 3 and 4 differences in restriction enzyme cleavage sites exist, leading to different endonuclease cleavage patterns. This technique was used to identify HCV genotypes in blood samples from a variety of sources worldwide.

(A) Typing of HCV1-3
METHODS

Serum Samples: Samples from blood donors in six countries, Scotland, Finland, Netherlands, Hong Kong and Australia and Japan, were available from routine 2nd Generation anti-HCV ELISA screening (Ortho or Abbott). Donor samples that were repeatedly reactive in the above tests were further investigated using a supplementary test (Ortho RIBA: Finland, Netherlands, Australia, Egypt, Abbott Matrix: Hong Kong) or samples were titred for anti-HCV by ELISA (Japan). Samples that were positive (significant reactivity with two or more HCV antigens (1+ to 4+) or indeterminate (reactivity with one antigen only) in the RIBA test or had a titer of >X 4096 by ELISA (Japan only) were tested for viral RNA by Polymerase Chain Reaction (PCR).

RNA PCR: PCR for the detection of HCV RNA was carried out as previously described by Chan et al (reference 1a) using primers in the 5'non-coding region (5'NCR) in a nested PCR, with primers 209 (SEQ ID NO: 22)/939 (SEQ ID NO: 24) and 211 (SEQ ID NO: 24)/940 (SEQ ID NO: 23) (SEQ ID NO: 23) (5) (SEQ ID NO: 25) in first and second reactions respectively.

HCV TYPING

The existence of relatively conserved patterns of substitutions in the 5'NCR that are characteristic of different HCV types provide useful signature sequences for identification of HCV genotypes. Having compared large numbers of different HCV type 1, 2 and 3 sequences, we developed a method that differentiated HCV types 1–3 by restriction endonuclease cleavage of amplified DNA. However, the 19 type 4 sequences would appear as type 1 (electrophoretic types Aa and Ab), and for concurrent studies it has been necessary to modify the conditions to identify the new HCV type. All type 4 sequences showed a T→C change at position −167 (position 78 in SEQ ID NO: 18) that creates a novel HinfI site that is absent in all type 1 (and type 2) sequences. In combination with ScrFI, and HaeIII/RsaI, it has now proved possible to identify the new type reliably in numerous countries in the Middle East and elsewhere.

RESULTS

The results are summarised in Table 8 for HCV types 1, 2 and 3. The Egyptian samples gave aberrant restriction patterns on the single ScrFI digest and were identified as type 4.

TABLE 8

PREVALENCE OF HCV TYPES IN DIFFERENT COUNTRIES

| COUNTRY | HCV TYPES (%) | | |
|---|---|---|---|
| | HCV-1 | HCV-2 | HCV-3 |
| Scotland | 86 (51%) | 21 (13%) | 60 (36%) |
| Finland | 3 (25%) | 5 (42%) | 4 (33%) |
| Netherlands | 18 (60%) | 7 (23%) | 5 (17%) |
| Hong Kong | 22 (63%) | 0 (0%) | 0 (0%) |
| Australia | 13 (57%) | 3 (13%) | 7 (30%) |
| Japan | 31 (77%) | 9 (23%) | 0 (0%) |
| Egypt | 0 (0%) | 0 (0%) | 0 (0%) |

(B) MODIFICATION OF PCR-BASED TYPING ASSAY TO DETECT INFECTION WITH HCV TYPE 4 IN CLINICAL SPECIMENS

Methods

Extraction of RNA. RNA was extracted from 100 ul aliquots of plasma of non-A, non-B patients by addition of 1 ml RNAzol solution (2M guanidinium thiocyanate, 12.5 mM sodium citrate [pH7.0], 0.25% w/v N-lauroylsarcosine, 0.05M 2-mercaptoethanol, 100 mM sodium acetate [pH 4.0], 50% w/v water saturated phenol) as previously described (Chomczynski et al. 1987), and mixed until precipitate dissolved. After addition of 100 ul chloroform, each sample was spun for 5 minutes at 14000×g and the aqueous phase re-extracted with 0.5 ml chloroform. RNA was precipitated by addition of an equal volume of isopropanol and incubation at −20° C. for at least 1 hour. An RNA pellet was produced by centrifugation at 14000×g for 15 minutes at 4° C., washed in 1 ml 70% cold ethanol solution, dried and resuspended in 20 ul diethylpyrocarbonate treated distilled water. Of the 100 directly extracted samples, a total of 19 were PCR-negative (see below). Two ml volumes of the negative samples were ultracentrifuged at 200 000×g for 2 hours and the pellet re-extracted as described above. Extraction from the larger volume of plasma yielded an additional 3 positive samples (numbers 66, 80, 85).

Figure 17A:
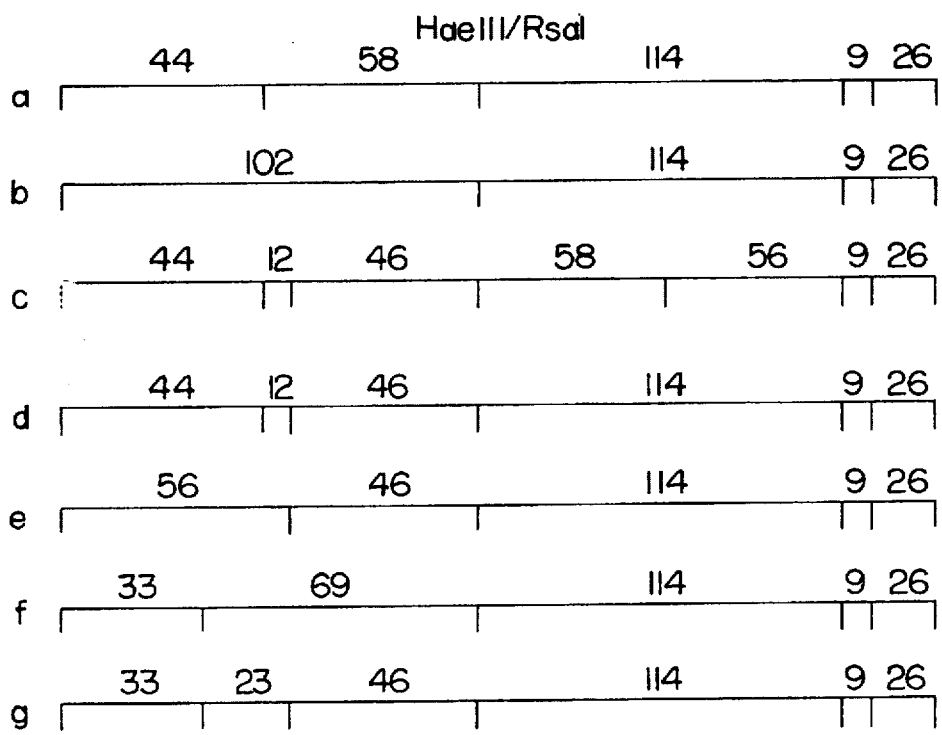
FIGS. 17(a) and 17(b) show cleavage patterns for A) HaeIII/RsaI and B) ScrFI in 5'NCR.
Figure 17B:
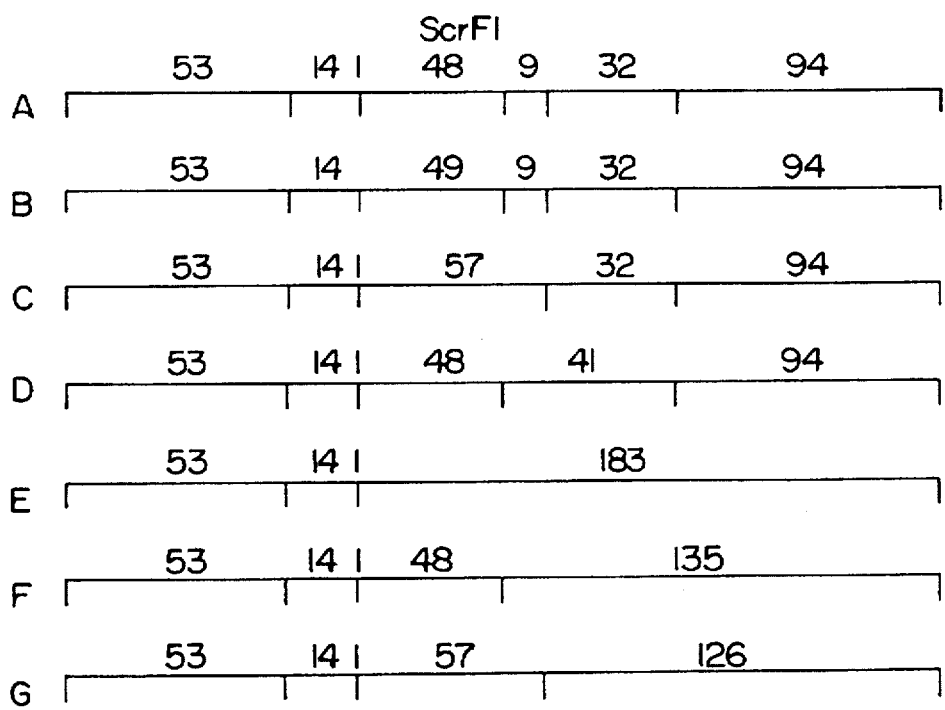

PCR and typing. RNA was reverse transcribed with primer 940 (SEQ ID NO: 25) and cDNA amplified in a two stage nested PCR reaction with primers 940 (SEQ ID NO: 25)/939 (SEQ ID NO: 24), followed by 209 (SEQ ID NO: 22)/211 (SEQ ID NO: 23) as previously described (Chan et al. 1992). PCR product was radiolabelled with [$^{35}$S]-dATP analysed by restriction endonuclease cleavage (McOmish et al. Transfusion, 32:no.11 1992). Samples were cleaved with ScrFI and a combination of HaeIII/RsaI in two separate reactions to identify HCV types 1/4, 2, 3. FIG. 17 shows endonuclease cleavage patterns. HCV types 1 and 4 were differentiated by a third reaction with HinfI (see Results). Two samples yielded restriction patterns that were different from those of the four known types of HCV and were analysed further by direct sequence analysis of the amplified DNA (Chan et al. 1992). These two samples contained 5′NCR sequences distinct from those of known HCV types and currently remain unclassified.

RESULTS

Modification of RFLP method to identify HCV type 4.

Previous sequence analysis in the 5′NCR of HCV amplified from plasma of Egyptian blood donors revealed a relatively homogeneous group of novel sequence variants in both the 5′NCR (SEQ ID NO: 18) and core (SEQ ID NO: 20 and 21) region which were as distinct from HCV types 1, 2 and 3 (SEQ ID NO: 19 and residues 1 to 89 of (SEQ ID NO: 15) as these latter types were from each other (see previous submission). This new group was designated as HCV type 4.

Comparison of cleavage patterns of type 4 sequences with those of type RFLP analysis of the previously identified type 4 sequences produced a distribution of electropherotypes with ScrFI and HaeIII/RsaI similar to that HCV type 1 (Table 9). Type 1 sequences yielded 9 patterns of aA/B, 35 of bA/B and 1 bC. With these enzymes alone, type 4 sequences were thus indistinguishable from type 1 (14 aA/B, 4 bA/B). However, type 1 and type 4 sequences consistently differ in the number of HinfI sites. All 18 type 4 sequences contain one or two potential cleavage sites (producing patterns band c; table 5) while none are found in any of the 45 type 1 sequences analysed (pattern a). One of the type 4 sequences was further differentiated from type 1 and other HCV types by the loss of a restriction site for RsaI, leading to a new pattern of bands designated h (44, 172, 9, 26; first column, Table 9). Finally, a single sequence, EG-28 lost two sites to produce bands of 216, 9, and 26 bps (pattern i; Table 9). This sequence was distinct from that of any of the known HCV types (including type 4) and is shown in the table in the column labelled U (unclassified)

Typing of study subjects. RNA was extracted from 100 samples of patients with NANB hepatitis and amplified with primers in the 5′NCR. Of these, 84 were PCR positive, and enabled HCV typing to be carried out by RFLP. This was initially carried out with HaeIII/RsaI and ScrFI, and allowed the identification of 10 type 2 and 10 type 3 variants (Table 10). Samples showing electrophoretic patterns aA/B or bA/B were further analysed by cleavage with hinfI, yielding 38 samples with pattern a, thus identified as type 1, 22 with pattern b and 2 with pattern c, both identified as type 4. Finally, two samples showed the unusual cleavage patterns h and i with HaeII/RsaI and pattern b with HinfI, and were therefore directly sequenced. These two sequences were similar to each other but were unlike any of the known HCV types, and also distinct from EG-28, the other sequence showing pattern i with HaeIII/RsaI (Table 10). As they cannot be currently classified, they will be referred to as type U.

TABLE 9

PREDICTED CLEAVAGE PATTERNS OF PUBLISHED 5′NCR SEQUENCES OF HCV TYPES 1, 2, 3 AND 4 WITH RsaI/HaeIII, ScrFI AND HinfI Predicted cleavage pattern[a]

| HaeIII/ RsaI | ScrFI | HinfI | 1 | 2 | 3 | 4 | U[b] |
|---|---|---|---|---|---|---|---|
| a | A/B | a[c] | 9 | — | — | — | — |
| b | A/B | a | 35 | — | — | — | — |
| b | C | a | 1 | — | — | — | — |
| a | A/B | b[d] | — | — | — | 13 | — |
| a | A/B | c[e] | — | — | — | 1 | — |
| b | A/B | b | — | — | — | 4 | — |
| c | D | a | — | 5 | — | — | — |
| d | D | a | — | 1 | — | — | — |
| d | E | a | — | 2 | — | — | — |
| e | D | a | — | 1 | — | — | — |
| e | E | a | — | 1 | — | — | — |
| f | G | b | — | — | 14 | — | — |
| f | G | c | — | — | 1 | — | — |
| g | G | b | — | — | 8 | — | — |
| h[f] | A/B | b | — | — | — | 1 | — |
| i[g] | A/B | b | — | — | — | — | 1 |

[a]Cleavage patterns designated for HaeIII/RsaI and ScrFI as described previously (McOmish et al. 1992).
[b]Cleavage pattern of an HCV variant of undesigned type
[c]Pattern a: uncleaved by HinfI
[d]Pattern b: DNA cleaved to generate two fragments of sizes 107 and 142 bps (in order 5′-3′)
[e]Pattern c: DNA cleaved to generate three fragments of 56, 51 and 142 bps
[f]New cleavage pattern for HaeIII/Rsai designated h (bands of 44 bps, 172 bps, 9 bps, 26 bps)
[g]New cleavage pattern for HaeIII/Rsai designated i (216 bps, 9 bps, 26 bps)

TABLE 10

IDENTIFICATION OF HCV TYPES 1–4 IN STUDY SUBJECTS BY RFLP ANALYSIS OF 5′NCR SEQUENCES WITH RsaI/HaeIII, ScrFI AND HinfI Observed cleavage pattern

| HaeIII/ RsaI | ScrFI | HinfI | 1 | 2 | 3 | 4 | U[a] |
|---|---|---|---|---|---|---|---|
| a | A/B | a | 2 | — | — | — | — |
| b | A/B | a | 36 | — | — | — | — |

TABLE 10-continued

IDENTIFICATION OF HCV TYPES 1-4 IN
STUDY SUBJECTS BY RFLP ANALYSIS OF 5'NCR
SEQUENCES WITH RsaI/HaeIII, ScrFI AND HinfI Observed cleavage pattern

| HaeIII/ | | | Inferred HCV type | | | | |
|---|---|---|---|---|---|---|---|
| RsaI | ScrFI | HinfI | 1 | 2 | 3 | 4 | U* |
| a | A/B | b | — | — | — | 16 | — |
| a | A/B | c | — | — | — | 2 | — |
| b | A/B | b | — | — | — | 6 | — |
| c | D | n.d. | — | 7 | — | — | — |
| d | E | n.d. | — | 3 | — | — | — |
| f | G | n.d. | — | — | 7 | — | — |
| g | G | n.d. | — | — | 3 | — | — |
| h | A/B | b | — | — | — | — | 1 |
| i | A/B | b | — | — | — | — | 1 |
| TOTALS | | | 38 | 10 | 10 | 24 | 2 |

*Two samples yielded unusual restriction patterns with HaeIII/RsaI (h,i). Sequence analysis of the 5'NCR placed them outside existing HCV classification (samples IQ-48, EG-96).

PART VI Expression and Assay etc. Techniques

The present invention also provides expression vectors containing the DNA sequences as herein defined, which vectors being capable, in an appropriate host, of expressing the DNA sequence to produce the peptides as defined herein.

The expression vector normally contains control elements of DNA that effect expression of the DNA sequence in an appropriate host. These elements may vary according to the host but usually include a promoter, ribosome binding site, translational start and stop sites, and a transcriptional termination site. Examples of such vectors include plasmids and viruses. Expression vectors of the present invention encompass both extrachromosomal vectors and vectors that are integrated into the host cell's chromosome. For use in *E. coli*, the expression vector may contain the DNA sequence of the present invention optionally as a fusion linked to either the 5'- or or 3'-end of the DNA sequence encoding, for example, B-galactosidase or to the 3'-end of the DNA sequence encoding, for example, the trp E gene. For use in the insect baculovirus (AcNPV) system, the DNA sequence is optionally fused to the polyhedrin coding sequence.

The present invention also provides a host cell transformed with expression vectors as herein defined.

Examples of host cells of use with the present invention include prokaryotic and eukaryotic cells, such as bacterial, yeast, mammalian and insect cells. Particular examples of such cells are *E. coli, S. cerevisiae, P. pastoris*. Chinese hamster ovary and mouse cells, and *Spodoptera frugiperda* and *Tricoplusia ni*. The choice of host cell may depend on a number of factors but, if post-translational modification of the HCV viral peptide is important, then an eukaryotic host would be preferred.

The present invention also provides a process for preparing a peptide as defined herein which comprises isolating the DNA sequence, as herein defined, from the HCV genome, or synthesising DNA sequence encoding the peptides as defined herein, or generating a DNA sequence encoding the peptide, inserting the DNA sequence into an expression vector such that it is capable, in an appropriate host, of being expressed, transforming host cells with the expression vector, culturing the transformed host cells, and isolating the peptide.

The DNA sequence encoding the peptide may be synthesised using standard procedures (Gait, *Oligonucleotide Synthesis: A Practical Approach*, 1984, Oxford, IRL Press).

The desired DNA sequence obtained as described above may be inserted into an expression vector using known and standard techniques. The expression vector is normally cut using restriction enzymes and the DNA sequence inserted using blunt-end or staggered-end ligation. The cut is usually made at a restriction site in a convenient position in the expression vector such that, once inserted, the DNA sequences are under the control of the functional elements of DNA that effect its expression.

Transformation of an host cell may be carried out using standard techniques. Some phenotypic marker is usually employed to distinguish between the transformants that have successfully taken up the expression vector and those that have not. Culturing of the transformed host cell and isolation of the peptide as required may also be carried out using standard techniques.

The peptides of the present invention may be prepared by synthetic methods or by recombinant DNA technology. The peptides are preferably synthesized using automatic synthesizers.

Antibody specific to a peptide of the present invention can be raised using the peptide. The antibody may be polyclonal or monoclonal. The antibody may be used in quality control testing of batches of the peptides; purification of a peptide or viral lysate; epitope mapping; when labelled, as a conjugate in a competitive type assay, for antibody detection; and in antigen detection assays.

Polyclonal antibody against a peptide of the present invention may be obtained by injecting a peptide, optionally coupled to a carrier to promote an immune response, into a mammalian host, such as a mouse, rat, sheep or rabbit, and recovering the antibody thus produced. The peptide is generally administered in the form of an injectable formulation in which the peptide is admixed with a physiologically acceptable diluent. Adjuvants, such as Freund's complete adjuvant (FCA) or Freund's incomplete adjuvant (FIA), may be included in the formulation. The formulation is normally injected into the host over a suitable period of time, plasma samples being taken at appropriate intervals for assay for anti-HCV viral antibody. When an appropriate level of activity is obtained, the host is bled. Antibody is then extracted and purified from the blood plasma using standard procedures, for example, by protein A or ion-exchange chromatography.

Monoclonal antibody against a peptide of the present invention may be obtained by fusing cells of an immortalising cell line with cells which produce antibody against the viral or topographically related peptide, and culturing the fused immortalised cell line. Typically, a non-human mammalian host, such as a mouse or rat, is inoculated with the peptide. After sufficient time has elapsed for the host to mount an antibody response, antibody producing cells, such as the splenocytes, are removed. Cells of an immortalising cell line, such as a mouse or rat myeloma cell line, are fused with the antibody producing cells and the resulting fusions screened to identify a cell line, such as a hybridoma, that secretes the desired monoclonal antibody. The fused cell line may be cultured and the monoclonal antibody purified from the culture media in a similar manner to the purification of polyclonal antibody.

Diagnostic assays based upon the present invention may be used to determine the presence or absence of HCV infection. They may also be used to monitor treatment of such infection, for example in interferon therapy.

In an assay for the diagnosis of viral infection, there are basically three distinct approaches that can be adopted involving the detection of viral nucleic acid, viral antigen or viral antibody. Viral nucleic acid is generally regarded as the best indicator of the presence of the virus itself and would identify materials likely to be infectious. However, the detection of nucleic acid is not usually as straightforward as the detection of antigens or antibodies since the level of target can be very low. Viral antigen is used as a marker for the presence of virus and as an indicator of infectivity. Depending upon the virus, the amount of antigen present in a sample can be very low and difficult to detect. Antibody detection is relatively straightforward because, in effect, the host immune system is amplifying the response to an infection by producing large amounts of circulating antibody. The nature of the antibody response can often be clinically useful, for example IgM rather than IgG class antibodies are indicative of a recent infection, or the response to a particular viral antigen may be associated with clearance of the virus. Thus the exact approach adopted for the diagnosis of a viral infection depends upon the particular circumstances and the information sought. In the case of HCV, a diagnostic assay may embody any one of these three approaches.

In an assay for the diagnosis of HCV involving detection of viral nucleic acid, the method may comprise hybridising viral RNA present in a test sample, or cDNA synthesised from such viral RNA, with a DNA sequence corresponding to the nucleotide sequences of the present invention or encoding a peptide of the invention, and screening the resulting nucleic acid hybrids to identify any HCV viral nucleic acid. The application of this method is usually restricted to a test sample of an appropriate tissue, such as a liver biopsy, in which the viral RNA is likely to be present at a high level. The DNA sequence corresponding to a nucleotide sequence of the present invention or encoding a peptide of the invention may take the farm of an oligonucleotide or a CDNA sequence optionally contained within a plasmid. Screening of the nucleic acid hybrids is preferably carried out by using a labelled DNA sequence. Preferably the peptide of the present invention is part of an oligonucleotide wherein the label is situated at a sufficient distance from the peptide so that binding of the peptide to the viral nucleic acid is not interfered with by virtue of the label being too close to the binding site. One or more additional rounds of screening of one kind or another may be carried out to characterise further the hybrids and thus identify any HCV viral nucleic acid. The steps of hybridisation and screening are carried out in accordance with procedures known in the art.

The present invention also provides a test kit for the detection of HCV viral nucleic acid, which comprises
i) a labelled oligonucleotide comprising a DNA sequence of the present invention or encoding a peptide of the present invention; and
ii) washing solutions, reaction buffers and a substrate, if the label is an enzyme.

Advantageously, the test kit also contains a positive control sample to facilitate in the identification of viral nucleic acid.

In an assay for the diagnosis of HCV involving detection of viral antigen or antibody, the method may comprise contacting a test sample with a peptide of the present invention or a polyclonal or monoclonal antibody against the peptide and determining whether there is any antigen-antibody binding contained within the test sample. For this purpose, a test kit may be provided comprising a peptide, as defined herein, or a polyclonal or monoclonal antibody thereto and means for determining whether there is any binding with antibody or antigen respectively contained in the test sample. The test sample may be taken from any of the appropriate tissues and physiological fluids mentioned above for the detection of viral nucleic acid. If a physiological fluid is obtained, it may optionally be concentrated for any viral antigen or antibody present.

A variety of assay formats may be employed. The peptide can be used to capture selectively antibody against HCV from solution, to label selectively the antibody already captured, or both to capture and label the antibody. In addition, the peptide may be used in a variety of homogeneous assay formats in which the antibody reactive with the peptide is detected in solution with no separation of phases.

The types of assay in which the peptide is used to capture antibody from solution involve immobilization of the peptide on to a solid surface. This surface should be capable of being washed in some way. Examples of suitable surfaces include polymers or various types (moulded into microtitre wells; beads; dipsticks of various types; aspiration tips; electrodes; and optical devices), particles (for example latex; stabilized red blood cells; bacterial or fungal cells; snores; gold or other metallic or metal-containing sols; and proteinaceous colloids) with the usual size of the particle being from 0.02 to 5 microns, membranes (for example of nitrocellulose; paper; cellulose acetate; and high porosity/high surface area membranes of an organic or inorganic material).

The attachment of the peptide to the surface can be by passive adsorption from a solution of optimum composition which may include surfactants, solvents, salts and/or chaotropes; or by active chemical bonding. Active bonding may be through a variety of reactive or activatible functional groups which may be exposed on the surface (for example condensing agents; active acid esters, halides and anhydrides; amino, hydroxyl, or carboxyl groups; sulphydryl groups; carbonyl groups; diazo groups; or unsaturated groups). Optionally, the active bonding may be through a protein (itself attached to the surface passively or through active bonding), such as albumin or casein, to which the viral peptide may be chemically bonded by any of a variety of methods. The use of a protein in this way may confer advantages because of isoelectric point, charge, hydrophilicity or other physico-chemical property. The viral peptide may also be attached to the surface (usually but not necessarily a membrane) following electrophoretic separation of a reaction mixture, such as immunoprecipitation.

After contacting (reacting) the surface bearing the peptide with a test sample, allowing time for reaction, and, where necessary, removing the excess of the sample by any of a variety of means, (such as washing, centrifugation, filtration, magnetism or capillary action) the captured antibody is detected by any means which will give a detectable signal. For example, this may be achieved by use of labelled molecule or particle as described above which will react with the captured antibody (for example protein A or protein G and the like; anti-species or anti-immunoglobulin-subtype: rheumatoid factor: or antibody to the peptide, used in a competitive or blocking fashion), or any molecule containing an epitope contained in the peptide.

The detectable signal may be optical or radioactive or physico-chemical and may be provided directly by labelling the molecule or particle with, for example, a dye, radiolabel, electroactive species, magnetically resonant species or fluorochore, or indirectly by labelling the molecule or particle with an enzyme itself capable of giving rise to a measurable change of any sort. Alternatively the detectable signal may be obtained using, for example, agglutination, or through a diffraction or birefringent effect if the surface is in the form of particles.

Assays in which a peptide itself is used to label an already captured antibody require some form of labelling of the peptide which will allow it to be detected. The labelling may be direct by chemically or passively attaching for example a radio label, magnetic resonant species, particle or enzyme label to the peptide; or indirect by attaching any for of label to a molecule which will itself react with the peptide. The chemistry of bonding a label to the peptide can be directly through a moiety already present in the peptide, such as an amino group, or through an intermediate moiety, such as a maleimide group. Capture of the antibody may be on any of the surfaces already mentioned by any reagent including passive or activated adsorption which will result in specific antibody or immune complexes being bound. In particular, capture of the antibody could be by anti-species or anti-immunoglobulin-sub-type, by rheumatoid factor, proteins A, G and the like, or by any molecule containing an epitope contained in the peptide.

The labelled peptide may be used in a competitive binding fashion in which its binding to any specific molecule on any of the surfaces exemplified above is blocked by antigen in the sample. Alternatively, it may be used in a non-competitive fashion in which antigen in the sample is bound specifically or non-specifically to any of the surfaces above and is also bound to a specific bi- or poly-valent molecule (e.g. an antibody) with the remaining valencies being used to capture the labelled peptide.

Often in homogeneous assays the peptide and an antibody are separately labelled so that, when the antibody reacts with the recombinant peptide in free solution, the two labels interact to allow, for example, non-radiative transfer of energy captured by one label to the other label with appropriate detection of the excited second label or quenched first label (e.g. by fluorimetry, magnetic resonance or enzyme measurement). Addition of either viral peptide or antibody in a sample results in restriction of the interaction of the labelled pair and thus in a different level of signal in the detector.

A suitable assay format for detecting HCV antibody is the direct sandwich enzyme immunoassay (EIA) format. A peptide is coated onto microtitre wells. A test sample and a peptide to which an enzyme is coupled are added simultaneously. Any HCV antibody present in the test sample binds both to the peptide coating the well and to the enzyme-coupled peptide. Typically, the same peptide are used on both sides of the sandwich. After washing, bound enzyme is detected using a specific substrate involving a colour change. A test kit for use in such an EIA comprises:

(1) a peptide, as herein defined labelled with an enzyme;
(2) a substrate for the enzyme;
(3) means providing a surface on which a peptide is immobilised; and
(4) optionally, washing solutions and/or buffers.

It is also possible to use IgG/IgM antibody capture ELISA wherein an antihuman antibody is coated onto microtiter wells, a test sample is added to the well. Any IgG or IgM antibody present in the test sample will then bind to the anti-human antibody. A peptide of the present invention, which has been labelled, is added to the well and the peptide will bind to any IgG or IgM antibody which has resulted due to infection by HCV. The IgG or IgM antibody can be visualized by virtue of the label on the peptide.

It can thus be seen that the peptides of the present invention may be used for the detection of HCV infection in many formats, namely as free peptides, in assays including classic ELISA, competition ELISA, membrane bound EIA and immunoprecipitation. Peptide conjugates may be used in amplified assays and IgG/IgM antibody capture ELISA.

An assay of the present invention may be used, for example, for screening donated blood or for clinical purposes, for example, in the detection and monitoring of HCV infections. For screening purposes, the preferred assay formats are those that can be automated, in particular, the microtitre plate format and the bead format. For clinical purposes, in addition to such formats, those suitable for smaller-scale or for single use, for example, latex assays, may also be used. For confirmatory assays in screening procedures, antigens may be presented on a strip suitable for use in Western or other immunoblotting tests.

As indicated above, assays used currently to detect the presence of anti-HCV antibodies in test samples, particularly in screening donated blood, utilise antigenic peptides obtained from HIV type 1 only and, as demonstrated herein, such antigens do not reliably detect other HCV genotypes. Accordingly, it is clearly desirable to supplement testing for HIV-1 with testing for all other genotypes, for example, types 2, 3 and 4, and also any further genotypes that may be discovered.

To test for a spectrum of genotypes, there may be provided a series of assay means each comprising one or more antigenic peptides from one genotype of HCV, for example, a series of wells in a microtitre plate, or an equivalent series using the bead format. Such an assay format may be used to determine the genotype of HCV present in a sample. Alternatively, or in addition, an assay means may comprise antigenic peptides from more than one genotype, for example, a microwell or bead may be coated with peptides from more than one genotype.

It has been found advantageous to use more than one HCV antigen for testing, in particular, a combination comprising at least one antigenic peptide derived from the structural region of the genome and at least one antigenic peptide derived from the non-structural region, especially a combination of a core antigen and at least one antigen selected from the NS3, NS4 and NS5 regions. The wells or beads may be coated with the antigens individually. It has been found advantageous, however, to fuse two or more antigenic peptides as a single polypeptide, preferably as a recombinant fusion polypeptide. Advantages of such an approach are that the individual antigens can be combined in a fixed, predetermined ratio (usually equimolar) and that only a single polypeptide needs to be produced, purified and characterised. One or more such fusion polypeptides may be used in an assay, if desired in addition to one or more unfused peptides. It will be appreciated that there are many possible combinations of antigens in a fusion polypeptide, for example, a fusion polypeptide may comprise a desired range of antigens from one serotype only, or may comprise antigens from more than one serotype. The antigenic peptides from serotypes 2, 3 and 4 are preferably those described herein.

To obtain a polypeptide comprising multiple peptide antigens, it is preferred to fuse the individual coding sequences into a single open reading frame. The fusion should, of course, be carried out in such a manner that the antigenic activity of each component peptide is not significantly compromised by its position relative to another peptide. Particular regard should of course be had for the nature of the sequences at the actual junction between the peptides. The resulting coding sequence can be expressed, for example, as described above in relation to recombinant peptides in general. The methods by which such a fusion polypeptide can be obtained are known in the art, and the production of a recombinant fusion polypeptide comprising multiple antigens of a strain of HCV type 1 is described in GB-A-2 239 245 immunoprecipitation. Peptide conjugates may be used in amplified assays and IgG/IgM antibody capture ELISA.

The peptide of the present invention may be incorporated into a vaccine formulation for inducing immunity to HCV in man. For this purpose the peptide may be presented in association with a pharmaceutically acceptable carrier.

For use in a vaccine formulation, the peptide may optionally be presented as part of an hepatitis B core fusion particle, as described in Clarke et al (*Nature, 1987, 330, 381–384*), or a polylysine based polymer, as described in Tam (*PNAS, 1988, 85, 5409–5413*). Alternatively, the peptide may optionally be attached to a particulate structure, such as liposomes or ISCOMS.

Pharmaceutically acceptable carriers include liquid media suitable for use as vehicles to introduce the peptide into a patient. An example of such liquid media is saline solution. The peptide may be dissolved or suspended as a solid in the carrier.

The vaccine formulation may also contain an adjuvant for stimulating the immune response and thereby enhancing the effect of the vaccine. Examples of adjuvants include aluminium hydroxide and aluminium phosphate.

The vaccine formulation may contain a final concentration of peptide in the range from 0.01 to 5 mg/ml, preferably from 0.03 to 2 mg/ml. The vaccine formulation may be incorporated into a sterile container, which is then sealed and stored at a low temperature, for example 4° C., or may be freeze-dried.

In order to induce immunity in man to HCV, one or more doses of the vaccine formulation may be administered. Each dose may be 0.1 to 2 ml, preferably 0.2 to 1 ml. A method for inducing immunity to HCV in man, comprises the administration of an effective amount of a vaccine formulation, as hereinbefore defined.

The present invention also provides the use of a peptide as herein defined in the preparation of a vaccine for use in the induction of immunity to HCV in man.

Vaccines of the present invention may be administered by any convenient method for the administration of vaccines including oral and parenteral (e.g. intravenous, subcutaneous or intramuscular) injection. The treatment may consist of a single dose of vaccine or a plurality of doses over a period of time.

LITERATURE CITED

1a. Chan, S. W. McOmish. F. Holmes. E. C. Dow. B. Pentherer. J. F. Follett. E. Yap. P. L. and Simmonas. P. (1992). *J. Gen Virol:* 73: 1131–1141.

1. Chan. S. W. P. Simmonas. F. McOmish. P. L. Yap. R. Mitchell. B. Dow. and E. Follett. 1991. Serological reactivity of blood donors infected with three different types of hepatitis C virus Lancet 338: 1391.

2. Chomczynski. P. and N. Sacchi. 1987. Single-step method or RNA isolation by acid guanidinium thiocyanate-phenol-chloroform extraction. Anal. Biochem. 162: 156–159.

3. Choo. Q. L. G. Kuo. A. J. Weiner. L. R. Overby, D. W. Bradley, and M. Houghton. 1989. Isolation of a cDNA derived from a blood-borne non-A, non-B hepatitis genome. Science 244: 359–362.

4. Choo. Q., L. K. H. Richman. J. H. Han. K. Berger, C. Lee. C. Dong. C. Gallegos. D. Colt. R. Medina Selby. P. J. Barr. A. J. Weiner. D. W. Bradley, G. Kuo. and M. Houghton. 1991. Genetic organization and diversity of the hepatitis C virus, Proc. Natl Acad Sci U.S.A. 88: 2451–2455.

5. Coeien. R. J. and J. S. Mackenzie. 1990. The 5' terminal non-coding region of Murray Valley encephalitis virus RNA is highly conserved J. Gen. Virol. 71: 241–245.

6. Devereux. J. P. Haeberii. and O. Smithies. 1984. Comprehensive set of sequence analysis programs for the VAX Nucleic. Acids. Res. 12: 387–395.

7. Enomoto. N. A. Takada. T. Nakao. and T. Date. 1990. There are two major types of hepatitis C virus in Japan Biochem Biophys. Res. Commun. 170: 1021–1025. Esteban. J. L. A. Gonzaiez. J. M. Hernandez. L. Viladomiu. C. Sanchez. J. C. Lopez Talavera. D. Lucea. C. Martin Vega. X. Vidal. R. Estaban. and J. Guardia. 1990. Evaluation of antibodies to hepatitis C virus in a study of transfusion-associated hepatitis. N. Engl. J. Med. 323: 1107–1112.

9. Felsenstein J. 1988. Phylogenies from molecular sequences: inference and reliability. Ann. Rev. Genet. 22: 521–565.

10. Follett. E. A. C. B. C. Dow. F. McOmish. P. L. Yap. W. Hughes. R. Mitchell. and P. Simmonds. 1991. HCV confirmatory testing of blood donors. Lancet 338: 1024.

11. Fuchs. K. M. Motz. E. Schreir. R. Zachoval. F. Deinhardt. and M. Roggendorf. 1991. Characterization of nucleotide sequences from European hepatitis C virus isolates. Gene 103: 163–169.

12. Garson. J. A. C. Ring. P. Tuke. and R. S. Tedder. 1990. Enhanced detection by PCR of hepatitis C virus RNA. Lancet 336: 878–879.

12a. Geysen. H. M. Barteling, S. J. and Meloen. R. H. (1985). *Proc Natl Acad Sci U.S.A.* 82: 178–182.

12b. Geysen. H. M. Meloen. R. H. and Barteling. S. J. (1984). *Proc Natl Acad Sci U.S.A.:* 81: 3998–4003.

13. Han. J. H. V. Shyamaia. K. H. Richman. M. J. Brauer. B. Irvine. M. S. Urdea. P. Tekamp Olson. G. Kuo. Q. L. Choo. and M. Houghton. 1991. Characterization of the terminal regions of hepatitis C viral RNA identification of conserved sequences in the 5' untranslated region and poly (A)tails at the 3' end. Proc. Natl. Acad. Sci. U.S.A. 88: 1711–1715.

14. Hosein. B., C. T. Fang. M. A. Popovsky, J. Ye. M. Zhang. and C. Y. Wang. 1991. Improved serodiagnosis of hepatitis C virus infection with synthetic peptide antigen from capsid protein Proc. Natl. Acad. Sci. U.S.A. 88: 3647–3651.

15. Japanese Red Cross Non-A. Non-B Hepatitis Research Group 1991. Effect of screening for hepatitis C virus antibody and hepatitis B virus core antibody on the incidence of post-transfusion hepatitis. Lancet 338: 1040–1041.

16. Kato. N., M. Hijikata. Y. Ootsuyama. M. Nakagawa. S. Ohkoshi. T. Sugimura. and K. Shimotohno. 1990. Molecular cloning of the human hepatitis C virus genome from Japanese patients with non-A. non-B hepatitis. Proc. Natl. Acad. Sci. U.S.A. 87: 9524–9528.

17. Kubo. Y., K. Takeuchi, S. Boonmar. T. Katayama. Q. L. Choo. G. Kuo. A. J. Weiner. D. W. Bradley, M. Houghton, I. Saito, and T. Miyamura. 1989. A cDNA fragment of hepatitis C virus isolated from an implicated donor of post-transfusion non-A, non-B hepatitis in Japan. Nucleic. Acids. Res. 17: 10367–10372.

18. Kuo. G., Q. L. Choo. H. J. Alter. G. L. Gitnick. A. G. Redeker, R. H. Purcell, T. Miyamura. J. L. Dienstag. M. J.

Alter, C. E. Stevens, G. E. Tegtmeier, F. Bonino, M. Columbo. W. S. Less. C. Kuo. K. Berger. J. R. Shuster. L. R. Overby, D. W. Bradley, and M. Houghton. 1989. An assay for circulating antibodies to a major etiologic virus of human non-A. non-B hepatitis. Science 244: 362–364.

19. Lain. S., J. L. Reichmann, M. T. Martin, and J. A. Garcia, 1989. Homologous polyvirus and flavivirus proteins belonging to a superfamily or helicase-like proteins. Gene 82: 357–362.

20. Mandl. C. W., F. X. Heinz, and C. Kunz. 1988. Sequence of the structural proteins of tick-borne encephalitis virus (Western subtype) and comparative analysis with other flaviviruses. Virology 166: 197–205.

21. Miller, R. H. and R. H. Purcell. 1990. Hepatitis C virus shares amino acid sequence similarity with pestiviruses and flaviviruses as well as members of two plant virus supergroups. Proc. Natl. Acad. Sci. U.S.A. 87: 2057–2061.

22. Muraiso, K., M. Hijikata. S. Ohkoshi, M. J. Cho. M. Kikuchi, N. Kato, and K. Shimotohno, 1990. A structural protein of hepatitis C virus expressed in *E. coli* facilitates accurate detection of hepatitis C virus. Biochem. Biophys. Res. Commun. 172: 511–516.

23. Nakao, T., N. Enomoto, N. Takada, A. Takada, and T. Date. 1991. Typing of hepatitis C virus (HCV) genomes by restriction fragment length polymorphisms. J. Gen. Virol. 72: 2105–2112.

24. Ogata, N., H. J. Alter, R. H. Miller, and R. H. Purcell. 1991. Nucleotide sequence and mutation rate of the H strain of hepatitis C virus. Proc. Natl. Acad. Sci. U.S.A. 88: 3392–3396.

25. Okamoto. H., S. Okada, Y. Sugiyama. T. Tanaka. Y. Sugai, Y. Akahane. A. Machida. S. Mishiro. H. Yoshizawa. Y. Miyakawa, and M. Mayumi. 1990. Detection of hepatitis C virus RNA by a two-stage polymerase chain reaction with two pairs of primers deduced from the 5'-noncoding region. Jpn. J. Exp. Med. 60: 215–222.

26. Okamoto, H., S. Okada. Y. Sugiyama. S. Yotsumoto. T. Tanaka. H. Yoshizawa. F. Tsuda. Y. Miyakawa. and M. Mayumi. 1990. The 5'-terminal sequence of the hepatitis C virus genome. Jpn. J. Exp. Med. 60: 167–177.

27. Pozzato. G., M. Moretti. F. Franzin. L. S. Croce. C. Tiribelli. T. Masayu. S. Kaneko. M. Unoura. and K. Kobayashi. 1991. Severity or liver disease with different hepatitis C viral clones. Lancet 338: 509.

28. Saiton, N. and T. Imanishi. 1989. Relative efficiencies of the Fitch-Margoliash, maximum-parsimony, maximum-likelihood, minimum evolution, and neighbor-joining methods of phylogenetic tree construction in obtaining the correct tree. Mol. Biol. Evol. 6: 514–525.

29. Saitou, N. and M. Nei. 1987. The neighbor-joining method: a new method for reconstructing phylogenetic trees. Mol. Biol. Evol. 4: 406–425.

30. Simmonds, P., P. Balfe, J. F. Peutherer. C. A. Ludlam, J. O. Bishop, and A. J. Leigh Brown. 1990. Human immunodeficiency virus-infected individuals contain provirus in small numbers of peripheral mononuclear cells and at low copy numbers. J. Virol. 64: 864–872.

31. Simmonds, P., L. Q. Zhang. H. G. Watson. S. Rebus, E. D. Ferguson, P. Balfe, G. H. Leadbetter, P. L. Yap, J. F. Peutherer, and C. A. Ludlam, 1990. Hepatitis C quantification and sequencing in blood products, haemophiliacs, and drug users. Lancet 336: 1469–1472.

32. Staden, R. 1984. Graphic methods to determine the function of nucleic acid sequences. Nucleic. Acids. Res. 12: 521–538.

33. Takamizawa, A., C. Mori, I. Fuke. S. Manabe. S. Murakami. J. Fujita. E. Onishi. T. Andoh. I. Yoshida. and H. Okayama. 1991. Structure and organization of the hepatitis C virus genome isolated from human carriers. *J. Virol.* 65: 1105–1113.

34. Takeuchi. K., Y. Kubo. S. Boonmar. Y. Watanabe. T. Katayama. Q. L. Choo. G. Kuo. M. Houghton. I. Saito. and T. Miyamura. 1990. Nucleotide sequence of core and envelope genes of the hepatitis C virus genome derived directly from human healthy carriers. Nucleic. Acids. Res. 18: 4626.

35. Ksukiyama-Kohara. K., M. Kohara. K. Yamaguchi. N. Maki. A. Toyoshima. K. Miki. S. Tanaka. N. Hattori. and A. Nomoto. 1991. A second group of hepatitis C virus. Virus Genes 5: 243–254.

36. van der Poel. C. L., H. T. Cuypers. H. W. Reesink. A. J. Weiner. S. Quan. R. Di Nello. J. J. Van Boven. I. Winkel. D. Mulder Folkerts. P. J. Exel Oehlers. W. Schaasberg, A. Leentvaar-Kuypers, A. Polito, M. Houghton, and P. N. Lelie. 1991. Confirmation of hepatits C virus infection by new four-antigen recombinant immunoblot assay. Lancet 337: 317–319.

37. Weiner, A. J., G. Kuo. D. W. Bradley, F. Bonino, G. Saracco, C. Lee. J. Rosenblatt, Q. L. Choo, and M. Houghton. 1990. Detection of hepatitis C viral sequences in non-A. non-B hepatitis [see comments]. Lancet 335: 1–3.

---

We claim:

1. An isolated polynucleotide molecule having a sequence encoding a polypeptide selected from the group consisting of:
   (a) KPALVPDKEVLYQQYDEM (SEQ ID NO:1);
   (b) ECSQAAPYIEQAQVIAHQF (SEQ ID NO:2); and
   (c) a polypeptide of equivalent antigenicity, which polypeptide specifically binds to the same antibodies as are bound by the polypeptide of (a) or (b) above.

2. A peptide selected from the group consisting of:
   (a) KPALVPDKEVLYQQYDEM (SEQ ID NO:1),
   (b) ECSQAAPYIEQAQVIAHQF (SEQ ID NO:2), and
   (c) a polypeptide of equivalent antigenicity, which polypeptide specifically binds to the same antibodies as are bound by the polypeptide of (a) or (b) above.

3. An immunoassay device which comprises a solid substrate having attached thereto the peptide according to claim 2.

4. A device according to claim 3 for HCV-typing wherein said solid substrate comprises a series of locations respectively containing HCV-1, HCV-2 and HCV-3 specific antigens.

5. A device according to claim 4 wherein said solid substrate further comprises a location containing HCV-4 specific antigens.

6. A device according to claim 3 wherein at each location is provided a blocking amount of heterologous-type HCV oligopeptides, to ensure that only antibody with type-specific antibody reactivity binds to the solid surface.

7. An immunoassay device for HCV screening which comprises a solid substrate having attached thereto a plurality of antigens, said plurality of antigens comprising the peptide according to claim 2.

8. A device according to claim 7 wherein said plurality of antigens further comprises peptides of HCV types 1 and 2.

9. A device according to claim 8 wherein the peptide of HCV type 1 is an NS4 peptide comprising a sequence selected from the group consisting of the HCV-1 amino acid sequence from position 1691 to 1708 and the HCV-1 amino acid sequence from position 1710 to 1728, numbered according to a prototype HCV-1 amino acid sequence.

10. A device according to claim 8 wherein the peptide of HCV type 2 is an NS4 peptide comprising a sequence selected from the group consisting of the HCV-2 amino acid sequence from position 1691 to 1708 and the HCV-2 amino acid sequence from position 1710 to 1728 numbered according to a prototype HCV-1 amino acid sequence.

11. A device according to claim 8 wherein the HCV-2 peptide sequence is selected from the group consisting of SEQUENCE ID NO: 3, SEQUENCE ID NO: 4, SEQUENCE ID NO: 5 and SEQUENCE ID NO: 6.

12. A device according to claim 8 wherein the peptide of HCV-1 peptide sequence is selected from the group consisting of SEQUENCE ID NO:7, SEQUENCE ID NO:8, SEQUENCE ID NO:10 and SEQUENCE ID NO:11.

13. A substrate having a solid surface and the peptide according to claim 2 attached to the solid surface.

14. A substrate for HCV screening, said substrate having a solid surface, wherein said solid surface has attached thereto a plurality of antigens, said plurality of antigens comprising the peptide according to claim 2.

15. A polypeptide comprising the peptide of claim 12.

16. An antigenic HCV-3 type-specific peptide comprising an NS4 epitope, said NS4 epitope having a sequence corresponding to amino acids 1691 to 1708 or to amino acids 1710 to 1728 of HCV-3 NS4 polypeptide, numbered according to a prototype HCV-1 amino acid sequence.

17. A substrate having a solid surface and the peptide according to claim 16 attached to the solid surface.

18. A substrate for HCV screening, said substrate having a solid surface, wherein said solid surface has attached thereto a plurality of antigens, said plurality of antigens comprising the peptide according to claim 16.

19. An immunoassay device which comprises a solid substrate having attached thereto the peptide according to claim 16.

20. An immunoassay device for HCV screening which comprises a solid substrate having attached thereto a plurality of antigens, said plurality of antigens comprising the peptide according to claim 16.

21. A device according to claim 20, wherein said plurality of antigens comprises a peptide of HCV type 1 and a peptide of HCV type 2.

22. A device according to claim 21 wherein the peptide of HCV type 2 is an NS4 peptide comprising a sequence selected from the group consisting of the HCV-2 amino acid sequence from position 1691 to 1708 and the HCV-2 amino acid sequence from position 1710 to 1728 numbered according to a prototype HCV-1 amino acid sequence.

23. A device according to claim 22 wherein the HCV-2 peptide sequence is selected from the group consisting of SEQUENCE ID NO:3, SEQUENCE ID NO:4, SEQUENCE ID NO:5 and SEQUENCE ID NO:6.

24. A device according to claim 21 wherein the peptide of HCV type 1 is an NS4 peptide comprising a sequence selected from the group consisting of the HCV-1 amino acids sequence from position 1691 to 1708 and the HCV-1 amino acid sequence from position 1710 to 1728, numbered according to a prototype HCV-1 amino acid sequence.

25. A device according to claim 24 wherein the HCV-1 peptide sequence is selected from the group consisting of SEQUENCE ID NO:7, SEQUENCE ID NO:8, SEQUENCE ID NO:10 and SEQUENCE ID NO:11.

26. A polynucleotide coding for an antigenic HCV-3 type-specific peptide according to claim 16.

27. An antigenic HCV-3 nonameric oligopeptide selected from the group consisting of:
   (a) KPALVPDKE (sequence 13 of FIG. 11a; residues 1 to 9 in SEQ ID NO: 1);
   (b) PALVPDKEV (sequence 14 of FIG. 11a; residues 2 to 10 in SEQ ID NO: 1);
   (c) ALVPDKEVL (sequence 15 of FIG. 11a; residues 3 to 11 in SEQ ID NO: 1);
   (d) LVPDKEVLY (sequence 16 of FIG. 11a; residues 4 to 12 in SEQ ID NO: 1);

(e) VPDKEVLYO (sequence 17 of FIG. 11a; residues 5 to 13 in SEQ ID NO: 1);

(f) PDKEVLYOO (sequence 18 of FIG. 11a; residues 6 to 14 in SEQ ID NO: 1);

(g) DKEVLYOOY (sequence 19 of FIG. 11a; residues 7 to 15 in SEQ ID NO: 1);

(h) KEVLYOOYD (sequence 20 of FIG. 11a; residues 8 to 16 in SEQ ID NO: 1);

(i) EVLYOOYDE (sequence 21 of FIG. 11a; residues 9 to 17 in SEQ ID NO: 1);

(j) VLYOOYDEM (sequence 22 of FIG. 11a; residues 10 to 18 in SEQ ID NO: 1);

(k) ECSOAAPYI (sequence 32 of FIG. 11a; residues 1 to 9 of SEQ ID NO: 2);

(l) CSOAAPYIE (sequence 33 of FIG. 11a; residues 2 to 10 of SEQ ID NO: 2);

(m) SOAAPYIEO (sequence 34 of FIG. 11a; residues 3 to 11 of SEQ ID NO: 2);

(n) OAAPYIEOA (sequence 35 of FIG. 11a; residues 4 to 12 of SEQ ID NO: 2);

(o) AAPYIEOAO (sequence 36 of FIG. 11a; residues 5 to 13 of SEQ ID NO: 2);

(p) APYIEOAOV (sequence 37 of FIG. 11a; residues 6 to 14 of SEQ ID NO: 2);

(q) APYIEOAOV (sequence 38 of FIG. 11a; residues 7 to 15 of SEQ ID NO: 2);

(r) YIEOAOVIA (sequence 39 of FIG. 11a; residues 8 to 16 of SEQ ID NO: 2);

(s) IEOAOVIAH (sequence 40 of FIG. 11a; residues 9 to 17 of SEQ ID NO: 2);

(t) EOAOVIAHO (sequence 41 of FIG. 11a; residues 10 to 18 of SEQ ID NO: 2); and (u) OAOVIAHOF (sequence 42 of FIG. 11a; residues 11 to 19 of SEQ ID NO: 2).

* * * * *

UNITED STATES PATENT AND TRADEMARK OFFICE
CERTIFICATE OF CORRECTION

PATENT NO. : 5,763,159
DATED : June 9, 1998
INVENTOR(S) : Simmonds et al.

It is certified that error appears in the above-identified patent and that said Letters Patent is hereby corrected as shown below:

Column 6, line 15, "13(c)" should be -- 13(d) --.

Column 70, line 15, "claim 12" should be -- claim 2 --.

Column 71, line 1, "VPDKEVLYO" should be -- VPDKEVLYQ --.

Column 71, line 3, "PDKEVLYOO" should be -- PDKEVLYQYQQ --.

Column 71, line 5 "DKEVLYOOY" should be --DKEVLYQQY--.

Column 71, line 7 "KEVLYOOYD" should be -- KEVLYQQYD --.

Column 71, line 9 "EVLYOOYDE" should be -- EVLYQQYDE --.

Column 71, line 11 "VLYOOYDEM" should be -- VLYQQYDEM --.

Column 71, line 13 "ECSOAAPYI" should be -- ECSQAAPYI --.

Column 71, line 15 "CSOAAPYIE" should be -- CSQAAPYIE --.

Column 71, line 17 "SOAAPYIEO" should be -- SQAAPYIEQ --.

Column 72, line 1 "OAAPYIEOA" should be -- QAAPYIEQA --.

Column 72, line 3 "AAPYIEOAO" should be -- AAPYIEQAQ --.

UNITED STATES PATENT AND TRADEMARK OFFICE
CERTIFICATE OF CORRECTION

PATENT NO. : 5,763,159
DATED : June 9, 1998
INVENTOR(S) : Simmonds et al.

It is certified that error appears in the above-identified patent and that said Letters Patent is hereby corrected as shown below:

```
Column 72, line 5 "APYIEOAOV" should be -- APYIEQAQV --.

Column 72, line 7, "APYIEOAOV" should be -- PYIEQAQVI --.

Column 72, line 9, "YIEOAOVIA" should be -- YIEQAQVIA --.

Column 72, line 11, "IEOAOVIAH" should be
-- IEQAQVIAH --.

Column 72, line 13, "EOAOVIAHO" should be
-- EQAQVIAHQ --.

Column 72, line 15, "OAOVIAHOF" should be
-- QAQVIAHQF --.
```

Signed and Sealed this

Seventeenth Day of November, 1998

Attest:

BRUCE LEHMAN

*Attesting Officer*   *Commissioner of Patents and Trademarks*